US012729186B2

(12) United States Patent
Xu et al.

(10) Patent No.: US 12,729,186 B2
(45) Date of Patent: Sep. 8, 2026

(54) PRODRUGS FOR SUSTAINED RELEASING THERAPEUTIC AGENTS AND USES THEREOF

(71) Applicant: LIANGJIANG MEDICINE CO., LTD., Chongqing (CN)

(72) Inventors: Liyan Xu, Chongqing (CN); Yong Liu, Chongqing (CN); Weijiang Zhang, Redwood City, CA (US); Hao Zhang, Foster City, CA (US); Xiaohuan Tang, Chongqing (CN); Xiaoli Shen, Chongqing (CN); Xingchun Fang, Coquitlam (CA)

(73) Assignee: Liangjiang Medicine Co., Ltd., Chongqing (CN)

( * ) Notice: Subject to any disclaimer, the term of this patent is extended or adjusted under 35 U.S.C. 154(b) by 582 days.

(21) Appl. No.: 18/033,210

(22) PCT Filed: Oct. 21, 2021

(86) PCT No.: PCT/CN2021/125237

§ 371 (c)(1),
(2) Date: Apr. 21, 2023

(87) PCT Pub. No.: WO2022/083679

PCT Pub. Date: Apr. 28, 2022

(65) Prior Publication Data

US 2023/0391731 A1 Dec. 7, 2023

(30) Foreign Application Priority Data

Oct. 23, 2020 (WO) ................ PCT/CN2020/123167
Sep. 9, 2021 (WO) ................ PCT/CN2021/117394

(51) Int. Cl.

| | |
|---|---|
| ***C07D 239/553*** | (2006.01) |
| ***C07D 401/12*** | (2006.01) |
| ***C07D 487/04*** | (2006.01) |
| ***C07D 491/22*** | (2006.01) |
| ***C07F 9/6512*** | (2006.01) |
| ***C07F 9/6561*** | (2006.01) |
| ***C07H 15/252*** | (2006.01) |

(52) U.S. Cl.

CPC ....... *C07D 239/553* (2013.01); *C07D 401/12* (2013.01); *C07D 487/04* (2013.01); *C07D 491/22* (2013.01); *C07F 9/6512* (2013.01); *C07F 9/6561* (2013.01); *C07H 15/252* (2013.01)

(58) Field of Classification Search

CPC .............. C07D 239/553; C07D 401/12; C07D 487/04; C07D 491/22; C07F 9/6512; C07F 9/6561; C07H 15/252

See application file for complete search history.

(56) References Cited

U.S. PATENT DOCUMENTS

| | | | | | |
|---|---|---|---|---|---|
| 4,130,648 | A | * | 12/1978 | Kijima | A61K 31/505 544/310 |
| 5,610,160 | A | | 3/1997 | Sloan et al. | |
| 2007/0161668 | A1 | | 7/2007 | Soon-Shiong et al. | |
| 2013/0331422 | A1 | | 12/2013 | Chen | |

FOREIGN PATENT DOCUMENTS

| | | | | | |
|---|---|---|---|---|---|
| CN | 105315294 | A | | 2/2016 | |
| CN | 112618550 | A | | 4/2021 | |
| CN | 112724088 | A | | 4/2021 | |
| WO | WO-8706581 | A1 | * | 11/1987 | C07D 239/553 |
| WO | WO-9520567 | A1 | * | 8/1995 | A61P 43/00 |
| WO | WO-2004092205 | A1 | * | 10/2004 | A61P 35/00 |
| WO | WO-2011072240 | A1 | * | 6/2011 | A61K 31/425 |

OTHER PUBLICATIONS

Suppasansatorn, P. et al. Skin delivery potency and antitumor activities of temozolomide ester prodrugs. Cancer Letters 2006, 244, 42-52. (Year: 2006).*

Federal Register, vol. 76, No. 27, Wednesday, Feb. 9, 2011. (Year: 2011).*

Møllgaard, B. et al. Pro-drugs as drug delivery systems XXIII. Improved dermal delivery of 5-fluorouracil through human skin via N-acyloxymethyl pro-drug derivatives. International Journal of Pharmaceutics 1982, 12, 153-162. (Year: 1982).*

Takayama, H. et al. Synthesis of a new class of camptothecin derivatives, the long-chain fatty acid esters of 10-hydroxycamptothecin, as a potent prodrug candidate, and their in vitro metabolic conversion by carboxylesterases. Bioorg. Med. Chem. Lett. 1998, 8, 415-418. (Year: 1998).*

(Continued)

*Primary Examiner* — Jeffrey H Murray
*Assistant Examiner* — Kristen W Romero
(74) *Attorney, Agent, or Firm* — Foley & Lardner LLP

(57) ABSTRACT

The present disclosure relates to prodrugs for sustained releasing therapeutic agents, and methods for using such prodrugs for the treatment of diseases. The present disclosure provides a prodrug compound comprising a parent drug moiety and a tail moiety, wherein the parent drug moiety is derived from a parent drug comprising a reactive group selected from the group consisting of amine, amino, hydroxyl, carboxylate, ketone, and amide, the tail moiety is covalently linked to the parent drug moiety and has a Formula (I):

(I)

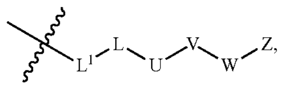

a pharmaceutical composition comprising the prodrug compound provided herein or a pharmaceutically acceptable salt thereof and a pharmaceutically acceptable excipient, and a method of treating diseases in a subject in need thereof.

2 Claims, 2 Drawing Sheets

(56) References Cited

OTHER PUBLICATIONS

Boisdron-Celle, M. et al. Preparation and characterization of 5-fluorouracil-loaded microparticles as biodegradable anticancer drug carriers. J. Pharm. Pharmacol. 1995, 47:108-114. (Year: 1995).*

Baldrick, P. Pharmaceutical Excipient Development: The Need for Preclinical Guidance. Regulatory Toxicology and Pharmacology 2000, 32, 210-218. (Year: 2000).*

Longley, D. B. et al. 5-Fluorouracil: mechanisms of action and clinical strategies. Nat Rev Cancer 2003, 3, 330-338. (Year: 2003).*

Buur, A. et al. Prodrugs of 5-fluorouracil. Acta Pharm. Suec. 1986, 205-216. (Year: 1986).*

International Search Report and Written Opinion for PCT Application No. PCT/CN2021/125237, dated Jan. 18, 2022.

Buur, Anders et al. "Prodrugs of 5-fluorouracil VII. Hydrolysis kinetics and physicochemical properties of N-ethoxy- and N-phenoxycarbonyloxymethyl derivatives of 5-fluorouracil" Acta Pharm. Suec., vol. 23, No. 4, Dec. 31, 1986 (Dec. 31, 1986), pp. 205-216.

Nagase, Toshio et al. "5-Fluorouracil derivatives. XIV. Selective synthesis of 1-[[(alkoxycarbonyl)oxy]methyl]-5-fluorouracils via 1, 3-bis (hydroxymethyl)-5-fluorouracil" Heterocycles, vol. 27, No. 5, Dec. 31, 1988 (Dec. 31, 1988), pp. 1155-1158.

Suda, Yasuo et al. "The synthesis and in vitro and in vivo stability of 5-fluorouracil prodrugs which possess serum albumin binding potency" Biological & Pharmaceutical Bulletin, vol. 16, No. 9, Dec. 31, 1993 (Dec. 31, 1993), pp. 876-878.

Zhang, Lina et al. "Behavior of short-chain chemotherapeutic polyelectrolytes in solutions" Gaodeng Xuexiao Huaxue Xuebao, vol. 7, No. 5, Dec. 31, 1986 (Dec. 31, 1986), pp. 465-469.

Zhu, Qi wen et al. "A series of camptothecin prodrugs exhibit HDAC inhibition activity" Bioorganic & Medicinal Chemistry, vol. 26, No. 16, Aug. 4, 2018 (Aug. 4, 2018).

Abraham, Sunny et al. "Synthesis of the next-generation fherapeutic antibodies fhat combine cell targeting and antibody-catalyzed prodrug activation" Proceedings of the National Academy of Sciences of the United States of America, vol. 104, No. 13, Mar. 27, 2007, pp. 5584-5589.

* cited by examiner

PRODRUGS FOR SUSTAINED RELEASING THERAPEUTIC AGENTS AND USES THEREOF

CROSS-REFERENCE TO RELATED APPLICATION

The present application is a U.S. National Phase Entry of International PCT Application No. PCT/CN2021/125237 having an international filing date of Oct. 21, 2021, and which claims priority to application PCT/CN2020/123167 filed on Oct. 23, 2020, and application PCT/CN2021/117394 filed on Sep. 9, 2021. The above mentioned applications are incorporated herein by reference in their entirety.

FIELD OF THE DISCLOSURE

The present disclosure relates to prodrugs for sustained releasing therapeutic agents, and methods for using such prodrugs for the treatment of diseases.

BACKGROUND OF THE DISCLOSURE

Most of the therapeutic agents are delivered to the body systemically via oral/GI absorption or systemic injection. Then the therapeutic agents are delivered to the action site by the blood circulation, thus, the therapeutic agent are exposed to the entire body. In some cases, the unintended exposure of the therapeutic agents in the other parts of the body may cause side effects, sometimes serious side effects. To reduce systemic exposure caused side effects, many locally delivered dosage forms are developed. One good example is the inhalation dosage form to treat respiratory diseases, such as COPD and asthma. These therapeutic agents target receptors on the airway and make the airway open for more efficient oxygen exchange. There are many other examples of local delivered drugs, such as topical corticosteroids for skin rash, intravitreal injection of anti-VEGF for wet AMD (age-related macular degeneration), intra-articular injection of corticosteroids to treat osteoarthritis. The purpose of these local delivered dosage form is to have high local drug concentration to have the therapeutic effective, yet to reduce systemic exposure of the drug to have minimum side effects. Local delivery dosage form, however, are difficult to use in most cases, especially the locally injected dosage forms. Therefore, it is desirable to have the delivery system, e.g., sustained or controlled release dosage form, that can release the drug slowly to have prolonged duration to reduce the frequency of dosing. The prodrug approach is one of the sustained release mechanism often used by people known in this field.

Drugs in the systemic circulation are metabolized and eliminated from the system by enzymes or excretion. In order to maintain a concentration above the effective concentration at all time, a peak concentration much higher than the effective concentration is needed so that the trough between each dosing would be above the effective concentrations. The peak concentration, however, in some cases, can cause undesirable side effect. There are many ways to reduce peak concentration without proportionally reduce trough concentration. The most popular approach is to use polymers to slow down the drug release from the dosing system. Many orally administrated sustained release/controlled release systems using this approach. There are pros and cons with this approach in some incidents, especially for locally injected delivery system targeting release duration in weeks or months. Using polymer system to control drug release may also have challenges in manufacturing process and quality control of the products. Another approach to have more precise control of the drug release is to have a prodrug that can release the drug via chemical bond breakage. In this case, the release mechanism is essentially a chemical reaction, more specifically, it's a first order chemical reaction. The rate of the drug release is much more predictable due to consistency of the environment in the biology system. Furthermore, by controlling the solubility of the prodrug, it is possible to create a system that can release the drug in a zero order or pseudo-zero manner using solubility as rate limiting step.

The present disclosure is related to a prodrug system that controls drug release rate via chemical structure of the prodrug moiety for the intended location and indication.

SUMMARY OF THE DISCLOSURE

In one aspect, the present disclosure provides a prodrug compound comprising a parent drug moiety and a tail moiety, wherein the parent drug moiety is derived from a parent drug comprising a reactive group selected from the group consisting of amine, amino, hydroxyl, carboxylate, ketone, and amide, the tail moiety is covalently linked to the parent drug moiety and has a Formula (I):

(I)

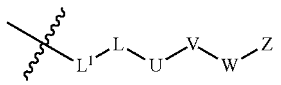

wherein:

$L^1$ is connected to the parent drug moiety through the reactive group of the parent drug to form a cleavable linkage;

L is a direct bond or alkyl;

U is selected from the group consisting of a direct bond, cycloalkyl, heterocyclyl, aryl and heteroaryl;

V is a direct bond or alkyl;

W is selected from the group consisting of a direct bond, cycloalkyl, heterocyclyl, aryl and heteroaryl;

Z is selected from the group consisting of a direct bond, alkyl, aryl, $NR^1R^2$, and $OR^3$, wherein said alkyl and aryl are optionally substituted with one or more $R^4$;

$R^1$, $R^2$ and $R^3$ are independently hydrogen, alkyl or cycloalkyl; and $R^4$ is selected from the group consisting of alkyl, cycloalkyl, heterocyclyl, aryl and heteroaryl, provided that when U is not a direct bond, V, W and Z are not direct bonds at the same time, or a pharmaceutically acceptable salt thereof.

In some embodiments, the present disclosure provides a prodrug compound having a formula selected from the group consisting of:

(II)

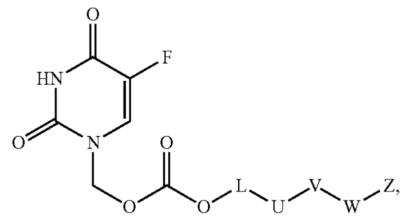

-continued (III)

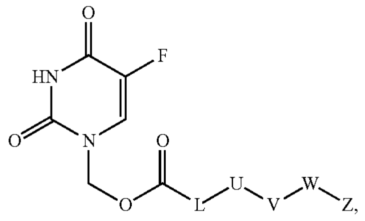

(IV)

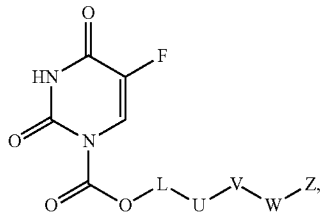

(V)

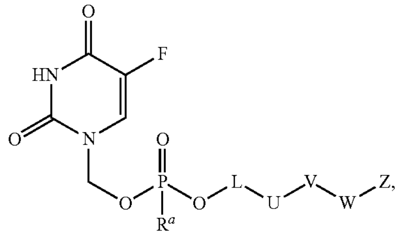

or a pharmaceutically acceptable salt thereof.

In some embodiments, the present disclosure provides a prodrug compound having a formula selected from the group consisting of:

(VI)

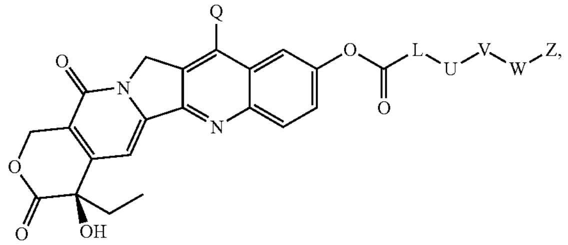

(VII)

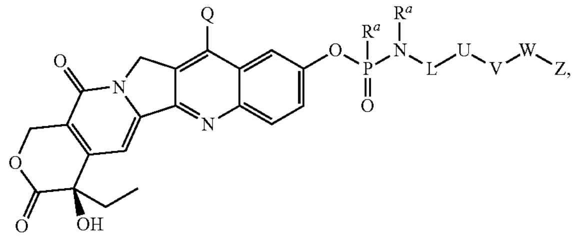

-continued (VIII)

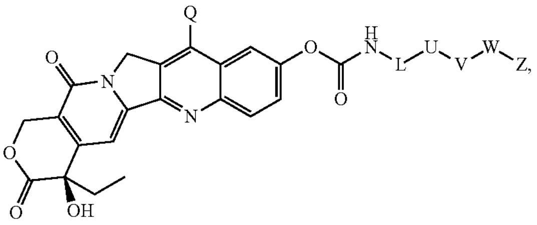

and (IX)

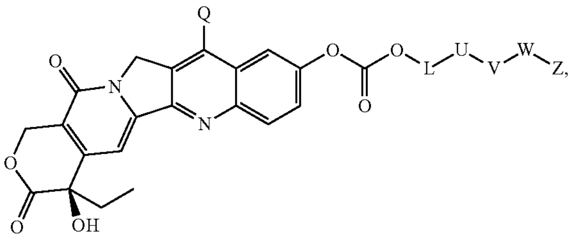

or a pharmaceutically acceptable salt thereof.

In some embodiments, the present disclosure provides a prodrug compound having a formula of:

(X)

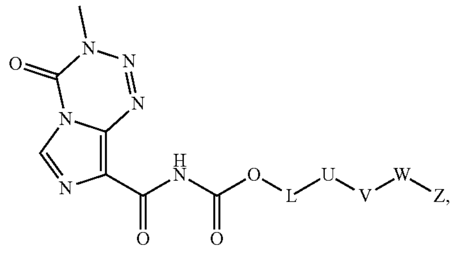

or (XI)

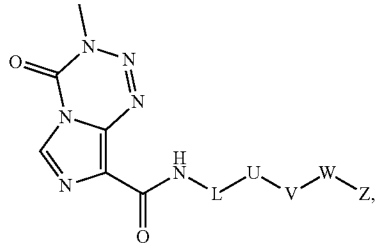

or a pharmaceutically acceptable salt thereof.

In some embodiments, the present disclosure provides a prodrug compound having a formula of:

(XII)

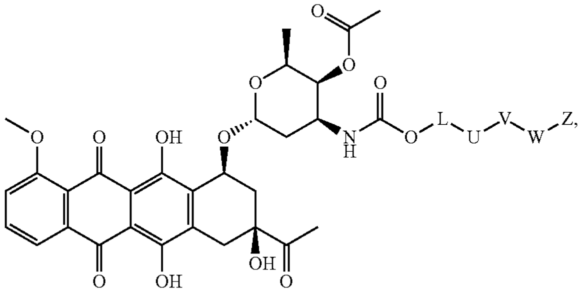

or a pharmaceutically acceptable salt thereof.

In a further aspect, the present disclosure provides a pharmaceutical composition comprising the prodrug compound provided herein or pharmaceutically acceptable salts thereof, and a pharmaceutically acceptable excipient.

In another aspect, the present disclosure provides a method of treating diseases in a subject in need thereof, comprising administering to the subject a therapeutic effective amount of the prodrug compound provided herein or pharmaceutically acceptable salts thereof, or the pharmaceutical composition provided herein.

DETAILED DESCRIPTION OF THE DISCLOSURE

Figure 1:
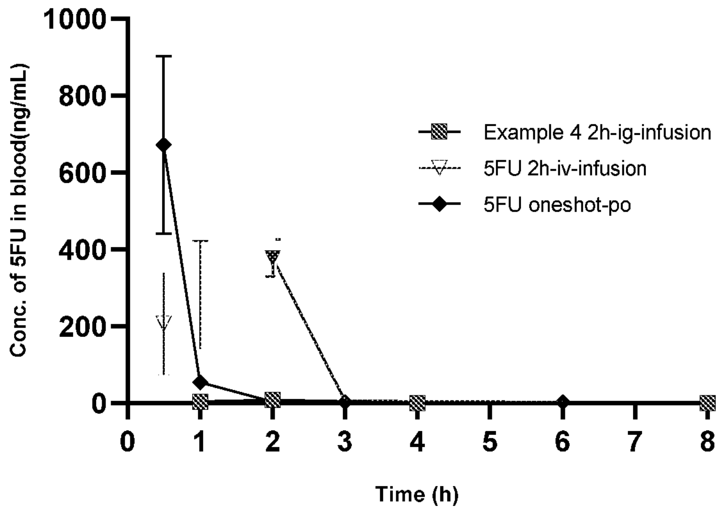
FIGS. 1 and 2 depict the plasma and gastric concentration of fluorouracil following the continuous intragastric administration of the exemplary compound of the present disclosure and the continuous intravenous infusion or single oral administration of free fluorouracil to male Sprague Dawley rats, respectively

Reference will now be made in detail to certain embodiments of the present disclosure, examples of which are illustrated in the accompanying structures and formulas. While the present disclosure will be described in conjunction with the enumerated embodiments, it will be understood that they are not intended to limit the present disclosure to those embodiments. On the contrary, the present disclosure is intended to cover all alternatives, modifications, and equivalents, which may be included within the scope of the present disclosure as defined by the claims. One skilled in the art will recognize many methods and materials similar or equivalent to those described herein, which could be used in the practice of the present disclosure. The present disclosure is in no way limited to the methods and materials described. In the event that one or more of the incorporated references and similar materials differs from or contradicts this application, including but not limited to defined terms, term usage, described techniques, or the like, the present disclosure controls. All references, patents, patent applications cited in the present disclosure are hereby incorporated by reference in their entireties.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination. It must be noted that, as used in the specification and the appended claims, the singular forms "a," "an," and "the" include plural forms of the same unless the context clearly dictates otherwise.

DEFINITIONS

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, $2^{nd}$ Edition, University Science Books, Sausalito, 2006; Smith and March March's Advanced Organic Chemistry, $6^{th}$ Edition, John Wiley & Sons, Inc., New York, 2007; Larock, Comprehensive Organic Transformations, $3^{rd}$ Edition, VCH Publishers, Inc., New York, 2018; Carruthers, Some Modern Methods of Organic Synthesis, $4^{th}$ Edition, Cambridge University Press, Cambridge, 2004; the entire contents of each of which are incorporated herein by reference.

At various places in the present disclosure, linking substituents are described. It is specifically intended that each linking substituent includes both the forward and backward forms of the linking substituent. For example, —NR(CR'R")— includes both —NR(CR'R")— and —(CR'R")NR—. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical, which may be optionally substituted independently with one or more substituents described below. The term "$C_{i-j}$ alkyl" refers to an alkyl having i to j carbon atoms. In some embodiments, alkyl groups contain 1 to 10 carbon atoms. In some embodiments, alkyl groups contain 1 to 9 carbon atoms. In some embodiments, alkyl groups contain 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-10}$ alkyl" include, but are not limited to, methyl, ethyl, propyl, butyl, pentyl, hexyl, heptyl, octyl, nonyl, and decyl. Examples of "$C_{1-6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl (allyl), butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "amide" refers to —C(═O)NR'—, wherein R' represents hydrogen, an N-protecting group, alkyl, alkenyl, alkynyl, alkoxy, cycloalkyl, heterocyclyl, aryl, heteroaryl and other suitable organic groups.

As used herein, the term "amine" refers to derivatives of ammonia, wherein one or more hydrogen atoms are replaced by a substituent, and can be represented by $N(H)_n(R')_{3-n}$ wherein n is 0, 1, or 2, and each R' is independently hydroxyl, nitro, an N-protecting group, alkyl, alkenyl, alkynyl, alkoxy, cycloalkyl, heterocyclyl, aryl, heteroaryl and other suitable organic groups, or two R' together with the nitrogen atom to which they are attached form an optionally substituted heterocyclyl or heteroaryl.

As used herein, the term "amino" refers to $—NH_2$.

As used herein, the term "acetal" refers to —O—CH(R')—O—, wherein R' represents alkyl, alkenyl, alkynyl, alkoxy, cycloalkyl, heterocyclyl, aryl, heteroaryl and other suitable organic groups.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups can be substituted at one or more ring positions with substituents as described above.

As used herein, the term "cycloalkyl", whether as part of another term or used independently, refer to a monovalent non-aromatic, saturated or partially unsaturated monocyclic and polycyclic ring system, in which all the ring atoms are carbon and which contains at least three ring forming carbon atoms. In some embodiments, the cycloalkyl may contain 3 to 12 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 4 to 12 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be substituted. In some embodiments, the cycloalkyl group may be a saturated cyclic alkyl group. In some embodiments, the cycloalkyl group may be a partially unsaturated cyclic alkyl group that contains at least one double bond or triple bond in its ring system. In some embodiments, the cycloalkyl group may be monocyclic or polycyclic. Examples of monocyclic cycloalkyl group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Examples of polycyclic cycloalkyl group include, but are not limited to, adamantyl, norbornyl, fluorenyl, spiro-pentadienyl, spiro[3.6]-decanyl, bicyclo[1,1,1]pentenyl, bicyclo[2,2,1]heptenyl, and the like.

As used herein, the term "carboxylate" or "carboxylate ester" refers to —C(═O)O—.

As used herein, the term "phosphate ester" refers to —OP(═O)(OR')O—, wherein R' represents hydrogen, an N-protecting group, alkyl, alkenyl, alkynyl, alkoxy, cycloalkyl, heterocyclyl, aryl, heteroaryl and other suitable organic groups As used herein, the term "carbamate" refers to —NR'(C═O)O—, wherein R' represents hydrogen, an N-protecting group, alkyl, alkenyl, alkynyl, alkoxy, cycloalkyl, heterocyclyl, aryl, heteroaryl and other suitable organic groups.

As used herein, the term "thiocarbamate" refers to —NR'(C═S)O—, wherein R' represents hydrogen, an N-protecting group, alkyl, alkenyl, alkynyl, alkoxy, cycloalkyl, heterocyclyl, aryl, heteroaryl and other suitable organic groups.

As used herein, the term "carbonate" refers to —OC(═O)O—.

As used herein, the term "thiocarbonate" refers to —OC(═S)O—.

As used herein, the term "heteroatom" refers to nitrogen, oxygen, or sulfur, and includes any oxidized form of nitrogen or sulfur, and any quaternized form of a basic nitrogen (including N-oxides).

As used herein, the term "heteroaryl", whether as part of another term or used independently, refers to an aryl group having, in addition to carbon atoms, one or more heteroatoms. The heteroaryl group can be monocyclic. Examples of monocyclic heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl group also includes polycyclic groups in which a heteroaromatic ring is fused to one or more aryl, cycloaliphatic, or heterocyclyl rings, where the radical or point of attachment is on the heteroaromatic ring. Examples of polycyclic heteroaryl include, but are not limited to, indolyl, isoindolyl, benzothienyl, benzofuranyl, benzo[1,3]dioxolyl, dibenzofuranyl, indazolyl, benzimidazolyl, benzthiazolyl, quinolyl, isoquinolyl, dihydroquinolinyl, dihydroisoquinolinyl, tetrahydroquinolinyl, tetrahydroisoquinolinyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and the like.

As used herein, the term "heterocyclyl" refers to a saturated or partially unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substituents. In some embodiments, the heterocyclyl is a saturated heterocyclyl. In some embodiments, the heterocyclyl is a partially unsaturated heterocyclyl having one or more double bonds in its ring system. In some embodiments, the heterocyclyl may contains any oxidized form of carbon, nitrogen or sulfur, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, piperidinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, tetrahydroquinolinyl, tetrahydroisoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "hydrazone" refers to —C(R')═N—NH—, wherein R' represents hydrogen, alkyl, alkenyl, alkynyl, alkoxy, cycloalkyl, heterocyclyl, aryl, heteroaryl and other suitable organic groups.

As used herein, the term "hydroxyl" refers to —OH.

As used herein, the term "ketone" refers to —C(═O)—.

As used herein, the term "phosphonamidate" refers to —OP(═O)(R')(NR")—, wherein R' and R" are independently hydrogen, alkyl, alkenyl, alkynyl, alkoxy, cycloalkyl, heterocyclyl, aryl, heteroaryl and other suitable organic groups.

As used herein, the term "imine" refers to —C(R')═N—, wherein R' represents hydrogen, alkyl, alkenyl, alkynyl, alkoxy, cycloalkyl, heterocyclyl, aryl, heteroaryl and other suitable organic groups.

As used herein, the term "linkage" or "linker" refers to bonds or chemical moiety formed from a chemical reaction between the functional groups of at least two entities to be linked, thereby forming one molecule or maintaining association of the entities in sufficiently close proximity. A linkage can be integrated in the resulting linked molecule or structure, with or without its reacted functional groups. Such linkages may be covalent or non-covalent. Hydrolytically unstable or degradable linkages mean that the linkages are degradable in water or in aqueous solutions, including for example, body fluid such as blood. Enzymatically unstable or degradable linkages mean that the linkage can be degraded by one or more enzymes. Such degradable linkages include, but are not limited to ester linkages formed by the carboxylic acid in one entity with alcohol groups on a biologically active agent, wherein such ester groups generally hydrolyze under physiological conditions to release the biologically active agent. Other hydrolytically degradable linkages include but are not limited to carbonate linkages, imine linkages resulted from reaction of an amine and an aldehyde, phosphate ester linkages resulted from reaction of a phosphate group and an alcohol, hydrazone linkages resulted from reaction of a hydrazide and an aldehyde, acetal linkages resulted from reaction of an aldehyde and an alcohol, amide linkages resulted from reaction of an amine group and a carboxyl group.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "pharmaceutically acceptable" indicates that the substance or composition is compatible chemically and/or toxicologically, with the other ingredients comprising a formulation, and/or the subjects being treated therewith.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

As used herein, the terms "therapeutic agent", "drug", "biologically active molecule", "biologically active agent", "active agent" and the like refer to any substance which can affect any physical or biochemical properties of a biological organism, including but not limited to viruses, bacteria, fungi, plants, animals, and human. In particular, as used herein, therapeutic agents include any substance intended for diagnosis, cure, mitigation, treatment, or prevention of disease in humans or other animals, or to otherwise enhance physical or mental well-being of humans or animals.

Drug delivery of therapeutic agents to specific tissues or sites within a body presents a variety of challenges, particularly where local delivery of a therapeutic agent to a specific tissue and sustained release of the therapeutic agent are desired, and where avoidance of high systemic concentration of the therapeutic agent leading to toxic side effects is desired.

Compound

Therefore, the present disclosure provides a prodrug compound capable of locally delivering a therapeutic agent and releasing the therapeutic agent in a controlled and sustained manner with reduced systemic side effect. This is achieved by deliberately designing a prodrug compound which achieves a balance of solubility of the prodrug compound and the rate of the prodrug compound for releasing the parent drug.

In one aspect, the present disclosure provides a prodrug compound comprising a parent drug moiety and a tail moiety, wherein

- the parent drug moiety is derived from a parent drug comprising a reactive group selected from the group consisting of amine, amino, hydroxyl, and amide,
- the tail moiety is covalently linked to the parent drug moiety and has a Formula (I):

(I)

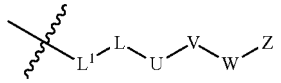

wherein:

- $L^1$ is connected to the parent drug moiety through the reactive group of the parent drug to form a cleavable linkage;
- L is a direct bond or alkyl;
- U is selected from the group consisting of a direct bond, cycloalkyl, heterocyclyl, aryl and heteroaryl;
- V is a direct bond or alkyl;
- W is selected from the group consisting of a direct bond, cycloalkyl, heterocyclyl, aryl and heteroaryl;
- Z is selected from the group consisting of a direct bond, alkyl, aryl, $NR^1R^2$, and $OR^3$, wherein said alkyl and aryl are optionally substituted with one or more $R^4$;
- $R^1$, $R^2$ and $R^3$ are independently hydrogen, alkyl or cycloalkyl; and
- $R^4$ is selected from the group consisting of alkyl, cycloalkyl, heterocyclyl, aryl and heteroaryl,
- provided that when U is not a direct bond, V, W and Z are not direct bonds at the same time, or a pharmaceutically acceptable salt thereof.

In some embodiments, the parent drug comprises at least one reactive group, which is capable of reacting with a reactive functional group of a second entity (e.g., the tail moiety provided herein) and an optional co-reactant to form a cleavable linkage, thereby linking the parent drug moiety to the second entity (e.g., the tail moiety).

A "cleavable linkage" is a relatively labile bond that cleaves under physiological conditions. An exemplary releasable linkage is a hydrolyzable bond that cleaves upon reaction with water (i.e., is hydrolyzed). The tendency of a bond to hydrolyze in water may depend not only on the general type of linkage connecting two atoms but also on the substituents attached to these atoms. Appropriate hydrolytically unstable or weak linkages include but are not limited to carboxylate ester, phosphate ester, anhydrides, acetals, ketals, amide, acyloxyalkyl ether, imines, hydrazone, orthoesters, peptides, oligonucleotides, thioesters, urea, thiourea, carbamate, thiocabamate, phosphoramidate, phosphonamidate, carbonates and thiocarbonate. Certain functional groups have atoms that may be chemically degraded by a process other than hydrolysis. Exemplary releasable linkages in this category include certain carbamates and Fmoc derivatives. Certain molecules containing these kinds of functionalities appropriately bonded may undergo chemical degradation (release) upon action of a base. In such cases "cleave" may occur at higher values of pH or through the action of biological molecules that contain basic moieties (e.g. histidines). Another exemplary cleavable linkage is an enzymatically cleavable linkage. An "enzymatically cleavable linkage" means a linkage that is subject to cleavage by one or more enzymes.

In certain embodiments, the parent drug is selected from the group consisting of anti-cancer agent, anti-inflammatory drugs, antibiotics, anti-fugus agent, JAK inhibitors, and VEGF inhibitors.

In some embodiments, the parent drug is an anti-cancer agent.

In some embodiments, the parent drug is an anti-inflammatory drug.

In some embodiments, the parent drug is an antibiotic.

In some embodiments, the parent drug is an anti-fugus agent.

In some embodiments, the parent drug is selected from the group consisting of Fluorouracil, Temozolomide, Daunorubicin, 10-hydroxyl-camptothecine, and 7-ethyl-10-hydroxyl-camptothecine.

In some embodiments, the reactive group of the parent drug reacts with the reactive functional group of the tail moiety and an optional co-reactant to form a cleavable linkage selected from the group consisting of carbonate, thiocarbonate, carbamate, thiocarbamate, carboxylate ester, phosphate ester, amide, imine, hydrazone, phosphonamidate and acetal.

In some embodiments, $L^1$ is selected from a direct bond, *—$CH_2OC(=O)O$—, *—$CH_2OC(=S)O$—, *—C(=O)O—, *—OC(=S)—, *—C(=O)—, *—C(=O)N($R^a$)—, *—C(=S)N($R^a$)—, *—$CH_2OP(=O)(R^a)O$—, and *—P(=O)($R^a$)N($R^a$)—, wherein $R^a$ is hydrogen, alkyl, alkenyl or alkynyl, and the* end of $L^1$ is connected to the parent drug moiety.

In some embodiments, $L^1$ is selected from the group consisting of a direct bond, *—$CH_2OC(=O)O$—, *—C(=O)O—, *—C(=O)—, *—C(=O)N($R^a$)—, *—$CH_2OP(=O)(R^a)O$—, and *—P(=O)($R^a$)N($R^a$)—.

In some embodiments, the parent drug comprises amine group which reacts with a reactive functional group of the tail moiety and an optional co-reactant, such that $L^1$ selected from *—$CH_2OC(=O)O$—, *—C(=O)O—, *—C(=O)—, and *—$CH_2OP(=O)(R^a)O$— is formed.

In some embodiments, the parent drug comprises amino group which reacts with a reactive functional group of the tail moiety and an optional co-reactant, such that $L^1$ selected from a direct bond and *—C(=O)O— is formed.

In some embodiments, the parent drug comprises hydroxyl group which reacts with a reactive functional group of the tail moiety and an optional co-reactant, such that $L^1$ selected from *—C(=O)—, *—C(=O)O—, *—C(=O)N($R^a$)— and *—P(=O)($R^a$)N($R^a$)— is formed.

In some embodiments, L is a direct bond.

In some embodiments, L is alkyl. In certain embodiments, L is $C_{1-6}$ alkyl, $C_{1-5}$ alkyl, $C_{1-4}$ alkyl, $C_{1-3}$ alkyl, or $C_{1-2}$ alkyl.

In certain embodiments, L is methyl, ethyl or hexyl.

In some embodiments, U is a direct bond.

In some embodiments, U is heterocyclyl. In certain embodiments, U is saturated heterocyclyl. In certain embodiments, U is partially unsaturated heterocyclyl.

In certain embodiments, U is 5- to 12-membered heterocyclyl, 5- to 11-membered heterocyclyl, 5- to 10-membered heterocyclyl, 5- to 9-membered heterocyclyl, 5- to 8-membered heterocyclyl, 5- to 7-membered heterocyclyl or 5- to 6-membered heterocyclyl.

In certain embodiments, U is 5- to 12-membered saturated heterocyclyl, 5- to 11-membered saturated heterocyclyl, 5- to 10-membered saturated heterocyclyl, 5- to 9-membered saturated heterocyclyl, 5- to 8-membered saturated heterocyclyl, 5- to 7-membered heterocyclyl or 5- to 6-membered saturated heterocyclyl.

In certain embodiments, U is piperidinyl.

In certain embodiments, U is 5- to 12-membered partially unsaturated heterocyclyl, 5- to 11-membered partially unsaturated heterocyclyl, 5- to 10-membered partially unsaturated heterocyclyl, 5- to 9-membered partially unsaturated heterocyclyl, 5- to 8-membered partially unsaturated heterocyclyl, 5- to 7-membered heterocyclyl or 5- to 6-membered partially unsaturated heterocyclyl.

In certain embodiments, U is 1,2,3,4-tetrahydro-isoquinolinyl.

In some embodiments, U is aryl. In certain embodiments, U is 5 to 12 membered aryl, 5 to 10 membered aryl, 5 to 8 membered aryl, or 5 to 6 membered aryl.

In certain embodiments, U is phenyl.

In some embodiments, L is a direct bond, and U is a direct bond, heterocyclyl or aryl.

In certain embodiments, L is a direct bond, and U is a direct bond, 5- to 12-membered saturated or partially unsaturated heterocyclyl, or 5 to 12 membered aryl.

In certain embodiments, L is a direct bond, and U is selected from the group consisting of a direct bond, 1,2,3,4-tetrahydro-isoquinolinyl and phenyl.

In some embodiments, L is alkyl, and U is a direct bond, heterocyclyl or aryl.

In certain embodiments, L is $C_{1-6}$ alkyl, and U is a direct bond, 5- to 12-membered saturated or partially unsaturated heterocyclyl, or 5 to 12 membered aryl.

In certain embodiments, L is $C_{1-6}$ alkyl, and U is selected from the group consisting of a direct bond, piperidinyl and phenyl.

In some embodiments, V is a direct bond.

In some embodiments, V is alkyl. In certain embodiments, V is $C_{1-6}$ alkyl, $C_{1-5}$ alkyl, $C_{1-4}$ alkyl, $C_{1-3}$ alkyl, or $C_{1-2}$ alkyl.

In certain embodiments, V is methyl.

In some embodiments, W is a direct bond.

In some embodiments, W is aryl. In certain embodiments, W is 5 to 12 membered aryl, 5 to 10 membered aryl, 5 to 8 membered aryl, or 5 to 6 membered aryl.

In certain embodiments, W is phenyl.

In some embodiments, W is heterocyclyl. In certain embodiments, W is saturated heterocyclyl. In certain embodiments, W is partially unsaturated heterocyclyl.

In certain embodiments, W is 5- to 12-membered heterocyclyl, 5- to 11-membered heterocyclyl, 5- to 10-membered heterocyclyl, 5- to 9-membered heterocyclyl, 5- to 8-membered heterocyclyl, 5- to 7-membered heterocyclyl or 5- to 6-membered heterocyclyl.

In certain embodiments, W is 5- to 12-membered saturated heterocyclyl, 5- to 11-membered saturated heterocyclyl, 5- to 10-membered saturated heterocyclyl, 5- to 9-membered saturated heterocyclyl, 5- to 8-membered saturated heterocyclyl, 5- to 7-membered heterocyclyl or 5- to 6-membered saturated heterocyclyl.

In certain embodiments, W is pyrrolidinyl, piperidinyl or piperazinyl.

In some embodiments, Z is a direct bond.

In some embodiments, Z is alkyl optionally substituted with one or more $R^4$. In certain embodiments, Z is $C_{1-8}$ alkyl optionally substituted with one or more $R^4$.

In certain embodiments, $R^4$ is cycloalkyl or aryl.

In certain embodiments, Z is $C_{1-8}$ alkyl.

In certain embodiments, Z is $C_{1-6}$ alkyl, $C_{1-5}$ alkyl, $C_{1-4}$ alkyl, $C_{1-3}$ alkyl or $C_{1-2}$ alkyl, each of which is substituted with one or two $R^4$, and $R^4$ is independently cycloalkyl or aryl.

In certain embodiments, Z is methyl or ethyl, which is substituted with one or two $R^4$, and $R^4$ is independently adamantyl or phenyl.

In some embodiments, Z is aryl optionally substituted with one or more $R^4$. In certain embodiments, Z is 5- to 12-membered aryl optionally substituted with one or more $R^4$.

In certain embodiments, $R^4$ is alkyl.

In certain embodiments, Z is phenyl optionally substituted with one or more $R^4$, wherein $R^4$ is $C_{1-6}$ alkyl, $C_{1-5}$ alkyl, $C_{1-4}$ alkyl, $C_{1-3}$ alkyl, or $C_{1-2}$ alkyl.

In certain embodiments, Z is phenyl substituted with one or more $R^4$, wherein $R^4$ is methyl or ethyl.

In some embodiments, Z is $NR^1R^2$.

In certain embodiments, $R^1$ and $R^2$ are independently alkyl or cycloalkyl.

In certain embodiments, $R^1$ and $R^2$ are independently $C_{1-6}$ alkyl, $C_{1-5}$ alkyl, $C_{1-4}$ alkyl, $C_{1-3}$ alkyl, or $C_{1-2}$ alkyl.

In certain embodiments, $R^1$ and $R^2$ are independently $C_{3-6}$ cycloalkyl.

In some embodiments, Z is $OR^3$.

In certain embodiments, $R^3$ is alkyl. In certain embodiments, $R^3$ is $C_{1-6}$ alkyl, $C_{1-5}$ alkyl, $C_{1-4}$ alkyl, $C_{1-3}$ alkyl, or $C_{1-2}$ alkyl. In certain embodiments, $R^3$ is methyl.

In some embodiments, the present disclosure provides a prodrug compound having a formula selected from the group consisting of:

(II)

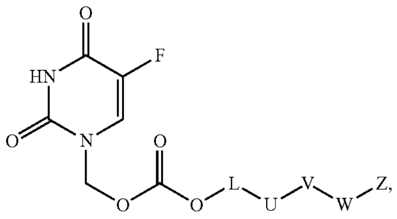

(III)

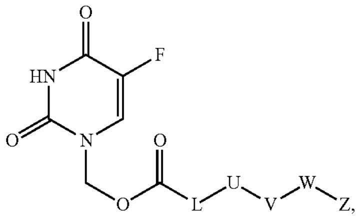

(IV)

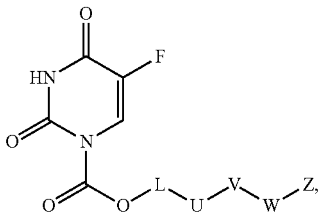

(V)

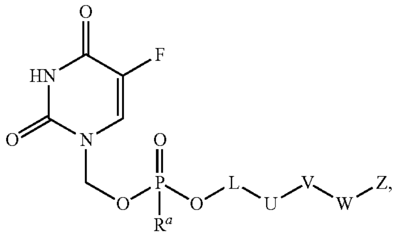

or a pharmaceutically acceptable salt thereof, wherein L, U, V, W, Z and $R^a$ are defined as supra.

In certain embodiments, in prodrug compound having a Formula (II), (III), (IV) or (V), L is a direct bond, U is heterocyclyl, aryl or heteroaryl, V is a direct bond or alkyl, W is a direct bond, heterocyclyl or aryl;

Z is alkyl, aryl, $NR^1R^2$, or $OR^3$, wherein said alkyl and aryl are optionally substituted with one or more $R^4$, wherein $R^1$, $R^2$, $R^3$ and $R^4$ are defined as supra.

In some embodiments, the present disclosure provides a prodrug compound having a formula selected from the group consisting of:

(VI)

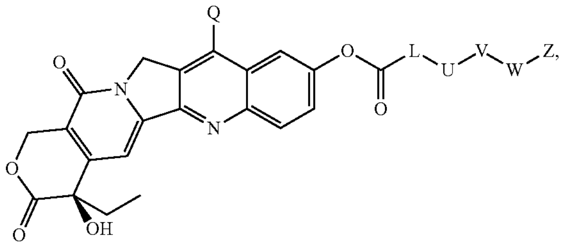

(VII)

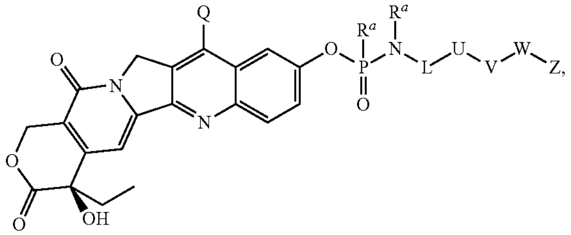

(VIII)

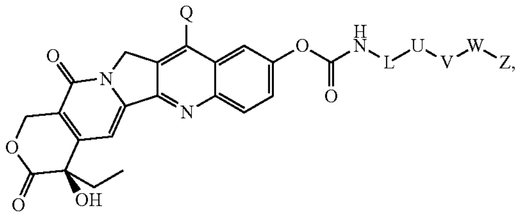

and (IX)

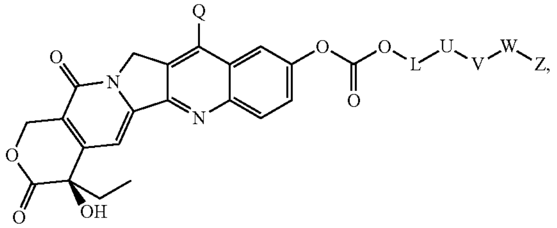

or a pharmaceutically acceptable salt thereof, wherein Q is hydrogen or ethyl, and L, U, V, W, Z and $R^a$ are as defined as supra.

In certain embodiments, in prodrug compound having a Formula (VI), (VII), (VIII) or (IX), L is a direct bond or alkyl, U is a direct or aryl, V is a direct bond, W is a direct bond or heterocyclyl;

Z is $NR^1R^2$ or alkyl optionally substituted with one or more $R^4$.

wherein $R^1$, $R^2$ and $R^4$ are defined as supra.

In some embodiments, the present disclosure provides a prodrug compound having a formula of:

(X)

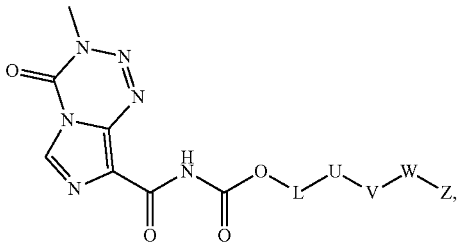

or (XI)

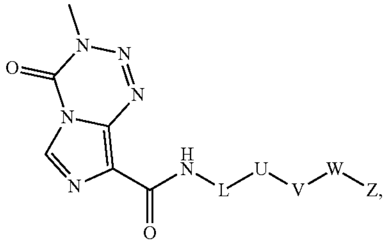

or a pharmaceutically acceptable salt thereof, wherein L, U, V, W, and Z are as defined as supra.

In some embodiments, the present disclosure provides a prodrug compound having a formula of:

(XII)

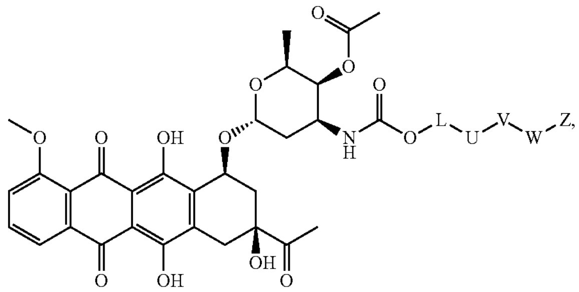

or a pharmaceutically acceptable salt thereof, wherein L, U, V, W, and Z are as defined as supra.

In some embodiments, the prodrug compound provided herein has a lower solubility than the parent drug at biological pH.

In some embodiments, the present disclosure provides a prodrug compound selected from the group consisting of:

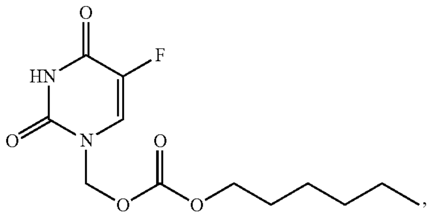

-continued

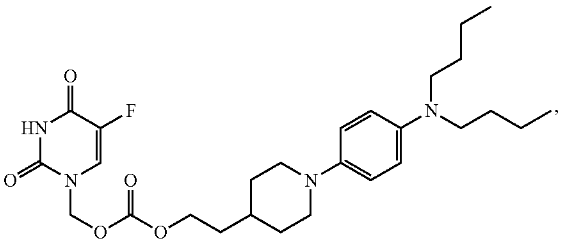

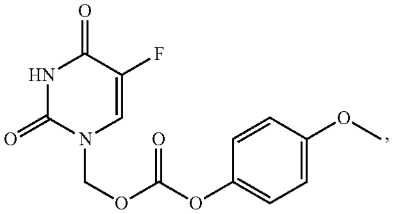

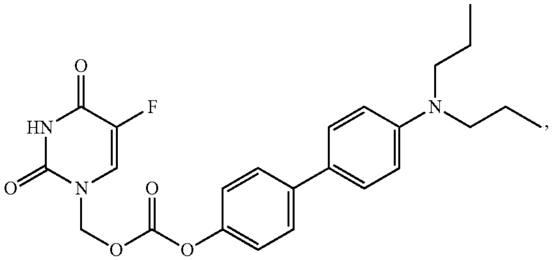

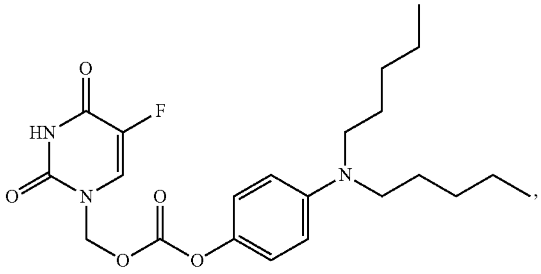

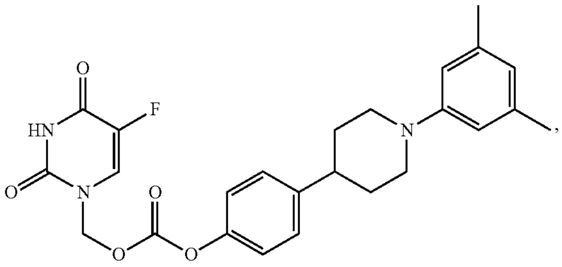

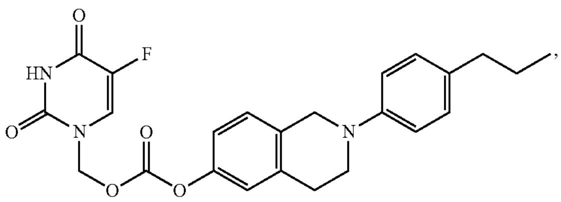

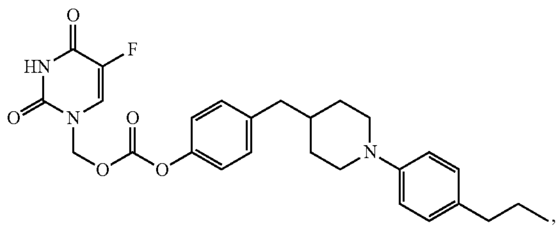

-continued
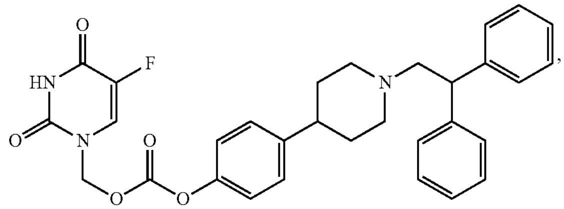,
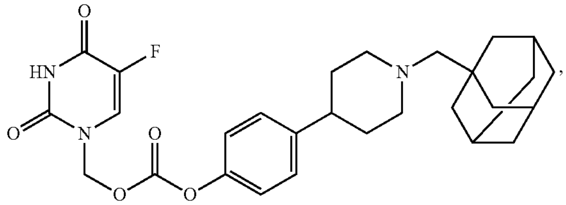,
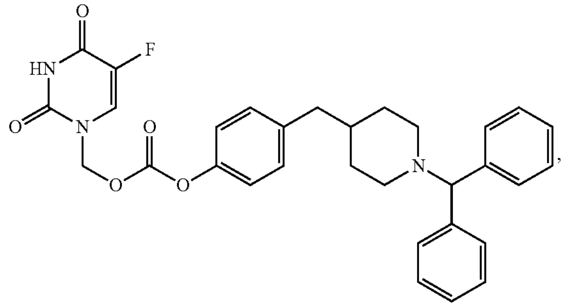,
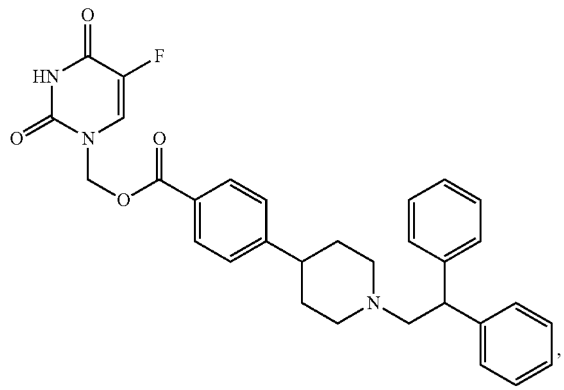,
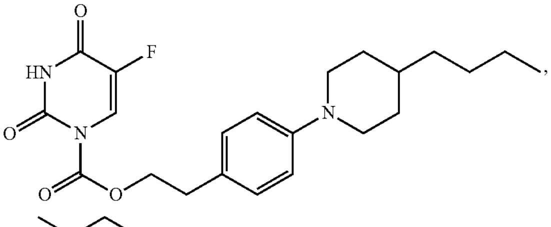,
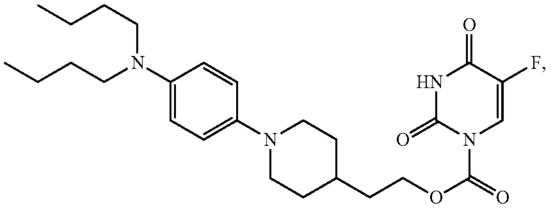
-continued
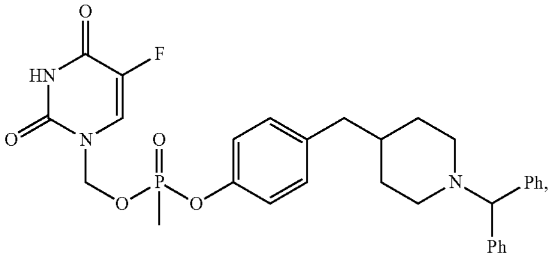
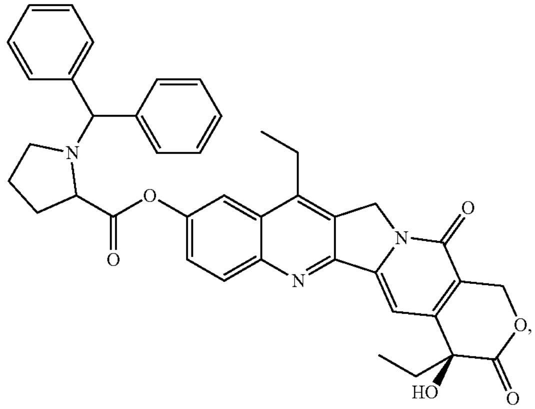
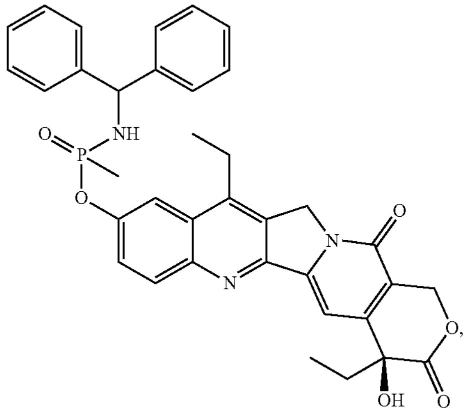
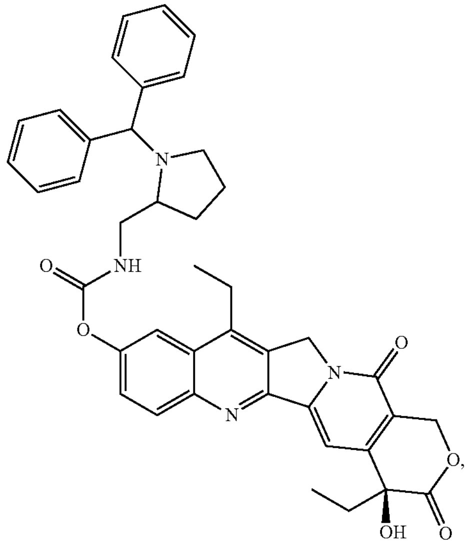

-continued

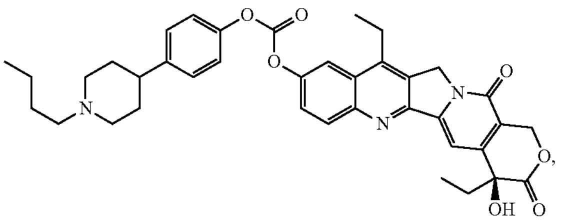

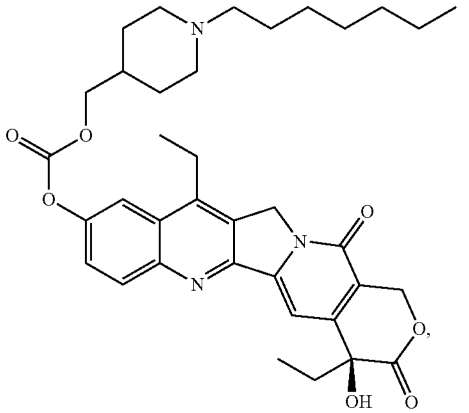

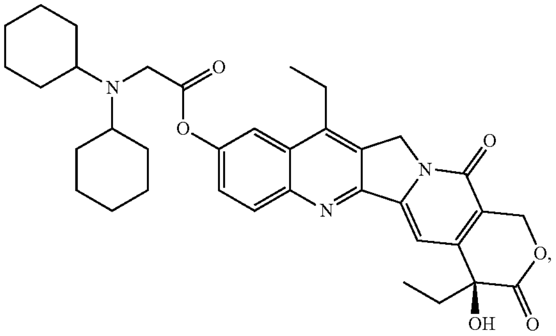

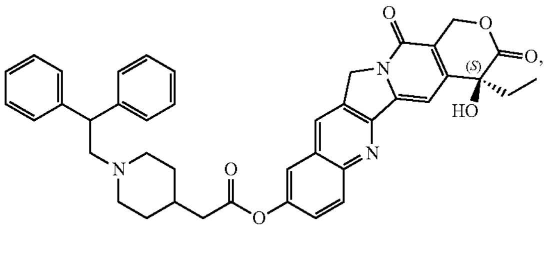

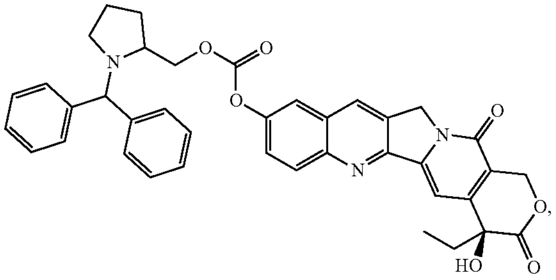

-continued

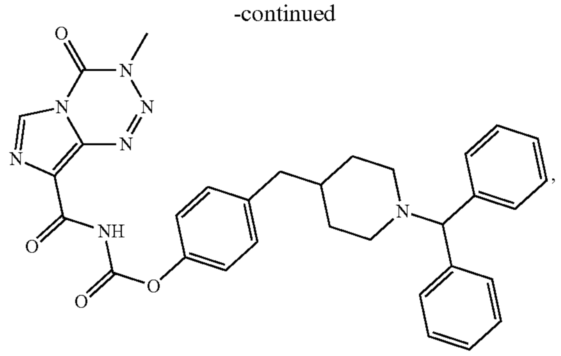

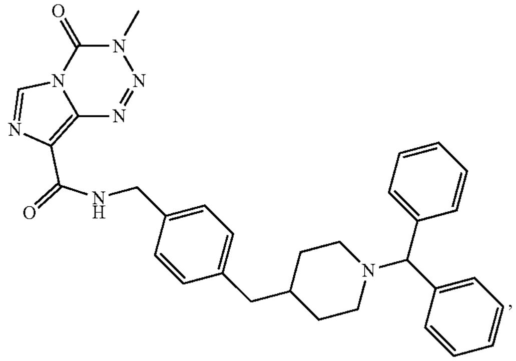

, and

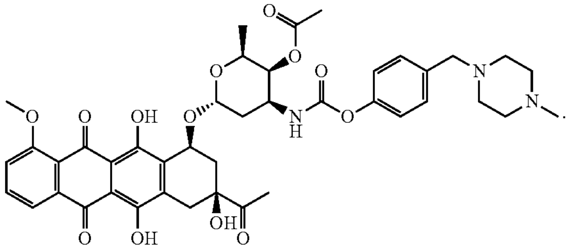

The prodrug compounds provided herein are described with reference to both generic formulae and specific compounds. In addition, the prodrug compounds of the present disclosure may exist in a number of different forms or derivatives, all within the scope of the present disclosure. These include, for example, tautomers, stereoisomers, racemic mixtures, regioisomers, salts, solvated forms, amorphous forms, different crystal forms or polymorphs.

The prodrug compounds of present disclosure can comprise one or more asymmetric centers depending on substituent selection, and thus can exist in various stereoisomeric forms, e.g., enantiomers and/or diastereomers. For example, the prodrug compounds provided herein may have an asymmetric carbon center, and thus compounds provided herein may have either the (R) or (S) stereo-configuration at a carbon asymmetric center. Therefore, the prodrug compounds of the present disclosure may be in the form of an individual enantiomer, diastereomer or geometric isomer, or may be in the form of a mixture of stereoisomers.

As used herein, the term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound provided herein or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972).

In some embodiments, mixtures of diastereomers, for example mixtures of diastereomers enriched with 51% or more of one of the diastereomers, including for example 60% or more, 70% or more, 80% or more, or 90% or more of one of the diastereomers are provided.

The present disclosure additionally encompasses the compounds as individual isomers substantially free of other isomers and alternatively, as mixtures of various isomers, e.g., racemic mixtures of enantiomers.

The prodrug compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulfur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen includes protium, deuterium and tritium. In some embodiments, carbon includes $^{12}C$ and $^{13}C$. Isotopically-enriched compounds of Formula (I) can be prepared without undue experimentation by conventional techniques well known to those skilled in the art or by processes analogous to those described in the Schemes and Examples herein using appropriate isotopically-enriched reagents and/or intermediates.

The prodrug compounds of the present disclosure can be formulated as or be in the form of pharmaceutically acceptable salts. Unless specified to the contrary, a prodrug compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, PA, Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. Examples of solvents that form solvates include, but are not limited to, water, isopropanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulfur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen includes protium, deuterium and tritium. In some embodiments, carbon includes $^{12}C$ and $^{13}C$.

Synthesis of Compound

Synthesis of the prodrug compounds provided herein is illustrated in the synthetic schemes in the examples. The prodrug compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the schemes are for better illustration and can be changed as appropriate. The embodiments of the prodrug compounds in examples were synthesized for the purposes of research and potentially submission to regulatory agencies.

The reactions for preparing the prodrug compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of the prodrug compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), in P. Kocienski, Protecting Groups, Georg Thieme Verlag, 2003, and in Peter G. M. Wuts, Greene's Protective Groups in Organic Synthesis, 5$^{th}$ Edition, Wiley, 2014, all of which are incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The known starting materials of the present disclosure can be synthesized by using or according to the known methods in the art, or can be purchased from commercial suppliers. Unless otherwise noted, analytical grade solvents and commercially available reagents were used without further purification.

Unless otherwise specified, the reactions of the present disclosure were all done under a positive pressure of nitrogen or argon or with a drying tube in anhydrous solvents, and the reaction flasks were typically fitted with rubber septa for the introduction of substrates and reagents via syringe. Glassware was oven dried and/or heat dried.

Use of Compounds

In an aspect, the present disclosure provides a prodrug compound capable of locally delivering a therapeutic agent and releasing the therapeutic agent in a controlled and sustained manner with reduced systemic exposure and potential side effect due to systemic exposure. Thus, the prodrug compound of the present disclosure or a pharmaceutically acceptable salt thereof are useful as therapeutic or prophylactic agent for various diseases, depending on the parent drug selected to be released.

As used herein, the term "therapy" is intended to have its normal meaning of dealing with a disease in order to entirely or partially relieve one, some or all of its symptoms, or to correct or compensate for the underlying pathology, thereby achieving beneficial or desired clinical results. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Therapy" can also mean prolonging survival as compared to expected survival if not receiving it. Those in need of therapy include those already with the condition or disorder as well as those prone to have the condition or disorder or those in which the condition or disorder is to be prevented. The term "therapy" also encompasses prophylaxis unless there are specific indications to the contrary. The terms "therapeutic" and "therapeutically" should be interpreted in a corresponding manner.

The term "treatment" is used synonymously with "therapy". Similarly the term "treat" can be regarded as "applying therapy" where "therapy" is as defined herein.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The prodrug compound of the present disclosure or a pharmaceutically acceptable salt thereof shows a desired overall release rate of parent drug by controlling its solubility at a biological pH and the release of parent drug at different pHs.

In some embodiments, the prodrug compound of the present disclosure or a pharmaceutically acceptable salt thereof has a lower solubility than the parent drug at a biological pH.

In certain embodiments, the prodrug compound of the present disclosure or a pharmaceutically acceptable salt thereof shows a solubility at acidic pH that is higher than that at biological pH. In some embodiments, the ratio of the solubility of the prodrug compound of the present disclosure or a pharmaceutically acceptable salt thereof at acidic pH to that at biological pH is greater than 5, greater than 10, greater than 20, greater than 30, greater than 40, greater than 50, greater than 60, greater than 70, greater than 80, greater than 90, greater than 100, greater than 200, greater than 300, greater than 400, greater than 500, greater than 600, greater than 700, greater than 800, greater than 900, greater than 1000, greater than 1100, greater than 1200, greater than 1300, greater than 1400, greater than 1500 or even higher.

The reduced solubility of the prodrug compounds provided herein may avoid the high local concentration after administration, thereby providing a solubility controlled zero order sustained release mechanism.

The parent drug may be released from the prodrug compound provided herein through the cleavage of the linkage between the parent drug moiety and the tail moiety. The release of the parent drug may involve enzymatic or non-enzymatic processes. In some embodiments, the parent drug is released from the prodrug compound provided herein via hydrolysis process.

The release of the parent drug may be affected by a variety of factors, for example, the selection of specific parent drug, the linkage between the parent drug moiety and tail moiety, the tail moiety, and the administration of the prodrug compound (for example, administration site, administration route). The present disclosure contemplates parent drugs with varying reactive groups and linkages with the tail moiety.

The present disclosure also contemplates varying administration of the prodrug compounds provided herein. In some embodiments, the prodrug compounds provided herein is locally administered to a subject in need thereof. In certain embodiments, the prodrug compounds provided herein is locally administered to a subject in need thereof via injection. In certain embodiments, the prodrug compounds provided herein is locally administered to a subject in need thereof via oral dosage form. In certain embodiments, the prodrug compounds provided herein is locally administered to a subject in need thereof via inhalation. In certain embodiments, the prodrug compounds provided herein is locally administered to a subject in need thereof via implant. In certain embodiments, the prodrug compounds provided herein is locally administered to a subject in need thereof via topical application. Depending on the specific parent drug, cleavable linkage and tail moiety combination, release of parent drug may occur in a variety of locations upon administration to a subject.

In some embodiments, the prodrug compounds provided herein or a pharmaceutically acceptable salt thereof may release the parent drugs via hydrolysis at different rates.

In some embodiments, the release rate of the parent drug from the prodrug compound provided herein or a pharmaceutically acceptable salt thereof may be characterized by the percent of the parent drug released from the prodrug compound at pH 7.4 in 6 hours after administration. In some embodiments, at pH 7.4, the release rate of the parent drug from the prodrug compound may vary in a range of about 50% to about 100% in 6 hours after administration, for example, about 55% to about 100%, about 60% to about 100%, about 65% to about 100%, about 70% to about 100%, about 75% to about 100%, about 80% to about 100%, about 85% to about 100%, about 90% to about 100%, about 95% to about 100%, about 96% to about 100%, about 97% to about 100%, about 98% to about 100%, about 99% to about 100%, or even about 100%.

In some embodiments, the release rate of the parent drug from the prodrug compound provided herein or a pharmaceutically acceptable salt thereof may be characterized by the percent of the parent drug released from the prodrug compound at pH 7.4 in 0.5 hours after administration. In some embodiments, at pH 7.4, the release rate of the parent drug from the prodrug compound may vary in a range of about 5% to about 100% in 0.5 hours after administration, for example, about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 95% to about 100%, about 96% to about 100%, about 97% to about 100%, about 98% to about 100%, about 99% to about 100%, or even about 100%.

In some embodiments, at pH 2.0, the release rate of the parent drug from the prodrug compound is not greater than 70% in 6 hours after administration, for example, not greater than 65%, not greater than 60%, not greater than 55%, not greater than 50%, not greater than 45%, not greater than 40%, not greater than 35%, not greater than 30%, not greater than 25%, not greater than 20%, not greater than 15%, not greater than 10%, not greater than 5%, not greater than 4%, not greater than 3%, not greater than 2%, or not greater than 1%. In certain embodiments, at pH 2.0, the prodrug compound provided herein remains stable without releasing the parent drug via hydrolysis.

In some embodiments, the release rate of the parent drug from the prodrug compound provided herein or a pharmaceutically acceptable salt thereof may be characterized by the hydrolysis constant ($K_h$) of the prodrug compound in 6 hours after administration. In some embodiments, at pH 7.4, the prodrug compound provided herein may have a $K_h$ value in a range of about 0.1 to about 15, for example, about 0.1 to about 14, about 0.1 to about 13, about 0.1 to about 12, about 0.1 to about 11, about 0.1 to about 10, about 0.1 to about 9, about 0.1 to about 8, about 0.1 to about 7, about 0.1 to about 6, about 0.1 to about 5, about 0.1 to about 4, about 0.1 to about 3, about 0.1 to about 2, about 0.1 to about 1, about 0.1 to about 0.5, about 0.1 to about 0.4, about 0.1 to about 0.3, or about 0.1 to about 0.2.

In some embodiments, at pH 2.0, the prodrug compound provided herein may have a $K_h$ value not greater than 0.2, for example, not greater than not greater than 0.15, not greater than 0.1, not greater than 0.09, not greater than 0.08, not greater than 0.07, not greater than 0.06, not greater than 0.05, not greater than 0.04, not greater than 0.03, not greater than 0.02, or not greater than 0.01. In certain embodiments, the prodrug compound provided herein may have a $K_h$ value of 0.

In some embodiments, the prodrug compound provided herein release more parent drug in 6 hours after administration at pH 7.4 than at pH 2.0.

In certain embodiments, the ratio of the percent of the parent drug released from the prodrug compound provided herein in 6 hours after administration at pH 7.4 to that at pH 2.0 is greater than 1, for example, greater than 1.1, greater than 1.2, greater than 1.3, greater than 1.4, greater than 1.5, greater than 2, great than 2.5, greater than 3, greater than 3.5, greater than 4, greater than 4.5, greater than 5, greater than 5.5, greater than 6, greater than 7, greater than 8, greater than 9, greater than 10, and the like.

In certain embodiments, the ratio of $K_h$ value of the prodrug compound provided herein at pH 7.4 to that at pH 2.0 is greater than 1, for example, greater than 1.5, greater than 2, greater than 3, greater than 4, greater than 5, greater than 10, greater than 20, greater than 30, greater than 40, greater than 50, greater than 60, greater than 70, greater than 80, greater than 90, greater than 100, greater than 150, greater than 200, greater than 250, greater than 300, greater than 350, greater than 400, and the like.

By deliberately selecting suitable parent drug and the tail moiety to achieve the desired combination of solubility and release profile, the prodrug compound provided herein may provide sustained release of parent drug over a period of 1-12 hours.

Pharmaceutical Compositions

In a further aspect, there is provided pharmaceutical compositions comprising the prodrug compounds of the present disclosure.

In another aspect, there is provided pharmaceutical compositions comprising the prodrug compounds of the present disclosure, and at least one pharmaceutical acceptable excipient.

As used herein, the term "pharmaceutical composition" refers to a formulation containing the drug delivery system of the present disclosure in a form suitable for administration to a subject.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient. The term "pharmaceutically acceptable excipient" also encompasses "pharmaceutically acceptable carrier" and "pharmaceutically acceptable diluent".

The pharmaceutical compositions provided herein can be in any form that allows for the composition to be administered to a subject, including, but not limited to a human, and formulated to be compatible with an intended route of administration.

A variety of routes are contemplated for the pharmaceutical compositions provided herein, and accordingly the pharmaceutical composition provided herein may be supplied in bulk or in unit dosage form depending on the intended administration route. For example, for oral, buccal, and sublingual administration, powders, granules, tablets, pills, capsules, gelcaps, and caplets may be acceptable as solid dosage forms, and emulsions, syrups, elixirs, suspensions, and solutions may be acceptable as liquid dosage forms. For injection administration, gel, solutions, emulsions and suspensions may be acceptable as liquid dosage forms, and a powder suitable for reconstitution with an appropriate solution as solid dosage forms. For inhalation administration, solutions, sprays, dry powders, and aerosols may be acceptable dosage form. For topical (including buccal and sublingual) or transdermal administration, powders, sprays, ointments, pastes, creams, lotions, gels, solutions, and patches may be acceptable dosage form. For vaginal administration, pessaries, tampons, creams, gels, pastes, foams and spray may be acceptable dosage form. For implant administration, solid, semi-solid, gel may be acceptable dosage form.

In some embodiments, the pharmaceutical compositions of the present disclosure may be in a form of formulation for oral administration.

In some embodiments, the pharmaceutical compositions of the present disclosure may be in a form of formulation for injection administration.

In some embodiments, the pharmaceutical compositions of the present disclosure may be in a form of formulation for inhalation administration.

In some embodiments, the pharmaceutical compositions of the present disclosure may be in a form of formulation for topical administration.

In certain embodiments, the pharmaceutical compositions provided herein may be formulated in the form of skin patches that are well known to those of ordinary skill in the art.

Besides those representative dosage forms described above, pharmaceutically acceptable excipients and carriers are generally known to those skilled in the art and are thus included in the present disclosure. Such excipients and carriers are described, for example, in "Remingtons Pharmaceutical Sciences" Mack Pub. Co., New Jersey (1991), in "Remington: The Science and Practice of Pharmacy", Ed. University of the Sciences in Philadelphia, $21^{st}$ Edition, LWW (2005), which are incorporated herein by reference.

In some embodiments, the pharmaceutical compositions of the present disclosure can be formulated as a single dose. The amount of the prodrug compounds provided herein in the single dose will vary depending on the subject treated and particular mode of administration.

In some embodiments, the pharmaceutical compositions of the present disclosure can be formulated to be administered to a subject at a time interval of a few days, a few weeks, a few months or even longer.

In a further aspect, there is also provided pharmaceutical compositions comprise the drug delivery system of the present disclosure, as two or more combination therapy.

Method of Treatment of Disease

In a further aspect, there is provided a method of treating diseases in a subject in need thereof, comprising administering to the subject a therapeutic effective amount of the prodrug compound or the pharmaceutical composition provided herein.

The diseases to be treated depends on the selected parent drug in the prodrug or the pharmaceutical composition provided herein. In some embodiments, the disease can be selected from the group consisting of anal cancer, breast cancer, colorectal cancer, esophageal cancer, pancreatic cancer, head and neck cancer, brain cancer, liver cancer, gastric cancer, bladder cancer, oral mucosal cancer, esophageal cancer, anaplastic astrocytoma, glioblastoma multiforme, acute myeloid leukemia, acute lymphocytic leukemia, chronic myelogenous leukemia, Kaposi's sarcoma, and neuroblastoma.

In some embodiments, the parent drug is selected from an anti-cancer agent, an anti-inflammatory drug, an antibiotic, an anti-fugus agent, a JAK inhibitor, or a VEGF inhibitor.

In some embodiments, the parent drug selected is Fluorouracil, and thus the prodrug compound provided herein is useful in the treatment of cancers, including colon, esophageal, gastric, rectum, breast, biliary tract, stomach, head and neck, cervical, pancreas, renal cell, and carcinoid.

In some embodiments, the parent drug selected is Temozolomide, and thus the prodrug compound provided herein is useful in the treatment of anaplastic astrocytoma and glioblastoma multiforme.

In some embodiment, the parent drug selected is Daunorubicin, and thus the prodrug compound provided herein is useful in the treatment of acute nonlymphocytic leukemia (myelogenous, monocytic, erythroid) and acute lymphocytic leukemia.

In some embodiment, the parent drug selected is 10-hydroxyl-camptothecine or 7-ethyl-10-hydroxyl-camptothecine, and thus the prodrug compound provided herein is useful in the treatment of cancers, including gastric, esophagus, cardiac, colon, liver, lung, bladder, acute leukemia, chronic myelogenous leukemia, and chorionic epithelioma.

In this context, the term "therapeutically effective amount" refers to an amount of a therapeutic agent selected in the drug delivery system provided herein or pharmaceutically acceptable salts thereof which is effective to provide "therapy" in a subject, or to "treat" disorders, diseases or conditions in a subject.

EXAMPLES

For the purpose of illustration, the following examples are included. However, it is to be understood that these examples do not limit the present disclosure and are only meant to suggest a method of practicing the present disclosure. Persons skilled in the art will recognize that the chemical reactions described may be readily adapted to prepare a number of other compounds of the present disclosure or a pharmaceutically acceptable salt thereof, and alternative methods for preparing the compounds of the present disclosure or a pharmaceutically acceptable salt thereof are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents and building blocks known in the art other than those described, and/or by making routine modifications of reaction conditions. Alternatively, other reactions disclosed herein or known in the art will be recognized as having applicability for preparing other compounds of the present disclosure.

As used herein the symbols and conventions used in these processes, schemes and examples are consistent with those used in the contemporary scientific literature, for example, the Journal of the American Chemical Society or the Journal of Biological Chemistry. Unless otherwise noted, all starting materials were obtained from commercial suppliers and used without further purification. For example, the following abbreviations may be used in the examples and throughout the specification: g (grams); mg (milligrams); L (liters); mL (milliliters); L (microliters); psi (pounds per square inch); M (molar); mM (millimolar); i.v. (intravenous); Hz (Hertz); MHz (megahertz); aq. (aqueous solution); mol (moles); mmol (millimoles); r.t. (room temperature); min (minutes); h (hours); mp (melting point); TLC (thin layer chromatography); Rt (retention time); RP (reverse phase); AcOH (acetic acid); MeOH (methanol); i-PrOH (isopropanol); TEA (triethylamine); TFA (trifluoroacetic acid); THE (tetrahydrofuran); DMSO (dimethyl sulfoxide); EtOAc (ethyl acetate); DCM (dichloromethane); HCHO (formaldehyde); MeCN (acetonitrile); DIPEA (N,N-diisopropylethylamine); PE (petroleum ether); DMF (N,N-dimethylformamide); $Pd_2dba_3$ (tris(dibenzylideneacetone)dipalladium); NMP (1-methyl-2-pyrrolidinone); HATU (2-(7-azabenzotriazol-1-yl)-N,N,N',N'-tetramethyluronium hexafluorophosphate); BOP ((benzotriazol-1-yloxy)tris(dimethylamino)phosphonium hexafluorophosphate).

Unless otherwise indicated, all temperatures are expressed in ° C. (degrees Centigrade). All reactions were conducted under an inert atmosphere at r.t. unless otherwise noted.

$^1H$ NMR spectra were recorded on an Agilent 400MR NMR Spectrometer. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet) and br (broad).

Low-resolution mass spectra (MS) and compound purity data were acquired on an Agilent LC/MS single quadrapole system equipped with electrospray ionization (ESI) source, and UV detector (215 and 254 nm).

Example 1

2-(1-(4-(Dibutylamino)phenyl)piperidin-4-yl)ethyl ((5-fluoro-2,4-dioxo-3,4-dihydropyrimidin-1(2H)-yl) methyl) carbonate (1)

1

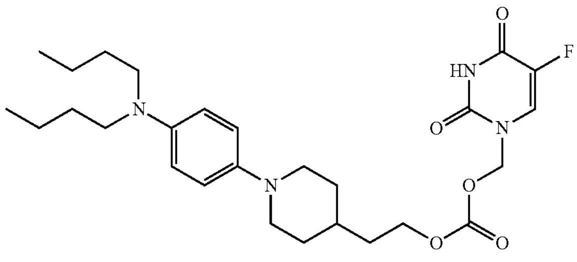

Synthetic Route of 1

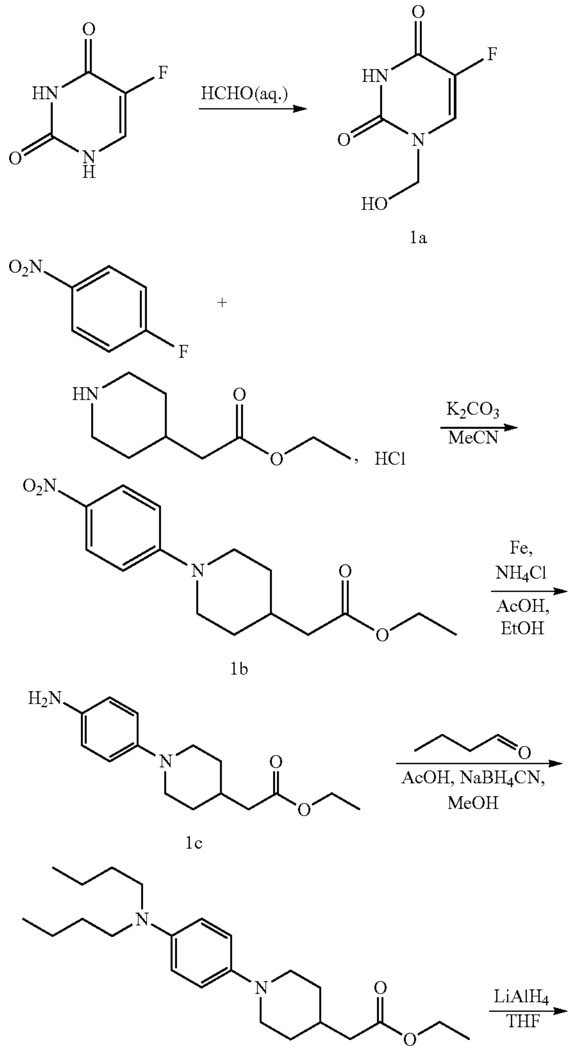

-continued

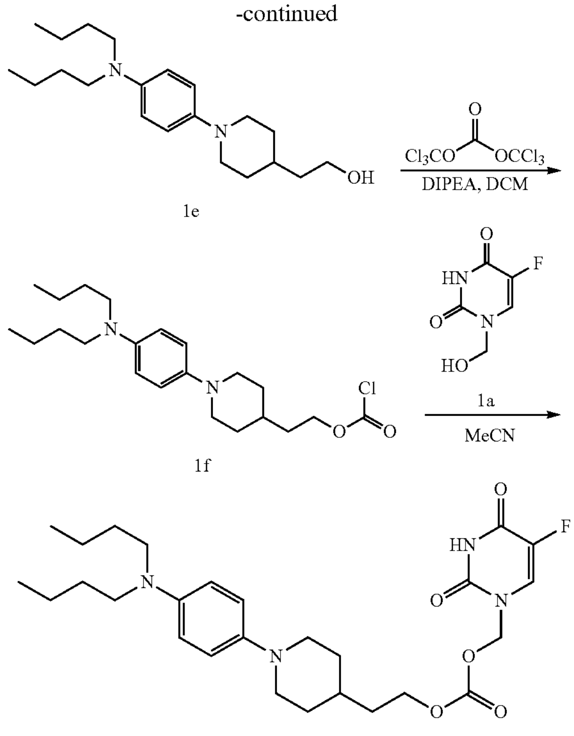

5-Fluoro-1-(hydroxymethyl)pyrimidine-2,4(1H,3H)-dione (1a)

1a

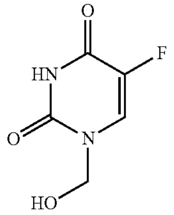

A reaction of 5-Fluorouracil (10 g, 76.9 mmol) and 37% HCHO (aq.) (100 mL) in sealed tube was stirred at 60° C. for 5 hours, and the mixture was concentrated to give the crude product of 5-fluoro-1-(hydroxymethyl)pyrimidine-2,4(1H,3H)-dione (1a), which was used for next step directly. MS-ESI (m/z): 161 [M+1]+.

Ethyl 2-(1-(4-nitrophenyl)piperidin-4-yl)acetate (1b)

1b

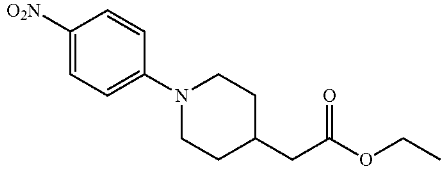

A reaction of 1-fluoro-4-nitrobenzene (248 mg, 1.76 mmol), ethyl 2-(piperidin-4-yl)acetate hydrochloride (443 mg, 2.13 mmol) and $K_2CO_3$ (738 mg, 5.34 mmol) in MeCN (10 mL) was stirred at 110° C. in sealed tube for 5 hours, and the mixture was filtered and concentrated to give the crude product of ethyl 2-(1-(4-nitrophenyl)piperidin-4-yl)acetate (1b), which was used for next step directly. MS-ESI (m/z): 293 $[M+1]^+$.

Ethyl 2-(1-(4-aminophenyl)piperidin-4-yl)acetate (1c)

1c

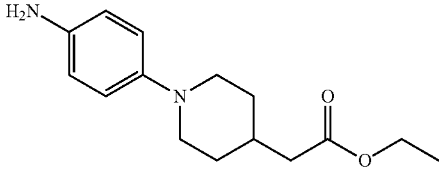

A mixture of ethyl 2-(1-(4-nitrophenyl)piperidin-4-yl)acetate (1b) (415 mg, 1.42 mmol), Fe powder (1.5 g, 26.8 mmol), $(NH_4)_2SO_4$ (108 mg, 0.81 mmol) and 1M HCl (2.5 mL) in EtOH (20 mL) was refluxed for 3 hours. The mixture was filtered and concentrated to give the crude product of ethyl 2-(1-(4-aminophenyl)piperidin-4-yl)acetate (1c), which was used for next step directly. MS-ESI (m/z): 263 $[M+1]^+$.

Ethyl 2-(1-(4-(dibutylamino)phenyl)piperidin-4-yl) acetate (1 d)

1d

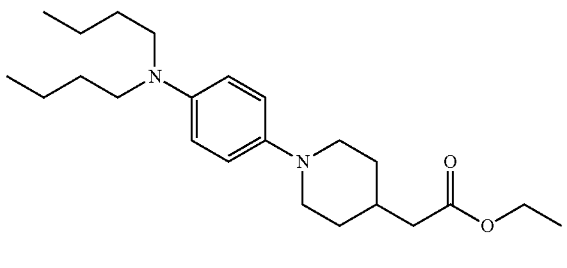

To a solution of ethyl 2-(1-(4-aminophenyl)piperidin-4-yl)acetate (10c) (370 mg, 1.41 mmol) in MeOH (20 mL), AcOH (1 mL), n-butyraldehyde (415 μL, 4.7 mmol) and $NaBH_3CN$ (820 mg, 13.0 mmol) was added. The mixture was stirred for 1.5 h, then concentrated to remove MeOH, dissolved in EtOAc and washed with $NaHCO_3$ (aq), dried and concentrated to give the crude product of ethyl 2-(1-(4-(dibutylamino)phenyl)piperidin-4-yl)acetate (1d), which was used for next step directly. MS-ESI (m/z): 375 $[M+1]^+$.

2-(1-(4-(Dibutylamino)phenyl)piperidin-4-yl)ethan-1-ol (1e)

1e

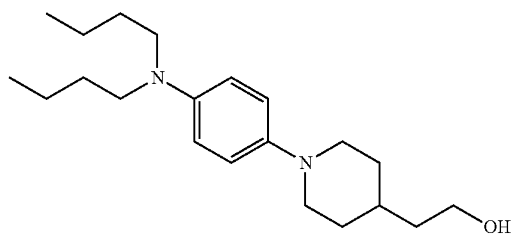

To a solution of ethyl 2-(1-(4-(dibutylamino)phenyl)piperidin-4-yl)acetate (1d) (2.1 g, 5.6 mmol) in THE (24 mL), was added 1M $LiAlH_4$-THF (35 mL, 35 mmol). The mixture was stirred overnight, and quenched with water, extracted with EtOAc, dried and concentrated. The residue was purified by column chromatography on silica gel eluting with petroleum ether and EtOAc to give 304 mg of 2-(1-(4-(dibutylamino)phenyl)piperidin-4-yl)ethan-1-ol (1e). MS-ESI (m/z): 333 $[M+1]^+$.

2-(1-(4-(Dibutylamino)phenyl)piperidin-4-yl)ethyl

1

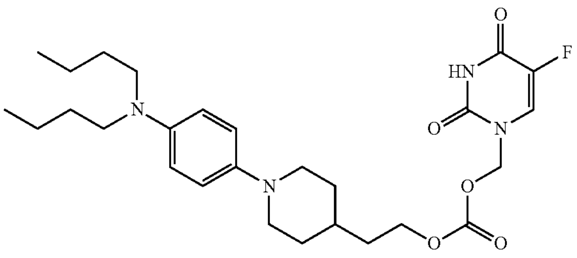

To a solution of 2-(1-(4-(dibutylamino)phenyl)piperidin-4-yl)ethan-1-ol (1e) (160 mg, 0.48 mmol) in DCM (5 mL) cooled below −50° C., was added the solution of DIPEA (850 μL, 4.8 mmol) and triphosgene (142 mg, 0.48 mmol) in DCM (1.4 mL). The mixture was stirred at ambient temperature for 2 h, and added to the solution of 5-fluoro-1-(hydroxymethyl)pyrimidine-2,4(1H,3H)-dione (1a) (310 mg, 1.9 mmol) in MeCN (5 mL). The reaction was stirred overnight, and purified by preparative chromatography eluting with MeCN and 0.1% TFA-$H_2O$ to give 2-(1-(4-(dibutylamino)phenyl)piperidin-4-yl)ethyl((5-fluoro-2,4-dioxo-3,4-dihydropyrimidin-1(2H)-yl)methyl) carbonate (1) (39 mg). MS-ESI (m/z): 519 $[M+1]^+$. $^1H$ NMR (400 MHz, DMSO-$d_6$) δ 12.03 (d, J=5.0 Hz, 1H), 8.14 (d, J=6.5 Hz, 1H), 7.38 (brs, 2H), 6.67 (brs, 2H), 5.58 (s, 2H), 4.18 (t, J=6.2 Hz, 2H), 3.61-2.93 (m, 8H), 2.03-0.58 (m, 21H).

Example 2

4'-(Dipropylamino)-[1,1'-biphenyl]-4-yl ((5-fluoro-2,4-dioxo-3,4-dihydropyrimidin-1(2H)-yl)methyl) carbonate (2)

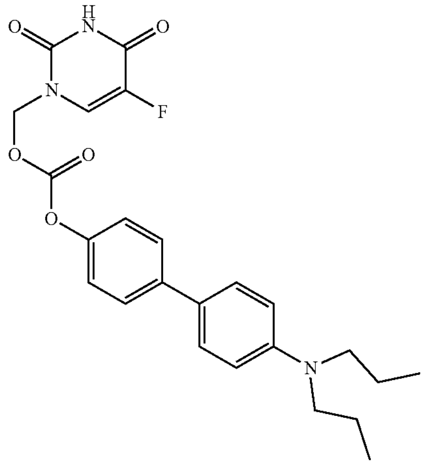 [SMILES: CCCN(CCC)c1ccc(-c2ccc(OC(=O)OCn3cc(F)c(=O)[nH]c3=O)cc2)cc1]

Synthetic Route of 2

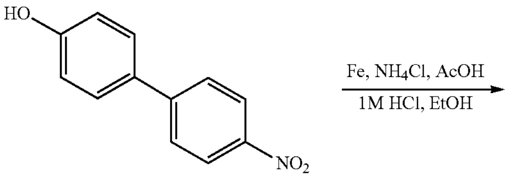

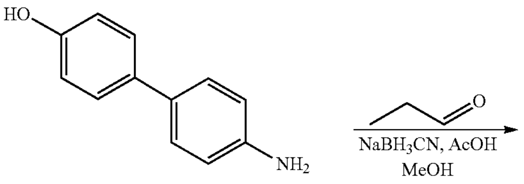

2a

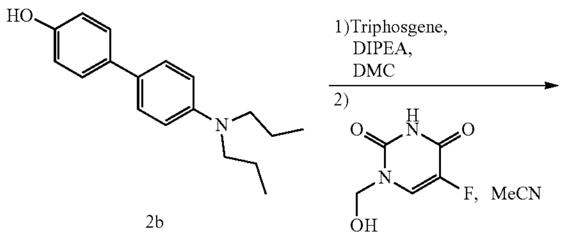

2b

1a

-continued

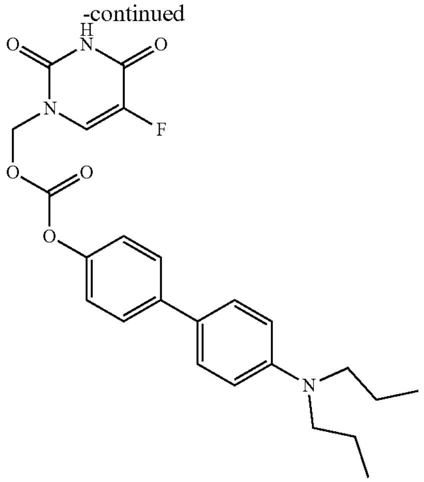

2

4'-Amino-[1,1'-biphenyl]-4-ol (2a)

2a

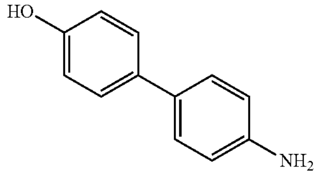

A reaction of 4'-nitro-[1,1'-biphenyl]-4-ol (500 mg, 2.32 mmol), Fe powder (2.63 g, 47.0 mmol), $NH_4Cl$ (125 mg, 2.32 mmol), AcOH (500 μL) and 1M HCl (250 μL) in EtOH (40 mL) was refluxed for 3.5 h. The mixture was filtered and concentrated to give the crude product of 4'-amino-[1,1'-biphenyl]-4-ol (2a), which was used for next step directly. MS-ESI (m/z): 186 $[M+1]^+$.

4'-(Dipropylamino)-[1,1'-biphenyl]-4-ol (2b)

2b

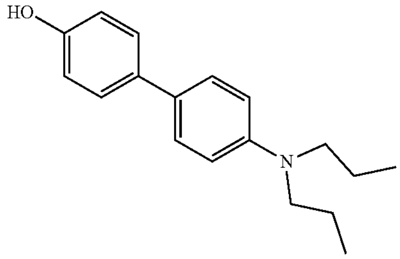

4'-Amino-[1,1'-biphenyl]-4-ol (2a) (400 mg, 2.16 mmol) was dissolved in MeOH (40 mL) and treated with propionaldehyde (760 μL, 10.4 mmol), AcOH (500 μL) and $NaBH_3CN$ (1.75 g, 27.9 mmol). The mixture was stirred overnight. The reaction mixture was filtered and concentrated, the residue was diluted with EtOAc and washed with $NaHCO_3$ (aq.). The aqueous layer was extracted with EtOAc twice. The combined layers were dried over $Na_2SO_4$, and concentrated to dryness. The residue was purified by column chromatography on silica gel (PE:EtOAc=10:1 to 3:1) to give the product of 4'-(dipropylamino)-[1,1'-biphenyl]-4-ol (2b) (510 mg). MS-ESI (m/z): 270 $[M+1]^+$.

4'-(Dipropylamino)-[1,1'-biphenyl]-4-yl ((5-fluoro-2,4-dioxo-3,4-dihydropyrimidin-1(2H)-yl)methyl) carbonate (2)

2

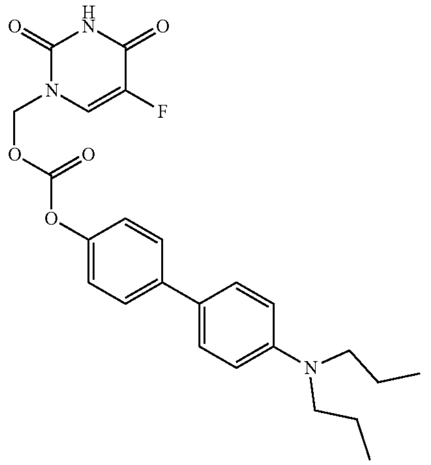

To a solution of 4'-(dipropylamino)-[1,1'-biphenyl]-4-ol (2b) (270 mg, 1 mmol) in DCM (5 mL) cooled below −50° C. was added DIPEA (1.8 mL, 10 mmol) and triphosgene (300 mg, 1 mmol) in DCM (3 mL), the mixture was stirred below −50° C. for 2 h. A suspension of 5-fluoro-1-(hydroxymethyl)pyrimidine-2,4(1H,3H)-dione (1a) (640 mg) in MeCN (5 mL) was added into the mixture and stirred for 1 h. The reaction mixture was filtered and purified by preparative chromatography eluting with MeCN and 0.1% TFA-$H_2O$ to give 4'-(dipropylamino)-[1,1'-biphenyl]-4-yl ((5-fluoro-2,4-dioxo-3,4-dihydropyrimidin-1(2H)-yl) methyl) carbonate (2) (39 mg). MS-ESI (m/z): 456 $[M+1]^+$. $^1H$ NMR (400 MHz, DMSO-$d_6$) δ 12.06 (d, J=5.0 Hz, 1H), 8.16 (d, J=6.5 Hz, 1H), 7.67-7.39 (m, 4H), 7.27 (d, J=8.3 Hz, 2H), 6.72 (brs, 2H), 5.70 (s, 2H), 3.28 (brs, 4H), 1.50 (brs, 4H), 0.87 (t, J=7.4 Hz, 6H).

Example 3

4-(Dipentylamino)phenyl ((5-fluoro-2,4-dioxo-3,4-dihydropyrimidin-1(2H)-yl)methyl) carbonate (3)

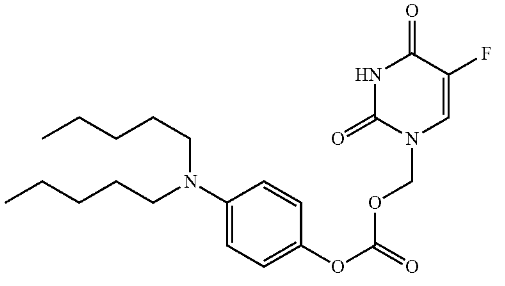

Synthetic Route of 3

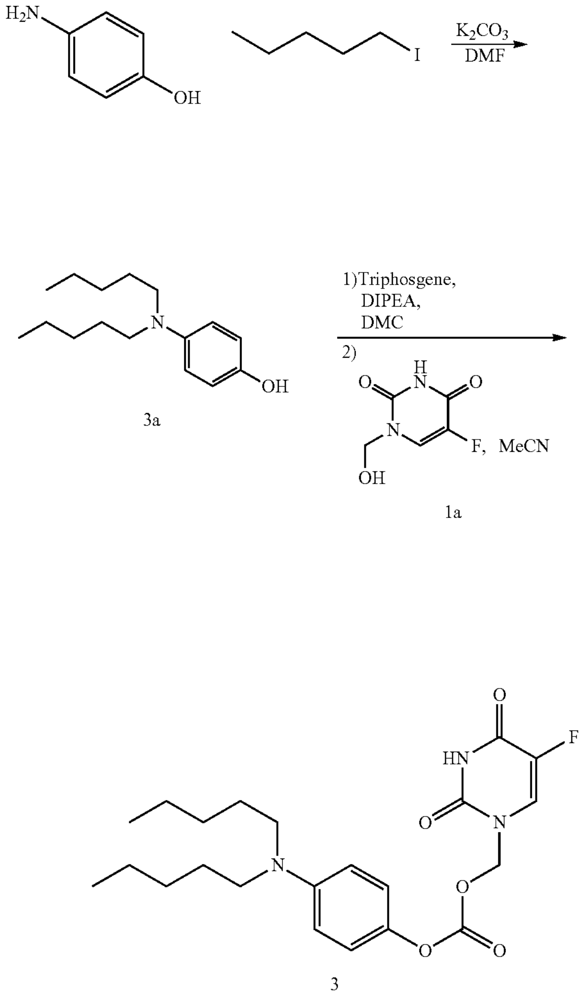

4-(Dipentylamino)phenol (3a)

3a

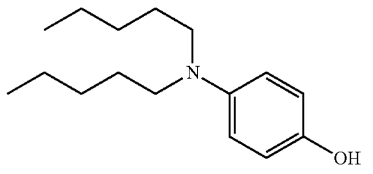

To a mixture of 4-aminophenol (4.0 g, 36.6 mmol), 1-iodopentane (17.1 g, 86.5 mmol) in DMF (72 mL) was added $K_2CO_3$ (5.2 g, 37.4 mmol). The reaction was stirred at 75° C. for 1.5 h. The reaction mixture was poured into water (300 mL), and extracted with EtOAc 3 times. The combined organic layers were washed with $Na_2S_2O_3$ (aq.), dried over $Na_2SO_4$, and evaporated to dryness. The residue was purified by silica gel chromatography eluted with PE and EA to give 4-(dipentylamino)phenol (3a). MS-ESI (m/z): 250 $[M+1]^+$.

4-(Dipentylamino)phenyl ((5-fluoro-2,4-dioxo-3,4-dihydropyrimidin-1(2H)-yl)methyl) carbonate (3)

3

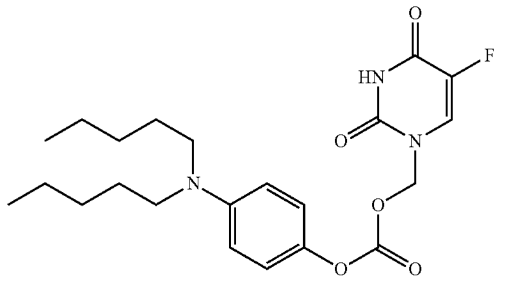 [SMILES: CCCCCN(CCCCC)c1ccc(OC(=O)OCn2cc(F)c(=O)[nH]c2=O)cc1]

To a solution of 4-(dipentylamino)phenol (3a) (250 mg, 1 mmol) in DCM (5 mL) cooled below −50° C. was added DIPEA (1.8 mL, 10 mmol) and triphosgene (300 mg, 1 mmol), the mixture was stirred for 1 h. The mixture was added into the suspension of 5-fluoro-1-(hydroxymethyl) pyrimidine-2,4(1H,3H)-dione (1a) (800 mg) in MeCN (5 mL) dried over 4 Å molecular sieves and stirred for 1 h. The reaction mixture was filtered and purified by preparative chromatography to give 4-(dipentylamino)phenyl ((5-fluoro-2,4-dioxo-3,4-dihydropyrimidin-1(2H)-yl)methyl) carbonate (3) (95 mg). MS-ESI (m/z): 436 $[M+1]^+$. $^1H$ NMR (400 MHz, DMSO-$d_6$) δ 12.05 (d, J=5.0 Hz, 1H), 8.14 (d, J=6.5 Hz, 1H), 7.28-6.40 (m, 4H), 5.67 (s, 2H), 3.47-3.11 (m, 4H), 1.42 (s, 4H), 1.31-1.13 (m, 8H), 0.83 (t, J=6.8 Hz, 6H).

Example 4

4-(1-(3,5-Dimethylphenyl)piperidin-4-yl)phenyl ((5-fluoro-2,4-dioxo-3,4-dihydropyrimidin-1(2H)-yl) methyl) carbonate (4)

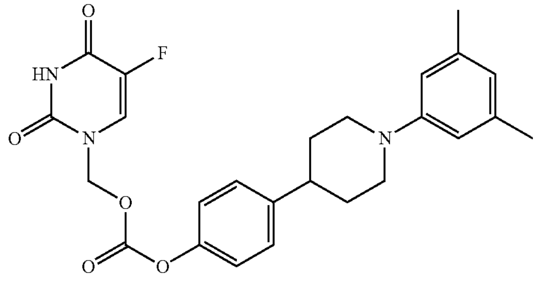 [SMILES: Cc1cc(C)cc(N2CCC(c3ccc(OC(=O)OCn4cc(F)c(=O)[nH]c4=O)cc3)CC2)c1]

Synthetic Route of 4

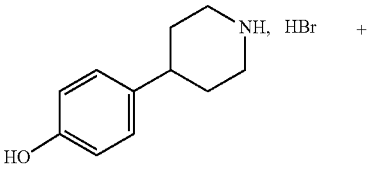

-continued

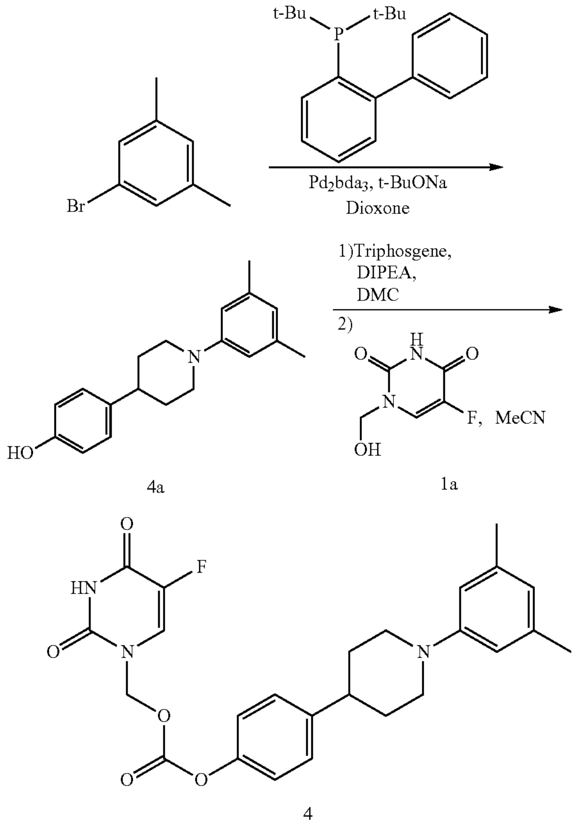

4a

1a

4

4-(1-(3,5-Dimethylphenyl)piperidin-4-yl)phenol (4a)

4a

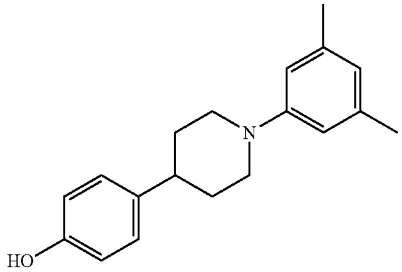

A mixture of 1-bromo-3,5-dimethylbenzene (0.74 g, 4 mmol), 4-(piperidin-4-yl)phenol hydrobromide (1.04 g, 4 mmol), 2-(di-t-butylphosphino))-1,1'-biphenyl (300 mg, 1 mmol), $Pd_2dba_3$ (370 mg, 0.40 mmol) and t-BuONa (0.76 g, 7.9 mmol) in dioxone (40 mL) under nitrogen gas was stirred at 55° C. for 3 h. And 2-(di-t-butylphosphino))-1,1'-biphenyl (300 mg, 1 mmol), $Pd_2dba_3$ (370 mg, 0.40 mmol) and t-BuONa (0.76 g, 7.9 mmol) was added into the reaction additionally. The reaction was stirred at 55° C. for 5 h. The mixture was filtered and washed with EtOAc and the filtrate was concentrated. The residue was purified by column chromatography on silica gel to give 4-(1-(3,5-dimethylphenyl)piperidin-4-yl)phenol (4a) (638 mg). MS-ESI (m/z): 282 $[M+1]^+$.

4-(1-(3,5-Dimethylphenyl)piperidin-4-yl)phenyl ((5-fluoro-2,4-dioxo-3,4-dihydropyrimidin-1(2H)-yl) methyl) carbonate (4)

4

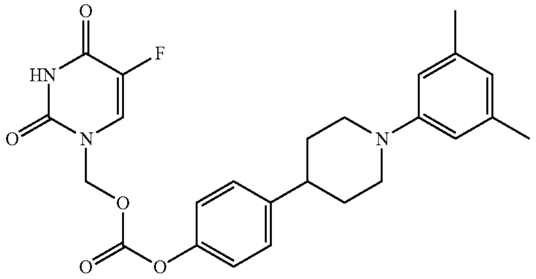

To a solution of 4-(1-(3,5-dimethylphenyl)piperidin-4-yl) phenol (4a) (158 mg, 0.56 mmol) in DCM (4 mL) cooled below −50° C. was added DIPEA (1.0 mL, 5.6 mmol) and triphosgene (167 mg, 0.56 mmol), the mixture was stirred for 1 h. The reaction mixture was added into the suspension of 5-fluoro-1-(hydroxymethyl)pyrimidine-2,4(1H,3H)-dione (1a) (450 mg) in MeCN (5 mL) and stirred for 1 h. The reaction mixture was filtered and purified by preparative chromatography to give 4-(1-(3,5-dimethylphenyl)piperidin-4-yl)phenyl((5-fluoro-2,4-dioxo-3,4-dihydropyrimidin-1(2H)-yl)methyl) carbonate (4) (40 mg). MS-ESI (m/z): 468 $[M+1]^+$. $^1H$ NMR (400 MHz, DMSO-$d_6$) δ 12.05 (d, J=5.0 Hz, 1H), 8.14 (d, J=6.6 Hz, 1H), 7.33 (d, J=8.4 Hz, 2H), 7.21 (d, J=8.3 Hz, 2H), 7.07-6.60 (m, 3H), 5.69 (s, 2H), 4.57-3.59 (m, 4H), 2.83 (brs, 1H), 2.25 (s, 6H), 2.04-1.76 (m, 4H).

Example 5

(5-Fluoro-2,4-dioxo-3,4-dihydropyrimidin-1(2H)-yl) methyl (2-(4-propylphenyl)-1,2,3,4-tetrahydroisoquinolin-6-yl) carbonate (5)

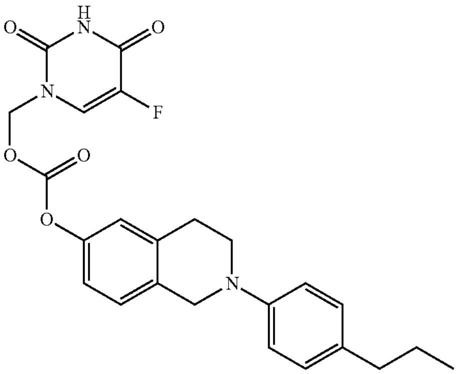

Synthetic Route of 5

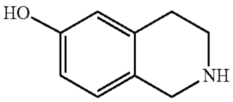

+

-continued

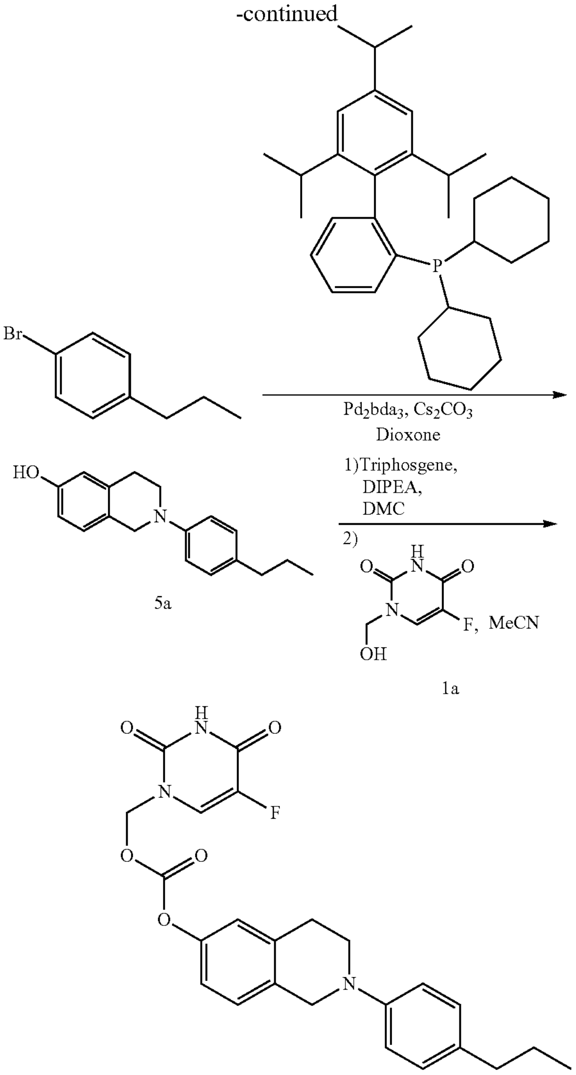

5a
1a
5

2-(4-Propylphenyl)-1,2,3,4-tetrahydroisoquinolin-6-ol (5a)

5a

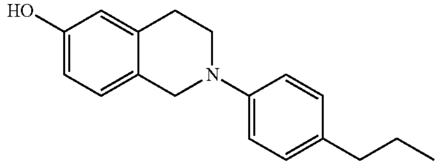

A suspension of 1,2,3,4-tetrahydroisoquinolin-6-ol (0.50 g, 3.36 mmol), 1-bromo-4-propylbenzene (0.75 g, 3.75 mmol), $Pd_2dba_3$ (200 mg, 0.22 mmol), dicyclohexyl(2',4',6'-triisopropyl-[1,1'-biphenyl]-2-yl)phosphane (300 mg, 0.63 mmol) and $Cs_2CO_3$ (3.0 g, 9.2 mmol) in PhMe (15 mL) was stirred in sealed tube at 110° C. for 7 h. The mixture was diluted with EtOAc and filtered. The filtrate was concentrated and purified by column chromatography on silica gel to give 2-(4-propylphenyl)-1,2,3,4-tetrahydroisoquinolin-6-ol (5a) (109 mg). MS-ESI (m/z): 268 $[M+1]^+$.

(5-Fluoro-2,4-dioxo-3,4-dihydropyrimidin-1(2H)-yl) methyl (2-(4-propylphenyl)-1,2,3,4-tetrahydroisoquinolin-6-yl) carbonate (5)

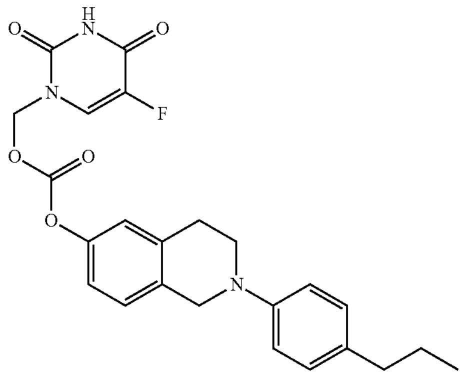 [SMILES: CCCc1ccc(N2CCc3cc(OC(=O)OCn4cc(F)c(=O)[nH]c4=O)ccc3C2)cc1]

5

To a solution of 2-(4-propylphenyl)-1,2,3,4-tetrahydroisoquinolin-6-ol (5a) (26.7 mg, 0.1 mmol) in DCM (1 mL) cooled below −50° C. was added DIPEA (200 μL, 1.1 mmol) and triphosgene (30 mg, 0.1 mmol), the mixture was stirred for 1 h. The reaction mixture was added into the suspension of 5-fluoro-1-(hydroxymethyl)pyrimidine-2,4 (1H,3H)-dione (1a) (80 mg) in MeCN (1 mL) dried over 4 Å molecular sieves and stirred for 1 h. The reaction mixture was filtered and purified by preparative chromatography to give (5-fluoro-2,4-dioxo-3,4-dihydropyrimidin-1(2H)-yl) methyl (2-(4-propylphenyl)-1,2,3,4-tetrahydroisoquinolin-6-yl) carbonate (5) (2.0 mg). MS-ESI (m/z): 454 $[M+1]^+$.

Example 6

(5-Fluoro-2,4-dioxo-3,4-dihydropyrimidin-1(2H)-yl) methyl (4-((1-(4-propylphenyl)piperidin-4-yl) methyl)phenyl) carbonate (6)

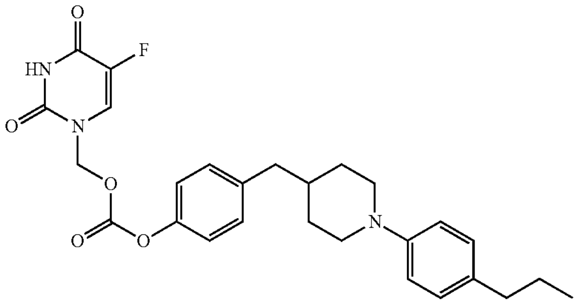

Synthetic Route of 6

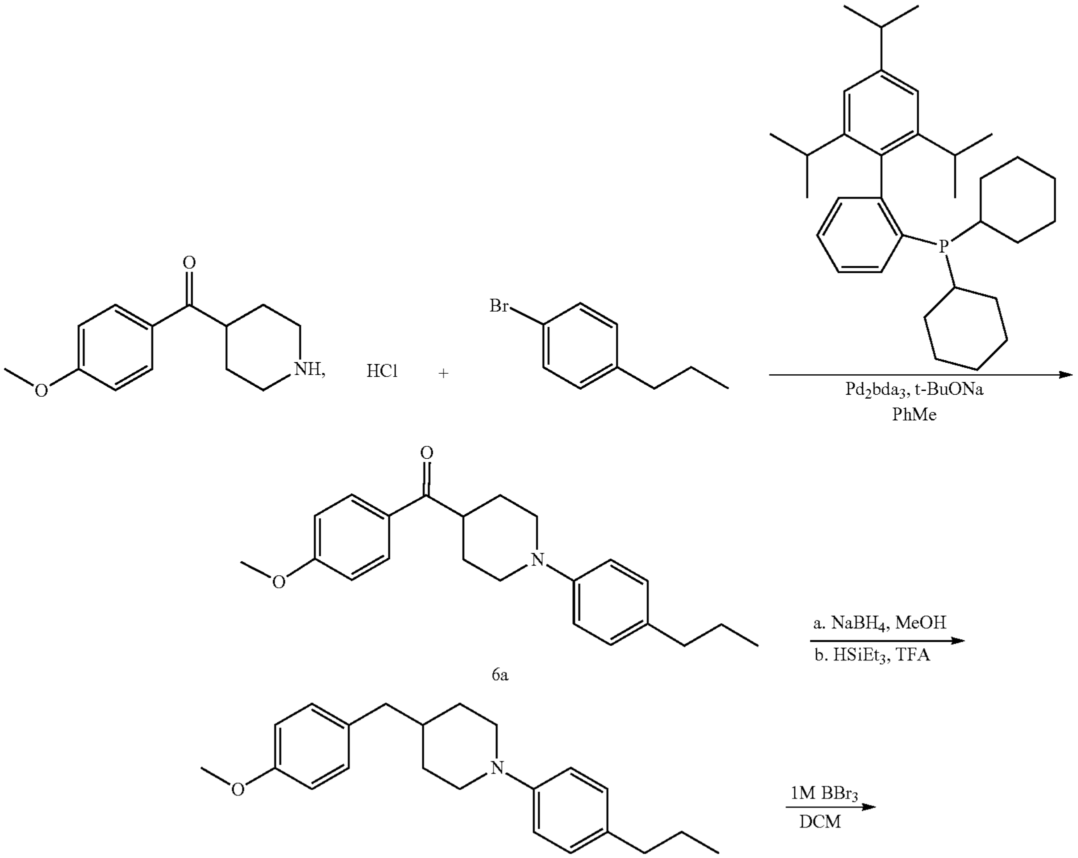

6a

6b

-continued

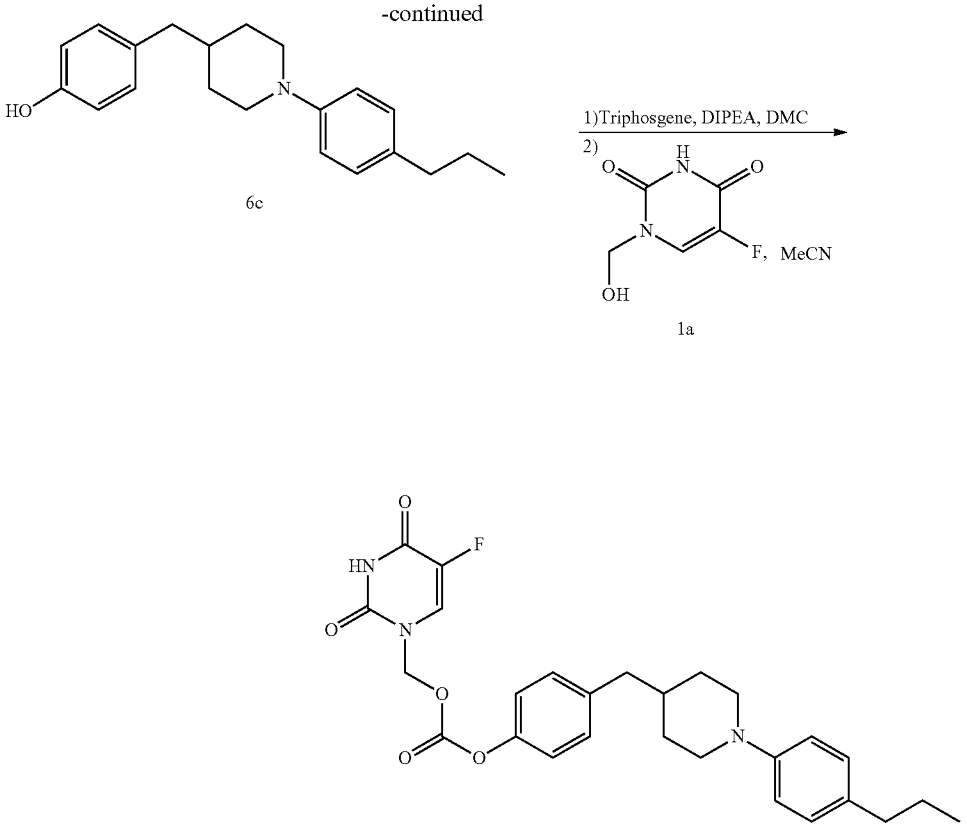

6c
1a
6

(4-Methoxyphenyl)(1-(4-propylphenyl)piperidin-4-yl)methanone (6a)

6a

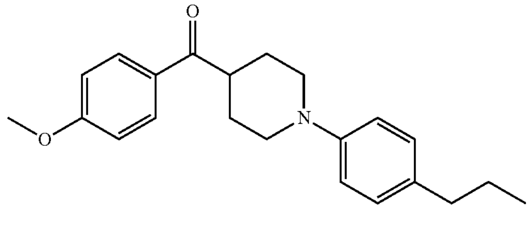

A suspension of (4-methoxyphenyl)(piperidin-4-yl) methanone hydrochloride (1.0 g, 3.9 mmol), 1-bromo-4-propylbenzene (0.8 g, 4.0 mmol), $Pd_2dba_3$ (732 mg, 0.8 mmol), dicyclohexyl (2',4',6'-triisopropyl-[1,1'-biphenyl]-2-yl)phosphane (1.15 g, 2.4 mmol) and t-BuONa (1.1 g, 11.4 mmol) in PhMe (20 mL) was stirred in sealed tube under nitrogen gas at 110° C. for 4 h. The mixture was filtered. The filtrate was concentrated and purified by column chromatography on silica gel to give (4-methoxyphenyl)(1-(4-propylphenyl)piperidin-4-yl)methanone (6a) (1.09 g). MS-ESI (m/z): 338 $[M+1]^+$.

4-(4-Methoxybenzyl)-1-(4-propylphenyl)piperidine (6b)

6b

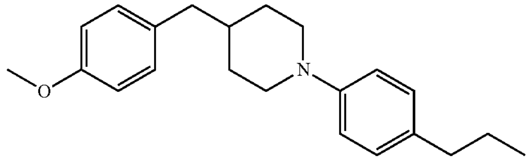

To a solution of (4-methoxyphenyl)(1-(4-propylphenyl) piperidin-4-yl)methanone (6a) (600 mg, 1.78 mmol) in MeOH (20 mL) was added $NaBH_4$ (200 mg, 5.33 mmol). After being stirred for 40 min, $NaBH_4$ (200 mg, 5.33 mmol) was added into the mixture additionally. The reaction was stirred for 1.5 h and quenched with $NaHCO_3$ aqueous solution. The mixture was extracted with EtOAc, dried over $Na_2SO_4$, and evaporated to dryness to afford as a black oily residue.

The residue was dissolved in TFA (20 mL) followed by addition of triethylsilane (3 mL). The reaction was stirred at 80° C. for 1 h and quenched with $NaHCO_3$ aqueous solution. The mixture was extracted with EtOAc to give the crude product of 4-(4-methoxybenzyl)-1-(4-propylphenyl)piperidine (6b) (1.87 g), was used for next step directly. MS-ESI (m/z): 324 $[M+1]^+$.

4-((1-(4-Propylphenyl)piperidin-4-yl)methyl)phenol (6c)

6c

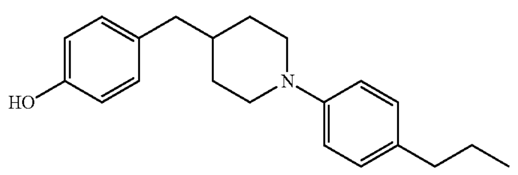

To a solution of 4-(4-methoxybenzyl)-1-(4-propylphenyl) piperidine (6b) (1.87 g) in DCM (10 mL) was added 1M $BBr_3$-DCM solution (6 mL). The reaction was stirred for 1 h. After quenching with $NaHCO_3$ aqueous solution, the mixture was extracted with DCM. The crude product was purified by silica gel chromatography to give 4-((1-(4-propylphenyl)piperidin-4-yl)methyl)phenol (6c) (400 mg). MS-ESI (m/z): 310 $[M+1]^+$.

(5-Fluoro-2,4-dioxo-3,4-dihydropyrimidin-1(2H)-yl) methyl (4-((1-(4-propylphenyl)piperidin-4-yl) methyl)phenyl) carbonate (6)

6

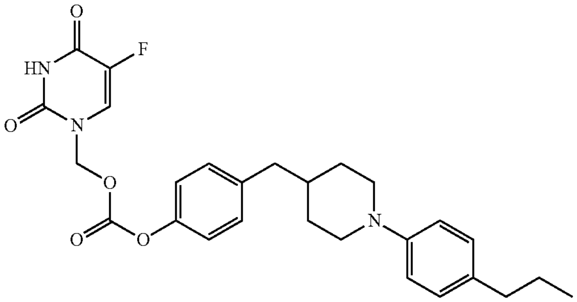 [SMILES: CCCc1ccc(N2CCC(Cc3ccc(OC(=O)OCn4cc(F)c(=O)[nH]c4=O)cc3)CC2)cc1]

To a solution of 4-((1-(4-propylphenyl)piperidin-4-yl) methyl)phenol (6c) (320 mg, 1.0 mmol) in DCM (5 mL) cooled below −50° C. was added DIPEA (1.7 mL, 10.3 mmol) and triphosgene (307 mg, 1.0 mmol), the mixture was stirred for 1 h. The reaction mixture was added into the suspension of 5-fluoro-1-(hydroxymethyl)pyrimidine-2,4 (1H,3H)-dione (1a) (830 mg) in MeCN (5 mL) and stirred for 1 h. The reaction mixture was filtered and purified by preparative chromatography to give (5-fluoro-2,4-dioxo-3,4-dihydropyrimidin-1(2H)-yl)methyl (4-((1-(4-propylphenyl)piperidin-4-yl)methyl)phenyl) carbonate (6) (49 mg). MS-ESI (m/z): 496 $[M+1]^+$. $^1H$ NMR (400 MHz, DMSO-$d_6$) δ 12.05 (d, J=5.0 Hz, 1H), 8.14 (d, J=6.5 Hz, 1H), 7.43-7.09 (m, 8H), 5.69 (s, 2H), 3.85-2.96 (m, 4H), 2.60 (d, J=6.7 Hz, 2H), 2.52 (d, J=7.6 Hz, 2H), 1.78 (d, J=14.3 Hz, 3H), 1.53 (dt, J=16.6, 8.4 Hz, 4H), 0.85 (t, J=7.3 Hz, 3H).

Example 7

4-(1-(2,2-Diphenylethyl)piperidin-4-yl)phenyl ((5-fluoro-2,4-dioxo-3,4-dihydropyrimidin-1(2H)-yl) methyl) carbonate (7)

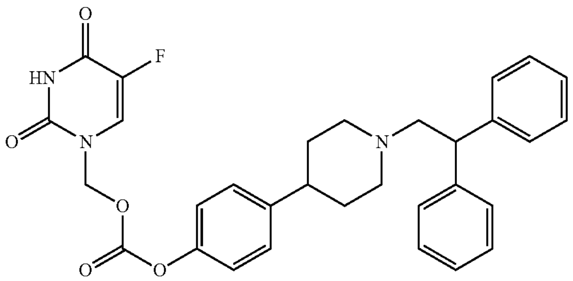

Synthetic Route of 7

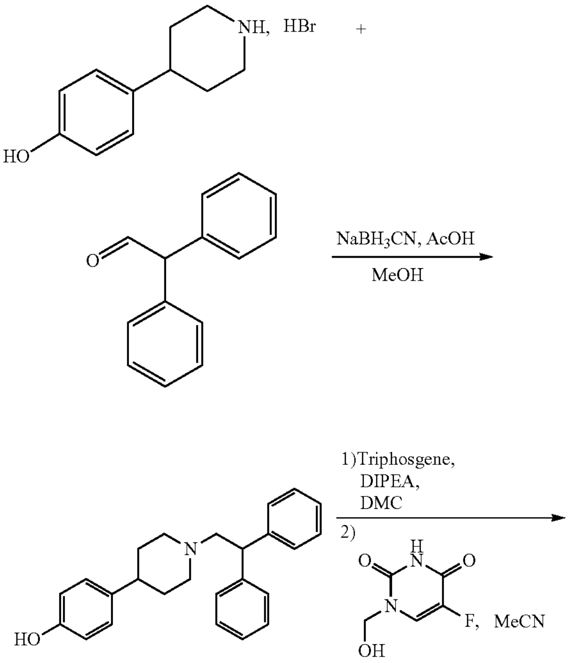

7a

1a

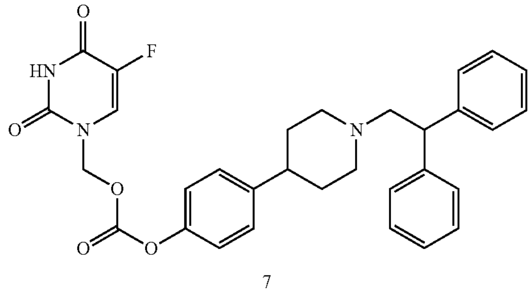

7

4-(1-(2,2-Diphenylethyl)piperidin-4-yl)phenol (7a)

7a

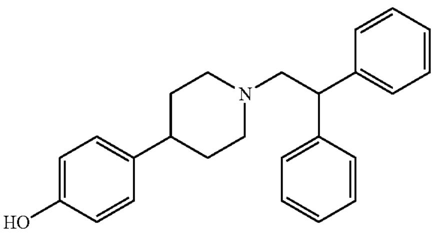

To a solution of 4-(piperidin-4-yl)phenol hydrobromide (500 mg, 1.9 mmol), 2,2-diphenylacetaldehyde (400 mg, 2.0 mmol) and AcOH (0.5 mL) in MeOH (20 mL) was added $NaBH_3CN$ (1.0 g, 15.9 mmol). The reaction was stirred at ambient temperature overnight. After removal of solvent by evaporation, the residue was partitioned between EtOAc and $NaHCO_3$ (aq.). The separated organic layer was dried over $Na_2SO_4$ and evaporated to dryness. The crude product was purified by silica gel chromatography to give 4-(1-(2,2-diphenylethyl)piperidin-4-yl)phenol (7a) (400 mg). MS-ESI (m/z): 358 $[M+1]^+$.

4-(1-(2,2-Diphenylethyl)piperidin-4-yl)phenyl ((5-fluoro-2,4-dioxo-3,4-dihydropyrimidin-1(2H)-yl) methyl) carbonate (7)

7

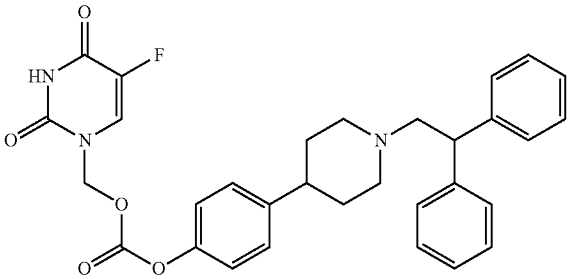 [SMILES: O=C(OCn1cc(F)c(=O)[nH]c1=O)Oc1ccc(C2CCN(CC(c3ccccc3)c3ccccc3)CC2)cc1]

To a solution of 4-(1-(2,2-diphenylethyl)piperidin-4-yl) phenol (7a) (380 mg, 1.06 mmol) in DCM (5 mL) cooled below −50° C. was added DIPEA (1.8 mL, 10.3 mmol) and triphosgene (315 mg, 1.06 mmol), the mixture was stirred for 0.5 h. The reaction mixture was added into the suspension of 5-fluoro-1-(hydroxymethyl)pyrimidine-2,4(1H,3H)-dione (1a) (855 mg) in MeCN (5 mL) and stirred for 2 h. The reaction mixture was filtered and purified by preparative chromatography to give 4-(1-(2,2-diphenylethyl)piperidin-4-yl)phenyl ((5-fluoro-2,4-dioxo-3,4-dihydropyrimidin-1 (2H)-yl)methyl) carbonate (7) (39 mg). MS-ESI (m/z): 544 $[M+1]^+$.

Example 8

4-(1-(Adamantan-1-ylmethyl)piperidin-4-yl)phenyl ((5-fluoro-2,4-dioxo-3,4-dihydropyrimidin-1(2H)-yl) methyl) carbonate (8)

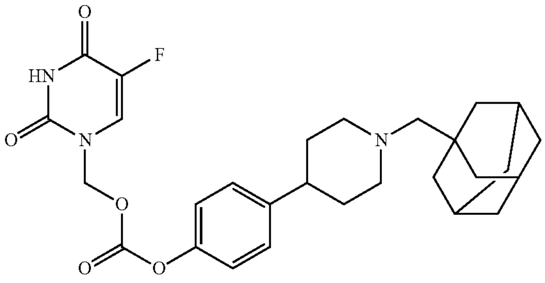 [SMILES: O=C(OCn1cc(F)c(=O)[nH]c1=O)Oc1ccc(C2CCN(CC34CC5CC(CC(C5)C3)C4)CC2)cc1]

Synthetic Route of 8

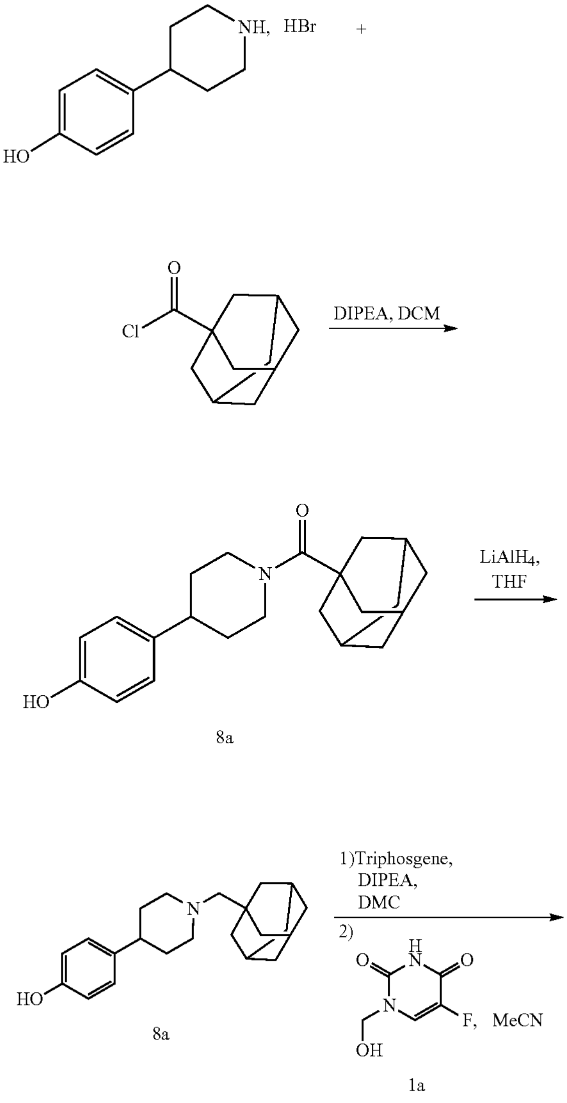

-continued

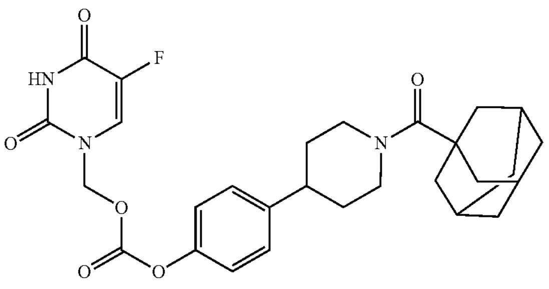

8

Adamantan-1-yl(4-(4-hydroxyphenyl)piperidin-1-yl) methanone (8a)

8a

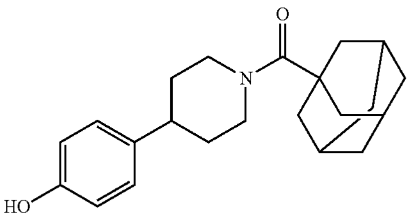

To a mixture of 4-(piperidin-4-yl)phenol hydrobromide (520 mg, 2 mmol) and adamantane-1-carbonyl chloride (400 mg, 2 mmol) in DCM (20 mL) was added DIPEA (1 mL, 5.7 mmol), the reaction was stirred at ambient temperature for 4 h followed by evaporation to give the crude product of adamantan-1-yl(4-(4-hydroxyphenyl)piperidin-1-yl)methanone (8a), which was used for next step directly. MS-ESI (m/z): 340 $[M+1]^+$.

4-(1-(Adamantan-1-ylmethyl)piperidin-4-yl)phenol (8b)

8b

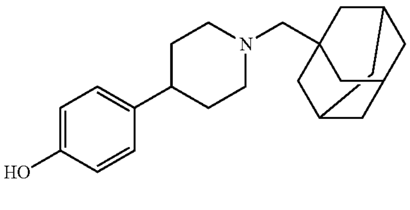

Adamantan-1-yl(4-(4-hydroxyphenyl)piperidin-1-yl) methanone (8a) (650 mg, 1.9 mmol) was dissolved in THF (20 mL) followed by addition of 1M $LiAlH_4$-THF (6 mL, 6 mmol) at ambient temperature. The reaction was stirred for 0.5 h and quenched by addition of NaOH solution. The mixture was filtered and the filtrate was concentrated. The crude product was purified by column chromatography to give the product of 4-(1-(adamantan-1-ylmethyl)piperidin-4-yl)phenol (8b) (595 mg). MS-ESI (m/z): 326 $[M+1]^+$.

4-(1-(Adamantan-1-ylmethyl)piperidin-4-yl)phenyl ((5-fluoro-2,4-dioxo-3,4-dihydropyrimidin-1(2H)-yl) methyl) carbonate (8)

8

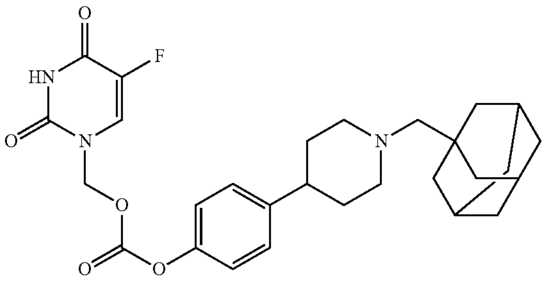

To a solution of 4-(1-(adamantan-1-ylmethyl)piperidin-4-yl)phenol (8b) (575 mg, 1.77 mmol) in DCM (5 mL) cooled below −50° C. was added DIPEA (2.9 mL, 16.6 mmol) and triphosgene (524 mg, 1.77 mmol), the mixture was stirred for 0.5 h. The reaction mixture was added into the suspension of 5-fluoro-1-(hydroxymethyl)pyrimidine-2,4(1H,3H)-dione (1a) (1.13 g) in MeCN (6 mL) and stirred for 1 h. The reaction mixture was filtered and purified by preparative chromatography to give 4-(1-(adamantan-1-ylmethyl)piperidin-4-yl)phenyl ((5-fluoro-2,4-dioxo-3,4-dihydropyrimidin-1(2H)-yl)methyl) carbonate (8) (167 mg). MS-ESI (m/z): 512 $[M+1]^+$. $^1H$ NMR (400 MHz, DMSO-$d_6$) δ 12.05 (d, J=5.0 Hz, 1H), 8.13 (d, J=6.6 Hz, 1H), 7.41-7.19 (m, 4H), 5.69 (s, 2H), 3.76-2.77 (m, 7H), 2.18-1.55 (m, 19H).

Example 9

4-((1-Benzhydrylpiperidin-4-yl)methyl)phenyl ((5-fluoro-2,4-dioxo-3,4-dihydropyrimidin-1(2H)-yl) methyl) carbonate (9)

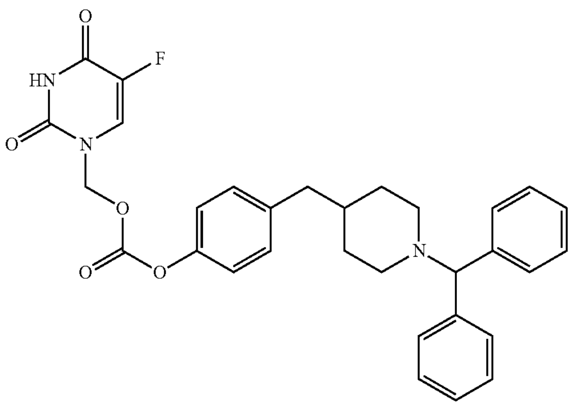 [SMILES: O=C(OCn1cc(F)c(=O)[nH]c1=O)Oc1ccc(CC2CCN(C(c3ccccc3)c3ccccc3)CC2)cc1]

Synthetic Route of 9

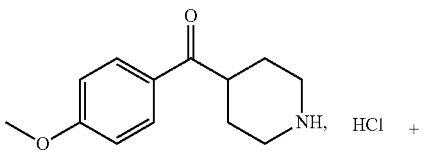

-continued

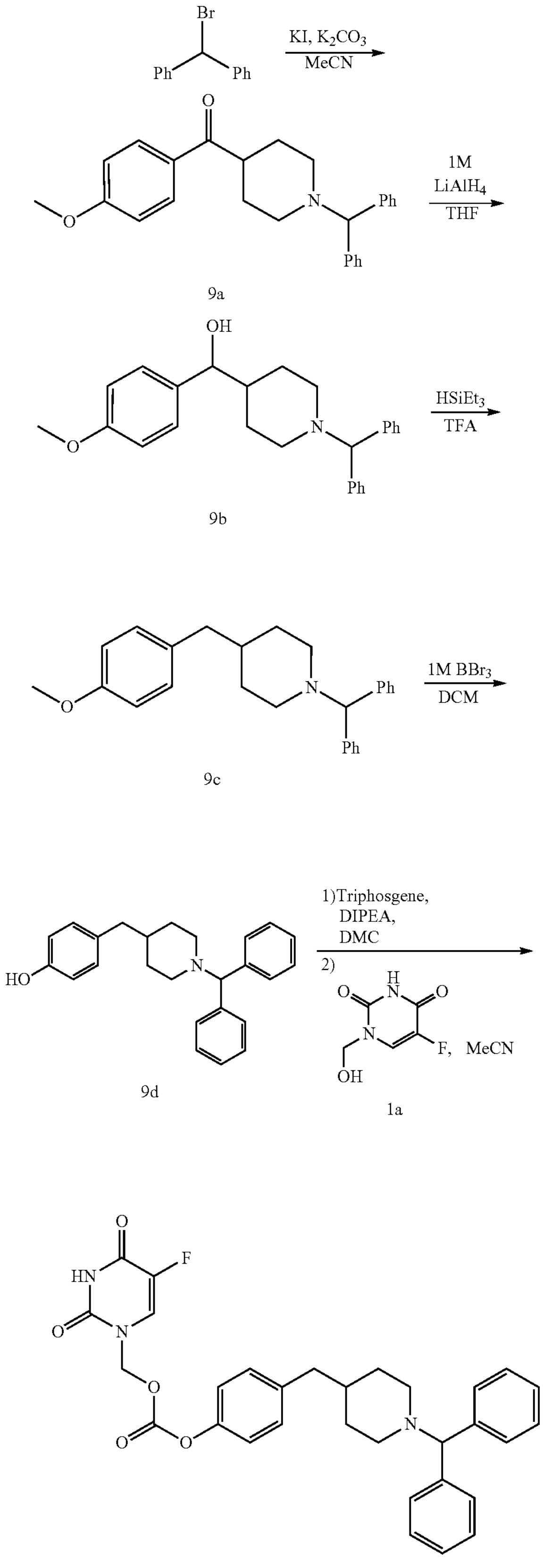

9a

9b

9c

9d

1a

9

(1-Benzhydrylpiperidin-4-yl)(4-methoxyphenyl)methanone (9a)

9a

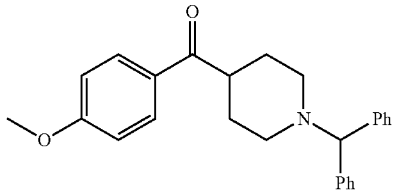

A suspension of (4-methoxyphenyl)(piperidin-4-yl)methanone hydrochloride (520 mg, 2.0 mmol), (bromomethylene)dibenzene (520 mg, 2.1 mmol), KI (340 mg, 2.0 mmol) and $K_2CO_3$ (820 mg, 5.9 mmol) in MeCN (20 mL) was stirred at 90° C. overnight. The mixture was filtered and the filtrate was evaporated to dryness to give the crude product of (1-benzhydrylpiperidin-4-yl)(4-methoxyphenyl)methanone (9a). MS-ESI (m/z): 386 $[M+1]^+$.

(1-Benzhydrylpiperidin-4-yl)(4-methoxyphenyl)methanol (9b)

9b

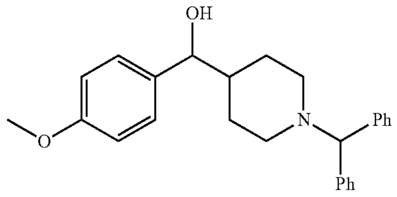

(1-Benzhydrylpiperidin-4-yl)(4-methoxyphenyl)methanone (9a) (750 mg, 1.94 mmol) was dissolved in THF (20 mL) followed by addition of 1M $LiAlH_4$-THF solution (4 mL, 4 mmol). The reaction was stirred for 0.5 h and quenched with NaOH (aq.) solution. The mixture was filtered and the filtrate was evaporated to dryness to give the crude product of (1-benzhydrylpiperidin-4-yl)(4-methoxyphenyl)methanol (9b). MS-ESI (m/z): 388 $[M+1]^+$.

1-Benzhydryl-4-(4-methoxybenzyl)piperidine (9c)

9c

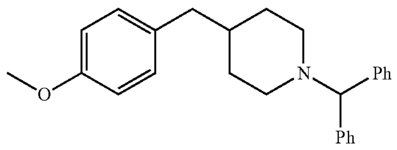

(1-Benzhydrylpiperidin-4-yl)(4-methoxyphenyl)methanol (9b) (939 mg, 2.43 mmol) was dissolved in TFA (5 mL) followed by addition $HSiEt_3$ (2.5 mL). The reaction was stirred at for 1 h and concentrated. The residue was dissolved in DCM, washed with $NaHCO_3$ solution. The organic layer was dried over $Na_2SO_4$ and concentrated to give the crude product of 1-benzhydryl-4-(4-methoxybenzyl)piperidine (9c). MS-ESI (m/z): 372 $[M+1]^+$.

4-((1-Benzhydrylpiperidin-4-yl)methyl)phenol (9d)

9d

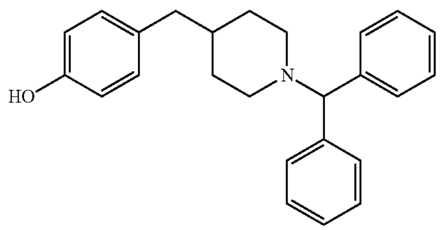

1-Benzhydryl-4-(4-methoxybenzyl)piperidine (9c) (1.07 g, 2.88 mmol) was dissolved in DCM (8 mL) followed by addition of 1M $BBr_3$-DCM solution (6 mL, 6 mmol). The mixture was stirred at room temperature for 5 h. The reaction was diluted with DCM and quenched with $NaHCO_3$ (aq.) solution. The aqueous layer was extracted with DCM. The combined DCM layers were dried over $Na_2SO_4$, and concentrated to dryness. The residue was purified by column chromatography on silica gel (PE:EtOAc=10:1 to 3:1) to give the product of 4-((1-benzhydrylpiperidin-4-yl)methyl) phenol (9d) (504 mg). MS-ESI (m/z): 358 $[M+1]^+$.

4-((1-Benzhydrylpiperidin-4-yl)methyl)phenyl ((5-fluoro-2,4-dioxo-3,4-dihydropyrimidin-1(2H)-yl) methyl) carbonate (9)

9

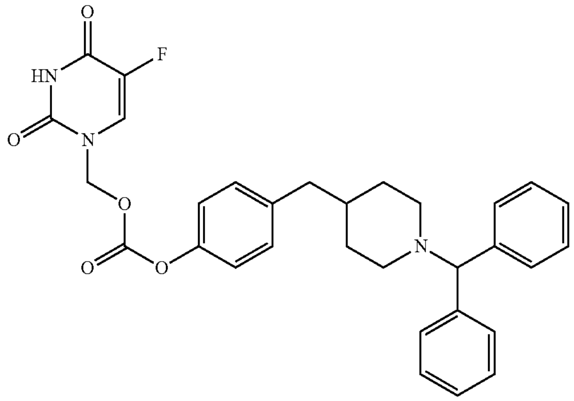

To a solution of 4-((1-benzhydrylpiperidin-4-yl)methyl) phenol (9d) (100 mg, 0.28 mmol) in DCM (3 mL) cooled below −50° C. was added DIPEA (700 μL, 4.2 mmol) and triphosgene (100 mg, 0.34 mmol) and the mixture was stirred for 0.5 h. The reaction mixture was added into the suspension of 5-fluoro-1-(hydroxymethyl)pyrimidine-2,4 (1H,3H)-dione (1a) (180 mg) in MeCN (3 mL) and stirred for 1 h. The reaction mixture was filtered and purified by preparative chromatography to give 4-((1-benzhydrylpiperidin-4-yl)methyl)phenyl ((5-fluoro-2,4-dioxo-3,4-dihydropyrimidin-1(2H)-yl)methyl) carbonate (9) (27 mg). MS-ESI (m/z): 544 $[M+1]^+$. $^1$H NMR (400 MHz, Chloroform-d) δ 7.61 (d, J=5.2 Hz, 1H), 7.37 (d, J=7.5 Hz, 4H), 7.29-7.10 (m, 8H), 7.05 (d, J=8.5 Hz, 2H), 5.74 (s, 2H), 4.21 (s, 1H), 2.84 (d, J=11.4 Hz, 2H), 2.53 (d, J=6.6 Hz, 2H), 2.35 (s, 1H), 1.76 (t, J=11.5 Hz, 2H), 1.61-1.42 (m, 3H), 1.38-1.24 (m, 2H).

Example 10

4-(4-Butylpiperidin-1-yl)phenethyl 5-fluoro-2,4-dioxo-3,4-dihydropyrimidine-1(2H)-carboxylate (10)

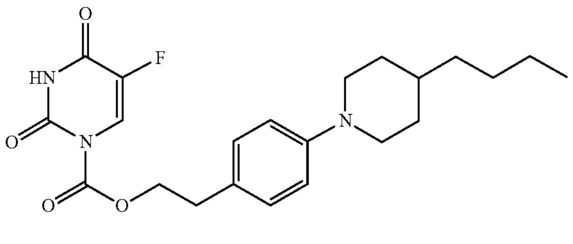

Synthetic Route of 10

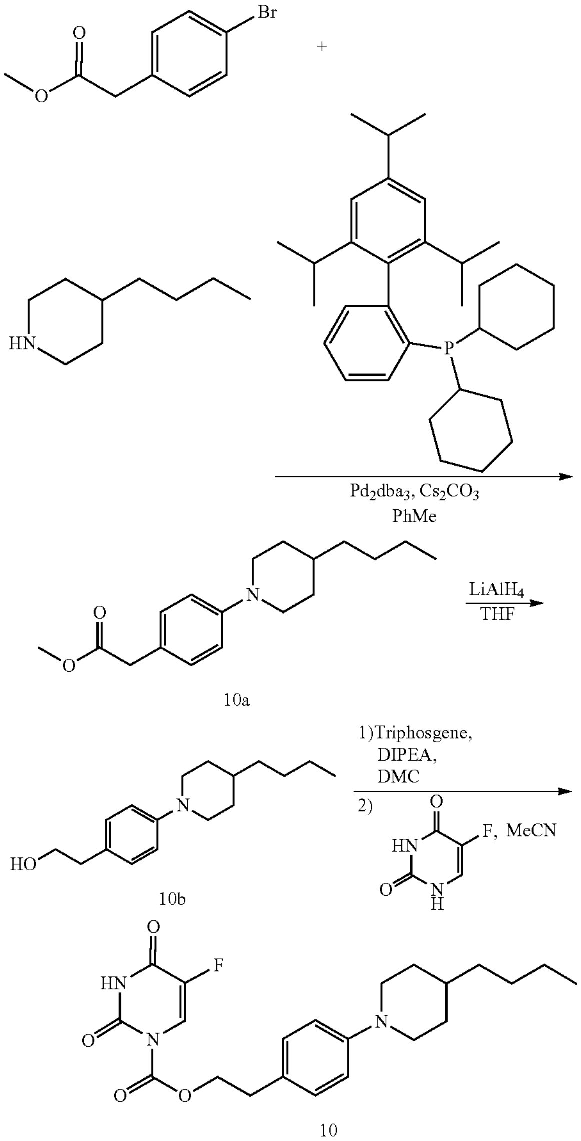

Methyl 2-(4-(4-butylpiperidin-1-yl)phenyl)acetate (10a)

10a

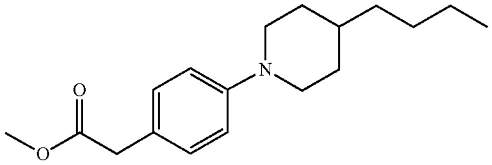

A suspension of methyl 2-(4-bromophenyl)acetate (241.2 mg, 1.05 mmol), 4-butylpiperidine hydrochloride (207.6 g, 1.17 mmol), $Pd_2dba_3$ (33 mg, 0.035 mmol), dicyclohexyl (2',4',6'-triisopropyl-[1,1'-biphenyl]-2-yl)phosphane (67 mg, 0.14 mmol) and $Cs_2CO_3$ (1.14 g, 3.51 mmol) in PhMe (10 mL) was stirred in sealed tube at 110° C. for 18 h. The mixture was diluted with MeCN and filtered. The filtrate was concentrated to give the crude product of methyl 2-(4-(4-butylpiperidin-1-yl)phenyl)acetate (10a), which was used for next step directly. MS-ESI (m/z): 290 $[M+1]^+$.

2-(4-(4-Butylpiperidin-1-yl)phenyl)ethan-1-ol (10b)

10b

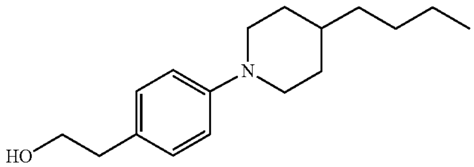

Methyl 2-(4-(4-butylpiperidin-1-yl)phenyl)acetate (10a) (300 mg, 1.03 mmol) was dissolved in THE (11 mL) followed by addition of 1M $LiAlH_4$-THF (3 mL). The mixture was stirred at room temperature overnight. The reaction was quenched with water. The aqueous layer was extracted with EtOAc 3 times. The combined EtOAc layers were dried over $Na_2SO_4$ and evaporated to dryness. The residue was purified by preparative chromatography to give 2-(4-(4-butylpiperidin-1-yl)phenyl)ethan-1-ol (10b) (281 mg). MS-ESI (m/z): 262 $[M+1]^+$.

4-(4-Butylpiperidin-1-yl)phenethyl 5-fluoro-2,4-dioxo-3,4-dihydropyrimidine-1(2H)-carboxylate (10)

10

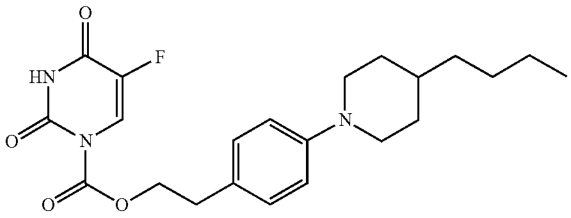 [SMILES: CCCCC1CCN(c2ccc(CCOC(=O)n3cc(F)c(=O)[nH]c3=O)cc2)CC1]

A mixture of 2-(4-(4-butylpiperidin-1-yl)phenyl)ethan-1-ol (10b) (94 mg, 0.36 mmol), triphosgene (108 mg, 0.36 mmol) and DIPEA (650 μL) in DCM (3.5 mL) cooled below −50° C. was stirred for 2 h, followed by addition of the suspension of fluorouracil (50 mg, 0.38 mmol) in MeCN (3.6 mL). The reaction was stirred at room temperature for 2 h followed by concentration to dryness. The crude product was purified by preparative chromatography to give 4-(4-butylpiperidin-1-yl)phenethyl 5-fluoro-2,4-dioxo-3,4-dihydropyrimidine-1(2H)-carboxylate (10) (35 mg). MS-ESI (m/z): 418 $[M+1]^+$. $^1H$ NMR (400 MHz, DMSO-$d_6$) δ 12.00 (d, J=4.9 Hz, 1H), 8.12 (d, J=7.2 Hz, 1H), 7.44-7.16 (m, 4H), 4.45 (t, J=6.6 Hz, 2H), 3.62-2.94 (m, 4H), 1.83 (d, J=13.2 Hz, 2H), 1.58-0.96 (m, 11H), 0.90-0.77 (m, 3H).

Example 11

2-(1-(4-(Dibutylamino)phenyl)piperidin-4-yl)ethyl 5-fluoro-2,4-dioxo-3,4-dihydropyrimidine-1(2H)-carboxylate (11)

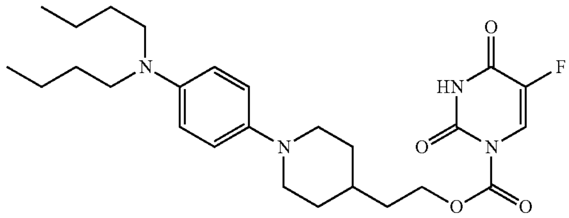

Synthetic Route of 11

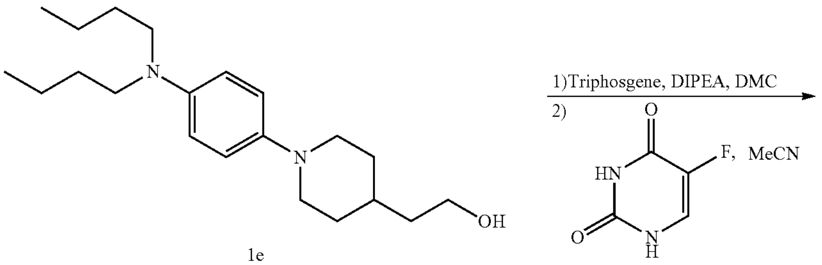

1e

-continued

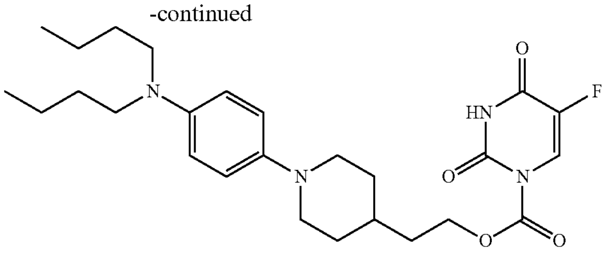

11

2-(1-(4-(Dibutylamino)phenyl)piperidin-4-yl)ethyl 5-fluoro-2,4-dioxo-3,4-dihydropyrimidine-1(2H)-carboxylate (11)

11

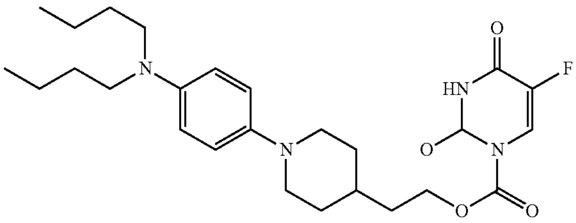 [SMILES: CCCCN(CCCC)c1ccc(N2CCC(CCOC(=O)n3cc(F)c(=O)[nH]c3=O)CC2)cc1]

To the solution of 2-(1-(4-(dibutylamino)phenyl)piperidin-4-yl)ethan-1-ol (1e) (278 mg, 0.84 mmol) in DCM (7 mL) cooled below −50° C., was added the solution of DIPEA (1.4 mL, 8.4 mmol) and triphosgene (248 mg, 0.84 mmol) in DCM (2.5 mL). The mixture was stirred at ambient temperature for 1.5 h, and added to the suspension of fluorouracil (109 mg, 0.84 mmol) in MeCN (10 mL). The reaction was stirred overnight, and purified by preparative chromatography eluting with MeCN and 0.1% TFA-$H_2O$ to give 2-(1-(4-(dibutylamino)phenyl)piperidin-4-yl)ethyl 5-fluoro-2,4-dioxo-3,4-dihydropyrimidine-1(2H)-carboxylate (11) (99 mg). MS-ESI (m/z): 489 $[M+1]^+$. $^1H$ NMR (400 MHz, DMSO-$d_6$) δ 12.02 (s, 1H), 8.21 (d, J=7.2 Hz, 1H), 7.39 (brs, 2H), 6.67 (brs, 2H), 4.37 (t, J=6.1 Hz, 2H), 3.90-3.15 (m, 8H), 2.12-1.05 (m, 15H), 0.92-0.68 (m, 6H).

Example 12

4-((1-Benzhydrylpiperidin-4-yl)methyl)phenyl ((5-fluoro-2,4-dioxo-3,4-dihydropyrimidin-1(2H)-yl) methyl) methylphosphonate (12)

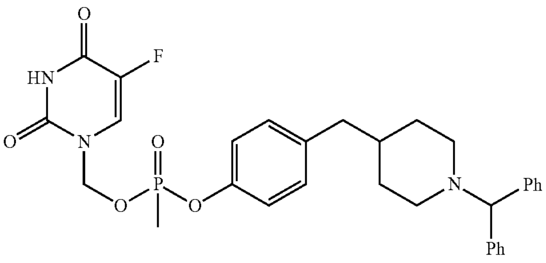 [SMILES: CP(=O)(OCn1cc(F)c(=O)[nH]c1=O)Oc1ccc(CC2CCN(C(c3ccccc3)c3ccccc3)CC2)cc1]

Synthetic Route of 12

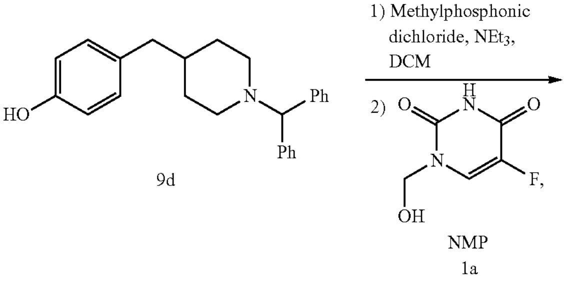

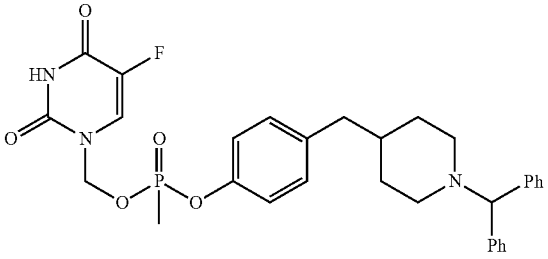 [SMILES: CP(=O)(OCn1cc(F)c(=O)[nH]c1=O)Oc1ccc(CC2CCN(C(c3ccccc3)c3ccccc3)CC2)cc1]

12

4-((1-Benzhydrylpiperidin-4-yl)methyl)phenyl ((5-fluoro-2,4-dioxo-3,4-dihydropyrimidin-1(2H)-yl) methyl) methylphosphonate (12)

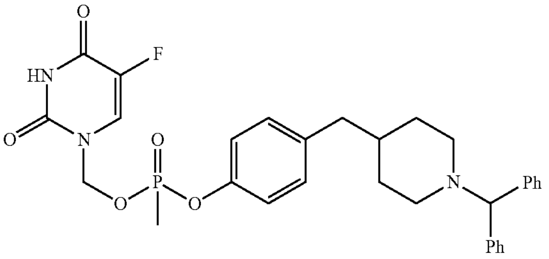

To a solution of 4-((1-benzhydrylpiperidin-4-yl)methyl) phenol (9d) (200 mg, 0.56 mmol) in DCM (2 mL) at ambient temperature was added $NEt_3$ (310 μL, 2.24 mmol) and methyl phosphonic dichloride (90 mg, 0.67 mmol), the mixture was stirred for 0.5 h. The reaction mixture was added into the suspension of 5-fluoro-1-(hydroxymethyl) pyrimidine-2,4(1H,3H)-dione (1a) (360 mg) in NMP (2 mL) and stirred for 3 h. The reaction mixture was filtered and purified by preparative chromatography to give 4-((1-benzhydrylpiperidin-4-yl)methyl)phenyl ((5-fluoro-2,4-dioxo- 3,4-dihydropyrimidin-1(2H)-yl)methyl) methylphosphonate (12) (90 mg). MS-ESI (m/z): 578 $[M+1]^+$. $^1H$ NMR (400 MHz, Chloroform-d) δ 7.41-7.29 (m, 5H), 7.24-7.18 (m, 4H), 7.18-7.09 (m, 2H), 7.07-6.89 (m, 4H), 5.72-5.31 (m, 2H), 4.22 (s, 1H), 2.95-2.78 (m, 2H), 2.55-2.42 (m, 2H), 1.83-1.65 (m, 4H), 1.55-1.20 (m, 6H).

Example 13

(S)-4-ethyl-4-hydroxy-3,14-dioxo-3,4,12,14-tetrahydro-1H-pyrano[3',4':6,7]indolizino[1,2-b]quinolin-9-yl 2-(1-(2,2-diphenylethyl)piperidin-4-yl)acetate (13)

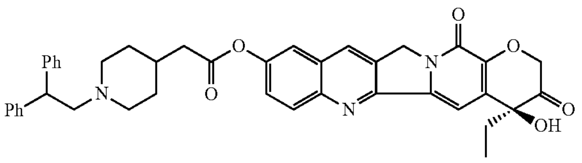

Synthetic Route of 13

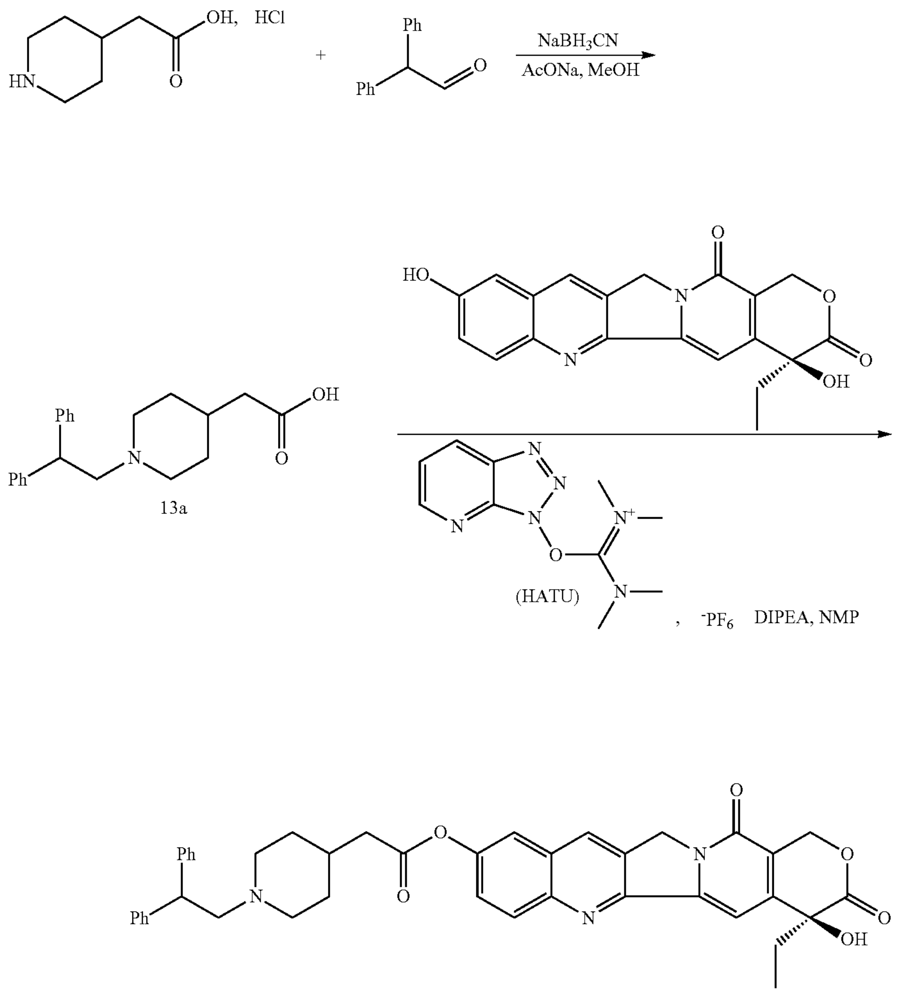

13

2-(1-(2,2-Diphenylethyl)piperidin-4-yl)acetic acid (13a)

13a

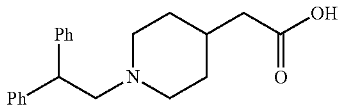

To a suspension of 2-(piperidin-4-yl)acetic acid hydrochloride (2.3 g, 12.8 mmol), 2,2-diphenylacetaldehyde (2.5 g, 12.7 mmol) and AcONa (3.1 g, 37.8 mmol) in MeOH (25 mL) was added $NaBH_3CN$ (2.0 g, 31.8 mmol). The reaction was stirred at ambient temperature for 4.5 h. After removal of solvent by evaporation, the residue was partitioned between EtOAc and $H_2O$. The separated organic layer was dried over $Na_2SO_4$, and evaporated to dryness. The crude product was purified by silica gel chromatography to give 2-(1-(2,2-diphenylethyl)piperidin-4-yl)acetic acid (13a) (517 mg). MS-ESI (m/z): 324 $[M+1]^+$.

(S)-4-ethyl-4-hydroxy-3,14-dioxo-3,4,12,14-tetrahydro-1H-pyrano[3',4':6,7]indolizino[1,2-b]quinolin-9-yl 2-(1-(2,2-diphenylethyl)piperidin-4-yl)acetate (13)

13

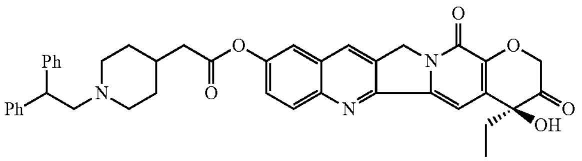 [SMILES: CC[C@@]1(O)C(=O)COc2c1cc1n(c2=O)Cc2cc3cc(OC(=O)CC4CCN(CC(c5ccccc5)c5ccccc5)CC4)ccc3nc2-1]

A mixture of 10-hydroxycamptothecin (36 mg, 0.1 mmol), 2-(1-(2,2-diphenylethyl)piperidin-4-yl)acetic acid (13a) (32 mg, 0.1 mmol), HATU (114 mg, 0.3 mmol), DIPEA (105 μL, 0.6 mmol) in NMP (2 mL) was stirred at room temperature for 23 h. The reaction mixture was purified by preparative chromatography to give (S)-4-ethyl-4-hydroxy-3,14-dioxo-3,4,12,14-tetrahydro-1H-pyrano[3',4':6,7]indolizino[1,2-b]quinolin-9-yl 2-(1-(2,2-diphenylethyl)piperidin-4-yl)acetate (13) as a trifluoroacetate salt. MS-ESI (m/z): 670 $[M+1]^+$. $^1$H NMR (400 MHz, DMSO-$d_6$) δ 8.99 (s, 1H), 8.65 (s, 1H), 8.20 (d, J=9.2 Hz, 1H), 7.89 (d, J=2.8 Hz, 1H), 7.65 (dd, J=9.3, 2.6 Hz, 1H), 7.47-7.18 (m, 11H), 6.52 (brs, 1H), 5.41 (s, 2H), 5.28 (s, 2H), 4.60-4.53 (m, 1H), 3.95-3.85 (m, 2H), 3.51 (d, J=12.0 Hz, 2H), 3.31-2.85 (m, 2H), 2.63 (d, J=7.0 Hz, 2H), 2.15-1.72 (m, 5H), 1.60-1.45 (m, 1H), 1.12-0.96 (m, 1H), 0.86 (t, J=7.3 Hz, 3H).

Example 14

(S)-4,11-diethyl-4-hydroxy-3,14-dioxo-3,4,12,14-tetrahydro-1H-pyrano[3',4':6,7]indolizino[1,2-b]quinolin-9-yl benzhydrylprolinate (14)

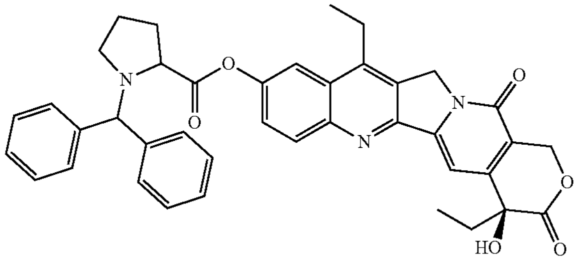 [SMILES: CCc1c2c(nc3ccc(OC(=O)C4CCCN4C(c4ccccc4)c4ccccc4)cc13)-c1cc3c(c(=O)n1C2)COC(=O)[C@]3(O)CC]

Synthetic Route of 14

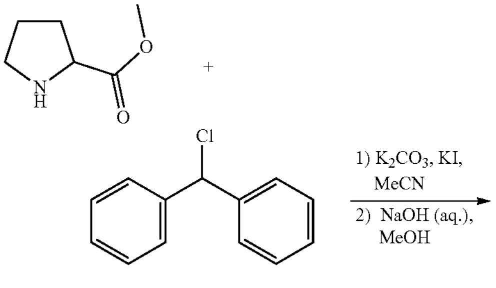

-continued

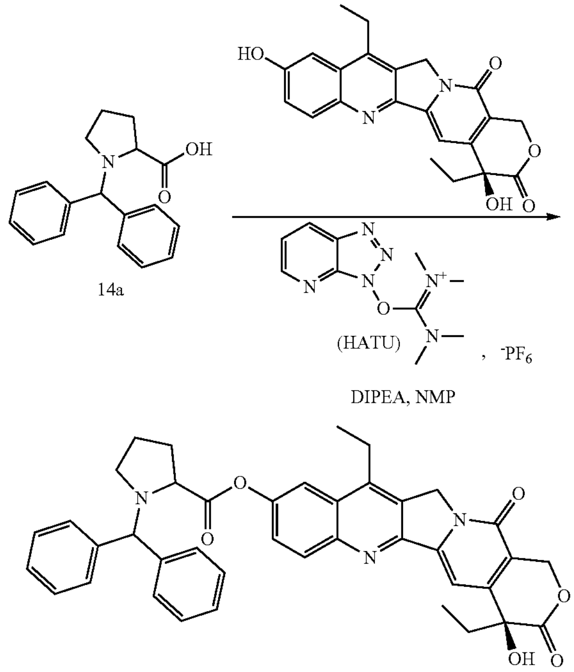

14

Benzhydrylproline (14a)

14a

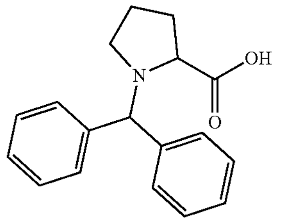

A reaction mixture of methyl prolinate hydrochloride (6.0 g, 36.2 mmol), chlorodiphenylmethane (8.1 g, 40.0 mmol), $K_2CO_3$ (15.0 g, 108.5 mmol) and KI (6.0 g, 36.1 mmol) in MeCN (120 mL) was stirred at 60° C. for 24 hours. The mixture was filtered and concentrated, the residue was dissolved in EtOAc and washed with water. The aqueous layer was extracted with EtOAc. The combined layers were washed with $Na_2S_2O_3$ aqueous solution, dried over $Na_2SO_4$, and concentrated to give the crude product of methyl benzhydrylprolinate (12.0 g), which was used for next step directly. MS-ESI (m/z): 296 $[M+1]^+$.

To a solution of the above crude product (12.0 g) in MeOH (50 mL), NaOH (4.9 g, 122.5 mmol) in water (50 mL) was added. The reaction was stirred at 50° C. for 17 hours. The mixture was concentrated at 45° C. under reduced pressure to remove MeOH and the leftover aqueous solution washed with methyl t-butyl ether. The aqueous phase was acidified with 1M HCl till pH=5-6 and extracted with DCM six times. The combined organic layers were dried over $Na_2SO_4$ and concentrated to give benzhydrylproline (14a) (7.8 g). MS-ESI (m/z): 282 $[M+1]^+$.

(S)-4,11-diethyl-4-hydroxy-3,14-dioxo-3,4,12,14-tetrahydro-1H-pyrano[3',4':6,7]indolizino[1,2-b]quinolin-9-yl benzhydrylprolinate (14)

14

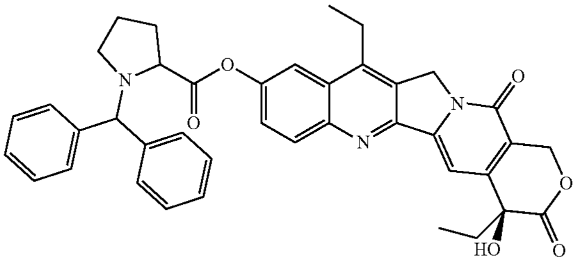

A mixture of (S)-4,11-diethyl-4,9-dihydroxy-1,12-dihydro-14H-pyrano[3',4':6,7]indolizino[1,2-b]quinoline-3,14(4H)-dione (50 mg, 0.13 mmol), benzhydrylproline (14a) (72 mg, 0.26 mmol), HATU (145 mg, 0.38 mmol), and DIPEA (135 μL, 0.76 mmol) in NMP (2 mL) was stirred at room temperature for 3.5 h. The reaction mixture was purified by preparative chromatography to give (S)-4,11-diethyl-4-hydroxy-3,14-dioxo-3,4,12,14-tetrahydro-1H-pyrano[3',4':6,7]indolizino[1,2-b]quinolin-9-yl benzhydrylprolinate (14) (31 mg). MS-ESI (m/z): 656 $[M+1]^+$. $^1$H NMR (400 MHz, DMSO-$d_6$) δ 8.16 (d, J=9.1 Hz, 1H), 7.56 (dd, J=5.3, 2.8 Hz, 5H), 7.44-7.21 (m, 8H), 5.42 (s, 2H), 5.33 (s, 2H), 5.04 (brs, 1H), 3.92 (brs, 1H), 3.16 (q, J=7.6 Hz, 2H), 3.00 (brs., 1H), 2.80-2.60 (m, 1H), 2.44-2.30 (m, 1H), 2.25-2.12 (m, 1H), 2.05-1.78 (m, 4H), 1.31 (t, J=7.5 Hz, 3H), 0.86 (t, J=7.3 Hz, 3H).

Example 15

(S)-4,11-diethyl-4-hydroxy-3,14-dioxo-3,4,12,14-tetrahydro-1H-pyrano[3',4':6,7]indolizino[1,2-b]quinolin-9-yl N-benzhydryl-P-methylphosphonamidate (15)

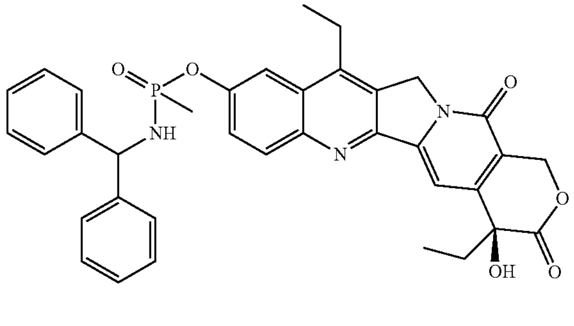 [SMILES: CCc1c2c(nc3ccc(OP(C)(=O)NC(c4ccccc4)c4ccccc4)cc13)-c1cc3c(c(=O)n1C2)COC(=O)[C@]3(O)CC]

Synthetic Route of 15

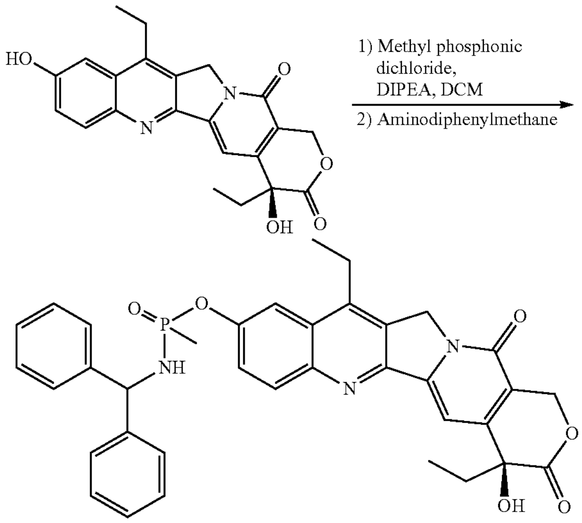

15

(S)-4,11-diethyl-4-hydroxy-3,14-dioxo-3,4,12,14-tetrahydro-1H-pyrano[3',4':6,7]indolizino[1,2-b]quinolin-9-yl N-benzhydryl-P-methylphosphonamidate (15)

15

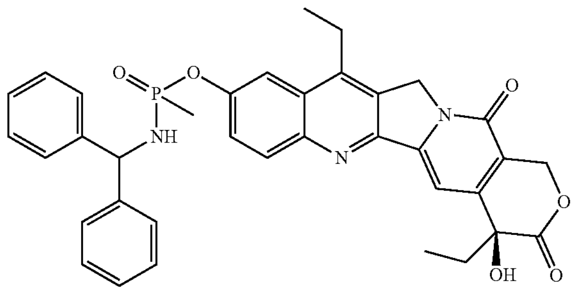

To a suspension of (S)-4,11-diethyl-4,9-dihydroxy-1,12-dihydro-14H-pyrano[3',4':6,7]indolizino[1,2-b]quinoline-3,14(4H)-dione (120 mg, 0.3 mmol) and DIPEA (280 μL, 1.6 mmol) in DCM (4 mL) was added methyl phosphonic dichloride (60 mg, 0.45 mmol). The reaction was stirred at room temperature for 45 minutes, followed by treatment with a solution of aminodiphenylmethane (80 μL, 0.46 mmol) and DIPEA (80 μL, 0.46 mmol) in DCM (1 mL). The mixture was stirred for 35 minutes and concentrated to dryness. The residue was purified by preparative chromatography to give (S)-4,11-diethyl-4-hydroxy-3,14-dioxo-3,4,12,14-tetrahydro-1H-pyrano[3',4':6,7]indolizino[1,2-b]quinolin-9-yl N-benzhydryl-P-methylphosphonamidate (15) (34 mg). MS-ESI (m/z): 636 $[M+1]^+$. $^1$H NMR (400 MHz, Chloroform-d) δ 8.10 (d, J=9.2 Hz, 1H), 7.81 (s, 1H), 7.66 (s, 1H), 7.50-7.43 (m, 1H), 7.35-6.98 (m, 10H), 5.80 (brs, 1H), 5.73 (d, J=16.3 Hz, 1H), 5.50 (t, J=9.75 Hz, 1H), 5.35-5.25 (m, 2H), 5.21 (s, 2H), 3.04-2.90 (m, 2H), 1.95-1.82 (m, 2H), 1.66 (d, J=16.7 Hz, 3H), 1.18 (t, J=7.0 Hz, 3H), 1.03 (t, J=7.3 Hz, 3H).

Example 16

(S)-4,11-diethyl-4-hydroxy-3,14-dioxo-3,4,12,14-tetrahydro-1H-pyrano[3',4':6,7]indolizino[1,2-b]quinolin-9-yl ((1-benzhydrylpyrrolidin-2-yl)methyl) carbamate (16)

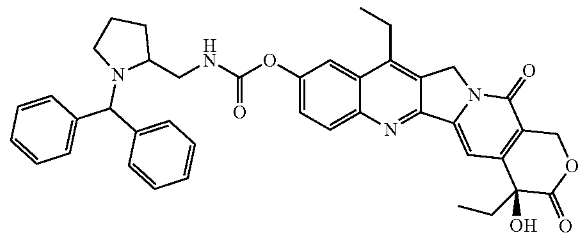 [SMILES: CCc1c2c(nc3ccc(OC(=O)NCC4CCCN4C(c4ccccc4)c4ccccc4)cc13)-c1cc3c(c(=O)n1C2)COC(=O)[C@]3(O)CC]

Synthetic Route of 16

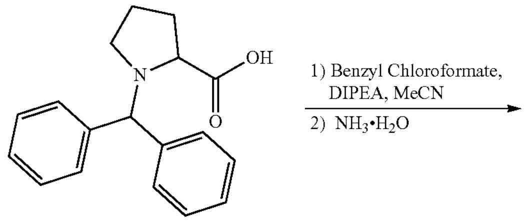

14a

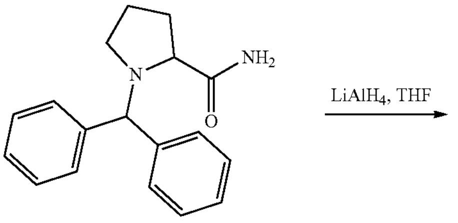

16a

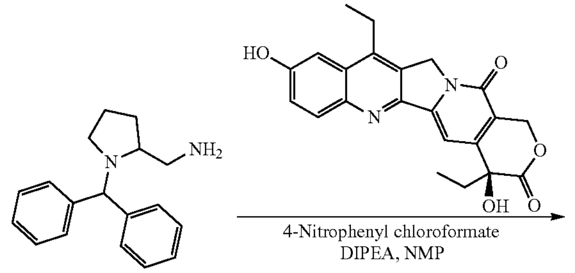

16b

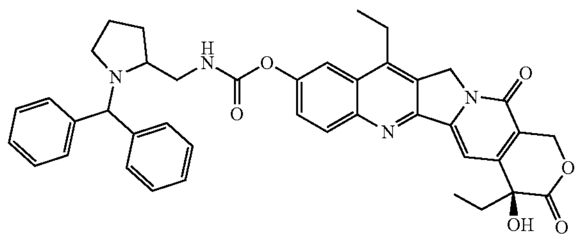

16

1-Benzhydrylpyrrolidine-2-carboxamide (16a)

16a

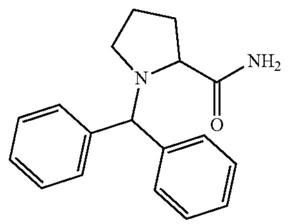

To a mixture of benzhydrylproline (14a) (1.0 g, 3.6 mmol) and DIPEA (2 mL, 11.5 mmol) in MeCN (20 mL) cooled in ice water was added benzyl chloroformate (0.8 mL, 5.6 mmol). The reaction was stirred for 3 h followed by treatment with ammonium hydroxide (4 mL) and then kept at room temperature for overnight. After removal of solvent, the crude product of 1-benzhydrylpyrrolidine-2-carboxamide (16a) was obtained as a brown oil, which was used for next step directly. MS-ESI (m/z): 281 $[M+1]^+$.

(1-Benzhydrylpyrrolidin-2-yl)methanamine (16b)

16b

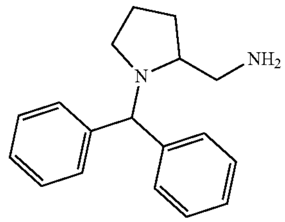

1-Benzhydrylpyrrolidine-2-carboxamide (16a) (3.6 mmol) was dissolved in THE (25 mL) followed by addition of 1M $LiAlH_4$-THF solution (22 mL, 22 mmol). The reaction was stirred for overnight and quenched with NaOH (aq.) solution. The mixture was filtered and the filtrate was evaporated to dryness. The residue was purified by column chromatography on silica gel (PE:EtOAc=10:1 to 5:1) to give the product of (1-benzhydrylpyrrolidin-2-yl)methanamine (16b) (600 mg). MS-ESI (m/z): 267 $[M+1]^+$.

(S)-4,11-diethyl-4-hydroxy-3,14-dioxo-3,4,12,14-tetrahydro-1H-pyrano[3',4':6,7]indolizino[1,2-b]quinolin-9-yl ((1-benzhydrylpyrrolidin-2-yl)methyl) carbamate (16)

16

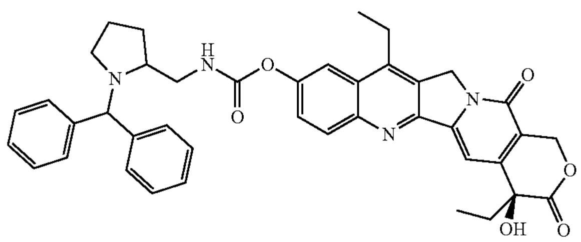

A solution of 4-nitrophenyl chloroformate (58 mg, 0.29 mmol) in NMP (0.25 mL) was added into a solution of (S)-4,11-diethyl-4,9-dihydroxy-1,12-dihydro-14H-pyrano[3',4':6,7]indolizino[1,2-b]quinoline-3,14(4H)-dione (50 mg, 0.13 mmol) and DIPEA (0.2 mL, 1.15 mmol) in NMP (1 mL) at −10° C. The mixture was stirred for 1.5 h followed by addition of (1-benzhydrylpyrrolidin-2-yl)methanamine (16b) (77 mg, 0.29 mmol) in NMP (0.25 mL). The reaction mixture was stirred for 2.5 h and purified by preparative chromatography to give (S)-4,11-diethyl-4-hydroxy-3,14-dioxo-3,4,12,14-tetrahydro-1H-pyrano[3',4':6,7]indolizino[1,2-b]quinolin-9-yl ((1-benzhydrylpyrrolidin-2-yl)methyl) carbamate (16) (36 mg). MS-ESI (m/z): 685 $[M+1]^+$. $^1$H NMR (400 MHz, Chloroform-d) δ 8.17 (d, J=9.2 Hz, 1H), 8.08 (s, 1H), 7.79-7.63 (m, 5H), 7.50-7.34 (m, 5H), 7.33-7.22 (m, 2H), 5.74 (d, J=16.3 Hz, 1H), 5.29 (d, J=26.2 Hz, 3H), 4.88 (s, 1H), 4.02 (s, 1H), 3.88-3.76 (m, 1H), 3.54 (dt, J=15.1, 7.2 Hz, 1H), 3.43-3.32 (m, 1H), 3.26-3.08 (m, 3H), 2.43-2.31 (m, 1H), 2.27-2.04 (m, 3H), 1.97-1.82 (m, 2H), 1.39 (t, J=7.6 Hz, 3H), 1.02 (t, J=7.3 Hz, 3H).

Example 17

(S)-4-(1-butylpiperidin-4-yl)phenyl (4,11-diethyl-4-hydroxy-3,14-dioxo-3,4,12,14-tetrahydro-1H-pyrano[3',4':6,7]indolizino[1,2-b]quinolin-9-yl) carbonate (17)

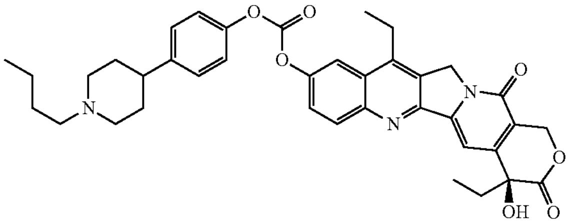 [SMILES: CCCCN1CCC(c2ccc(OC(=O)Oc3ccc4nc5c(c(CC)c4c3)Cn3c-5cc4c(c3=O)COC(=O)[C@]4(O)CC)cc2)CC1]

Synthetic Route of 17

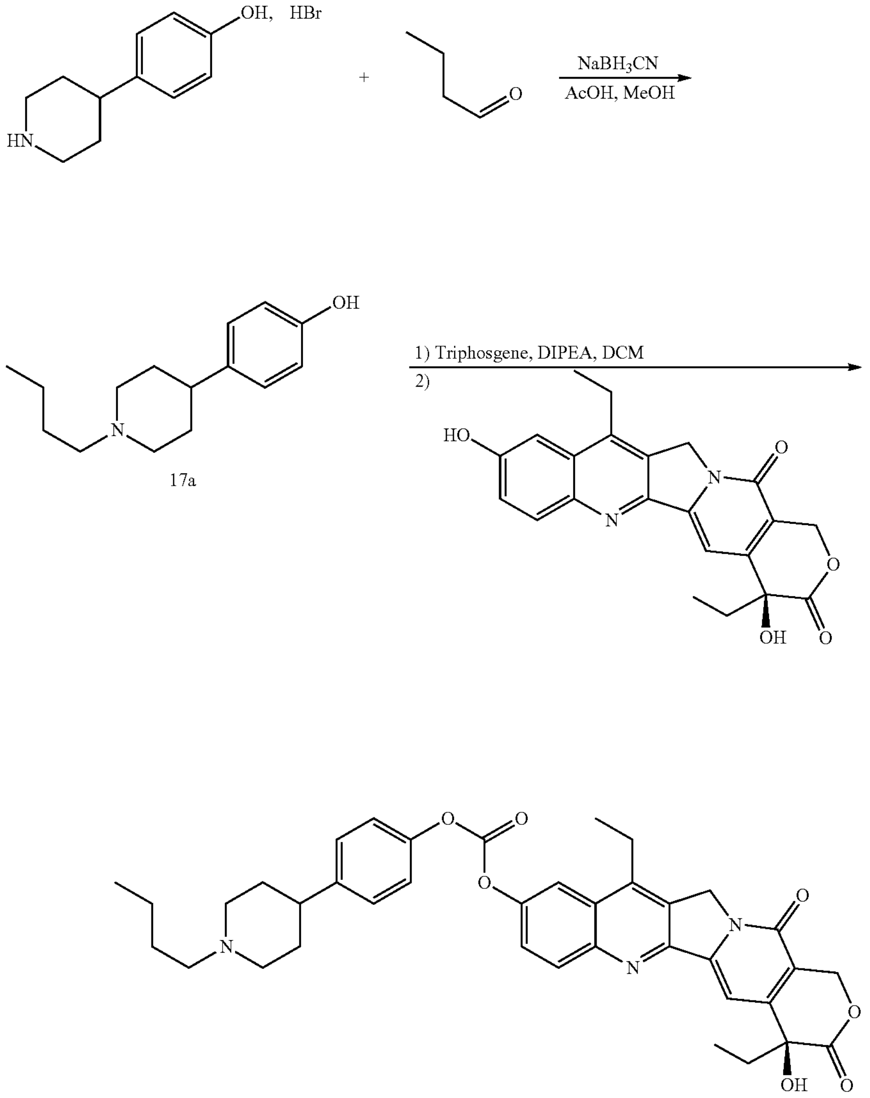

17a

17

4-(1-Butylpiperidin-4-yl)phenol (17a)

17a

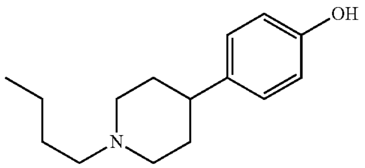

To a mixture of 4-(piperidin-4-yl)phenol hydrobromide (500 mg, 1.94 mmol), n-butyraldehyde (200 µ2.17 mmol) and AcOH (2 mL) in MeOH (20 mL) was added sodium cyanoborohydride (250 mg, 3.98 mmol), and the reaction was stirred at room temperature for overnight. The mixture was concentrated to remove MeOH, diluted with EtOAc (30 mL) and washed with $NaHCO_3$ (aq.) (30 mL). The aqueous layer was extracted with EtOAc (30 mL) and the combined organic layers were dried over $Na_2SO_4$, and evaporated to dryness to afford the crude product of 4-(1-butylpiperidin-4-yl)phenol (17a), which was used for next step directly (380 mg). MS-ESI (m/z): 234 $[M+1]^+$ (S)-4-(1-butylpiperidin-4-yl)phenyl (4,11-diethyl-4-hydroxy-3,14-dioxo-3,4,12,14-tetrahydro-1H-pyrano [3',4':6,7]indolizino[1,2-b]quinolin-9-yl) carbonate (17)

17

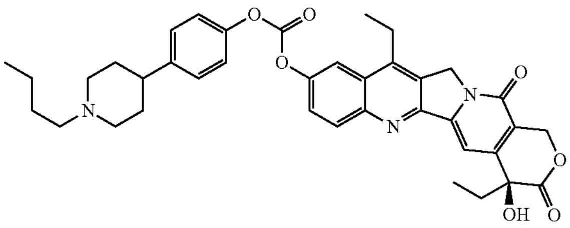

To a solution of 4-(1-butylpiperidin-4-yl)phenol (17a) (240 mg, 1.0 mmol) and DIPEA (1.9 mL, 10.9 mmol) in DCM (10 mL) cooled below −50° C. was added a solution of triphosgene (360 mg, 1.2 mmol) in DCM (3.6 mL). the mixture was stirred for 1 h followed by addition of (S)-4, 11-diethyl-4,9-dihydroxy-1,12-dihydro-14H-pyrano[3',4':6, 7]indolizino[1,2-b]quinoline-3,14(4H)-dione (300 mg, 0.76 mmol). The reaction was allowed to stirred at room temperature for 1 h. The reaction mixture was diluted with MeCN and purified by preparative chromatography to give (S)-4-(1-butylpiperidin-4-yl)phenyl (4,11-diethyl-4-hydroxy-3,14-dioxo-3,4,12,14-tetrahydro-1H-pyrano[3',4':6, 7]indolizi no[1,2-b]quinolin-9-yl) carbonate (17) (5 mg). MS-ESI (m/z): 652 $[M+1]^+$. $^1$H NMR (400 MHz, Chloroform-d) δ 8.27 (d, J=9.2 Hz, 1H), 8.04 (d, J=2.6 Hz, 1H), 7.72 (dd, J=9.4, 2.5 Hz, 1H), 7.65 (s, 1H), 7.36-7.09 (m, 4H), 5.75 (d, J=16.4 Hz, 1H), 5.35-5.24 (m, 3H), 3.80-3.69 (m, 2H), 3.17 (q, J=7.8 Hz, 2H), 3.05-2.65 (m, 4H), 2.43-2.22 (m, 1H), 2.08-1.65 (m, 8H), 1.48-1.16 (m, 5H), 1.08-0.86 (m, 6H).

Example 18

(S)-4,11-diethyl-4-hydroxy-3,14-dioxo-3,4,12,14-tetrahydro-1H-pyrano[3',4':6,7]indolizino[1,2-b] quinolin-9-yl ((1-heptylpiperidin-4-yl)methyl) carbonate (18)

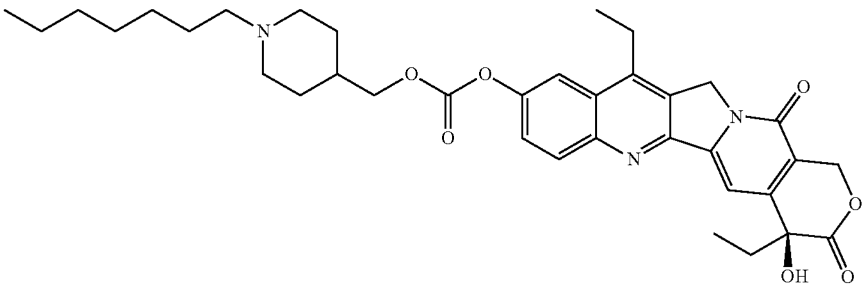 [SMILES: CCCCCCCN1CCC(COC(=O)Oc2ccc3nc4c(c(CC)c3c2)Cn2c-4cc3c(c2=O)COC(=O)[C@]3(O)CC)CC1]

Synthetic Route of 18

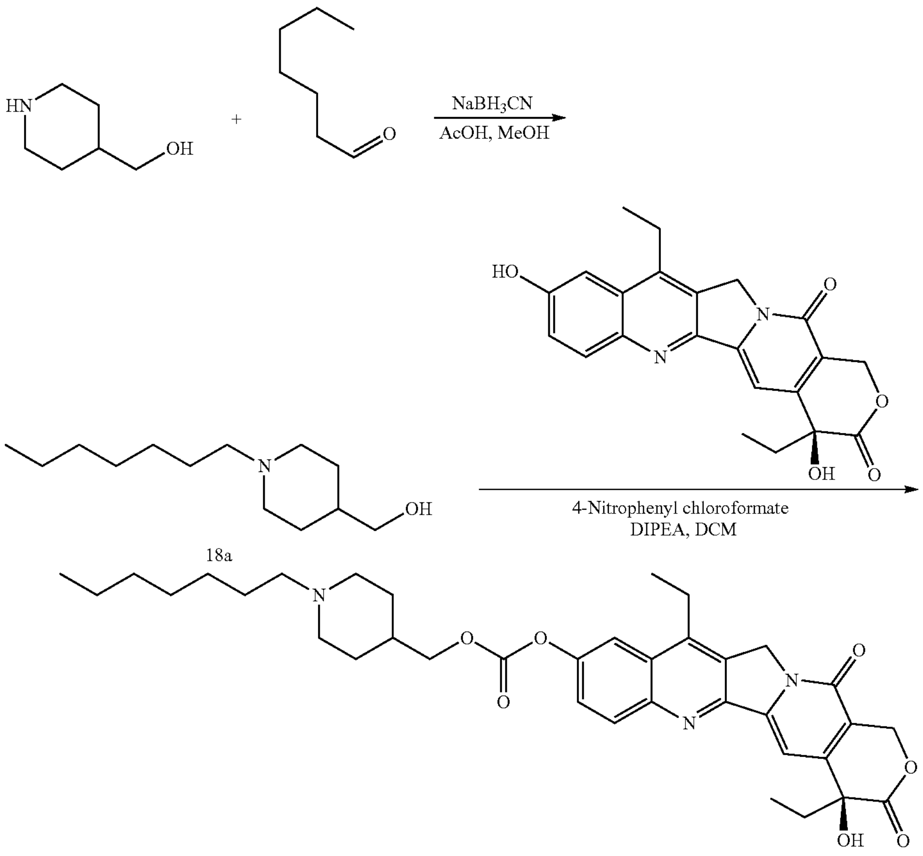

18

(1-Heptylpiperidin-4-yl)methanol (18a)

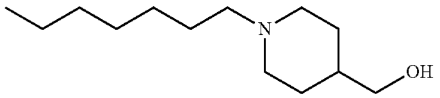

18a

To a mixture of piperidin-4-ylmethanol (2.0 g, 17.4 mmol), n-heptanal (2.0 g, 17.4 mmol) and AcOH (6 mL) in MeOH (60 mL) was added sodium cyanoborohydride (2.2 g, 34.8 mmol), and the reaction was stirred at room temperature for overnight. The mixture was distilled to remove MeOH and dissolved with EtOAc (100 mL) and washed with $NaHCO_3$ (aq.) (100 mL). The aqueous layer was extracted with EtOAc (100 mL) and the combined organic layers were dried over $Na_2SO_4$, and evaporated to dryness to afford the crude product of (1-heptylpiperidin-4-yl)methanol (18a), which was used for next step directly (3.8 g). MS-ESI (m/z): 214 $[M+1]^+$.

(S)-4,11-diethyl-4-hydroxy-3,14-dioxo-3,4,12,14-tetrahydro-1H-pyrano[3',4':6,7]indolizino[1,2-b]quinolin-9-yl ((1-heptylpiperidin-4-yl)methyl) carbonate (18)

18

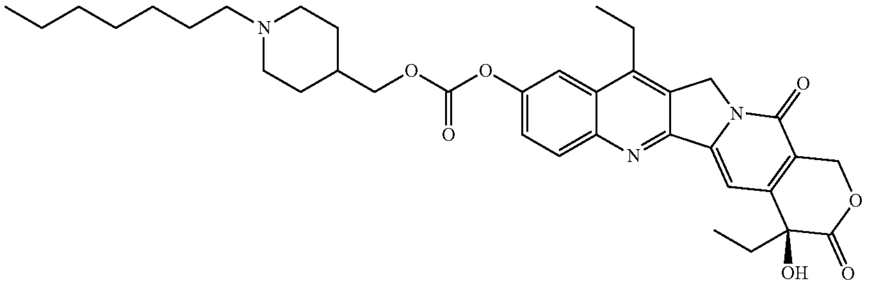

A solution of 4-nitrophenyl chloroformate (82 mg, 0.41 mmol) in NMP (0.3 mL) was added into a solution of (S)-4,11-diethyl-4,9-dihydroxy-1,12-dihydro-14H-pyrano[3',4':6,7]indolizino[1,2-b]quinoline-3,14(4H)-dione (55 mg, 0.14 mmol) and DIPEA (0.2 mL, 1.2 mmol) in NMP (1 mL) at −10° C. The mixture was stirred for 1 h followed by addition of (1-heptylpiperidin-4-yl)methanol (18a) (94 mg, 0.43 mmol) in NMP (0.2 mL). The reaction mixture was stirred for 4.5 h and purified by preparative chromatography to give (S)-4,11-diethyl-4-hydroxy-3,14-dioxo-3,4,12,14-tetrahydro-1H-pyrano[3',4':6,7]indolizino[1,2-b]quinolin-9-yl ((1-heptylpiperidin-4-yl)methyl) carbonate (18) (4 mg). MS-ESI (m/z): 632 $[M+1]^+$. $^1H$ NMR (400 MHz, Chloroform-d) δ 8.23 (d, J=9.2 Hz, 1H), 7.91 (s, 1H), 7.65 (s, 1H), 7.62 (d, J=9.2 Hz, 1H), 5.74 (d, J=16.3 Hz, 1H), 5.29 (d, J=24.0 Hz, 3H), 4.22 (d, J=5.6 Hz, 2H), 3.77 (d, J=11.9 Hz, 2H), 3.15 (q, J=7.7 Hz, 2H), 2.99 (s, 2H), 2.74-2.59 (m, 2H), 2.14-1.62 (m, 3H), 1.44-1.14 (m, 14H), 1.03 (t, J=7.4 Hz, 3H), 0.95-0.70 (m, 6H).

Example 19

(S)-4,11-diethyl-4-hydroxy-3,14-dioxo-3,4,12,14-tetrahydro-1H-pyrano[3',4':6,7]indolizino[1,2-b]quinolin-9-yl dicyclohexylglycinate (19)

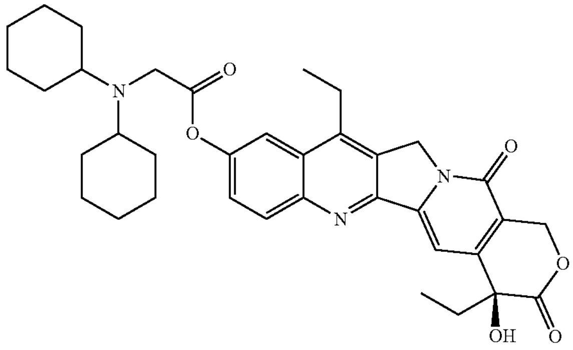 [SMILES: CCc1c2c(nc3ccc(OC(=O)CN(C4CCCCC4)C4CCCCC4)cc13)-c1cc3c(c(=O)n1C2)COC(=O)[C@]3(O)CC]

Synthetic Route of 19

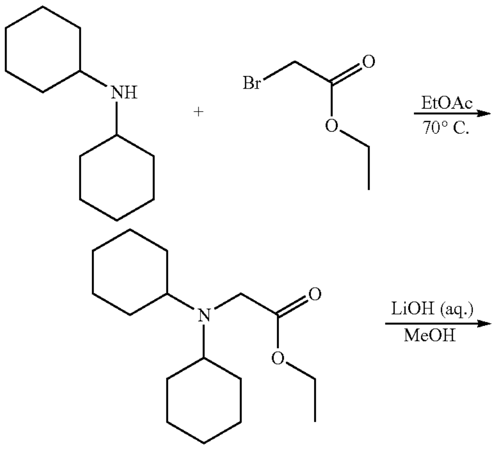

19a

-continued

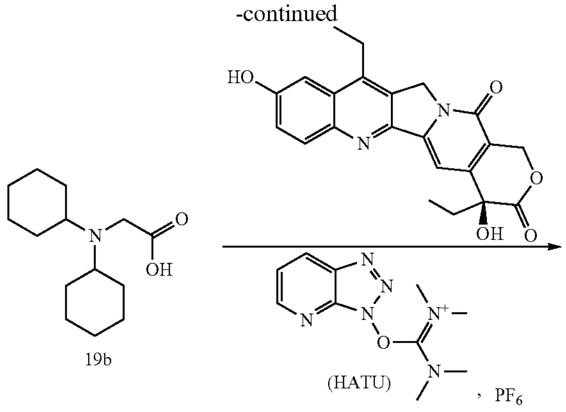

19b

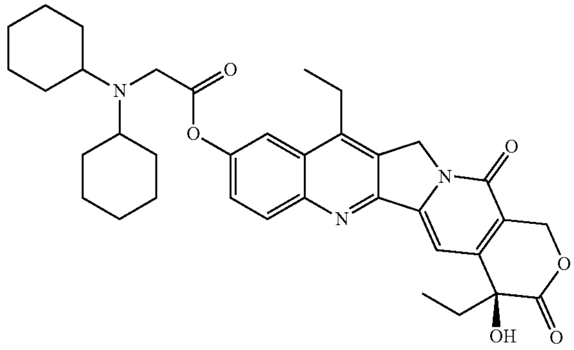

19

Ethyl dicyclohexylglycinate (19a)

A solution of dicyclohexylamine (3.66 g, 20.2 mmol) and ethyl 2-bromoacetate (1.67 g, 10 mmol) in EtOAc (20 mL) was heated at 70° C. for overnight. The mixture was filtered and the filtrate was concentrated to dryness. The residue was purified by column chromatography on silica gel (PE:EtOAc=10:1 to 3:1) to give the product of ethyl dicyclohexylglycinate (19a) (2.42 g). MS-ESI (m/z): 268 $[M+1]^+$.

Dicyclohexylglycine (19b)

To a solution of ethyl dicyclohexylglycinate (19a) (2.42 g, 9.1 mmol) in MeOH (5 mL) was added a solution of LiOH (650 mg, 27.1 mmol) in water (5 mL). The reaction mixture was stirred at 50° C. for overnight and concentrated under reduced pressure. The residue was diluted with water (30 mL) and EtOAc (60 mL), and acidified with formic acid (2 mL). The aqueous layer was extracted with EtOAc. The combined organic layers were dried over $Na_2SO_4$ and concentrated to give dicyclohexylglycine (19b) (870 mg). MS-ESI (m/z): 240 $[M+1]^+$.

(S)-4,11-diethyl-4-hydroxy-3,14-dioxo-3,4,12,14-tetrahydro-1H-pyrano[3',4':6,7]indolizino[1,2-b]quinolin-9-yl dicyclohexylglycinate (19)

19

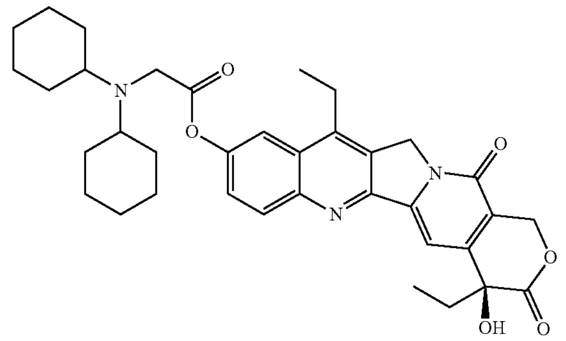

A mixture of dicyclohexylglycine (19b) (37 mg, 0.15 mmol), (S)-4,11-diethyl-4,9-dihydroxy-1,12-dihydro-14H-pyrano[3',4':6,7]indolizino[1,2-b]quinoline-3,14(4H)-dione (42 mg, 0.11 mmol), HATU (113 mg, 0.30 mmol) and DIPEA (105 μL, 0.60 mmol) in NMP (1 mL) was stirred at room temperature for overnight. The reaction mixture was purified by preparative chromatography to give (S)-4,11-diethyl-4-hydroxy-3,14-dioxo-3,4,12,14-tetrahydro-1H-pyrano[3',4':6,7]indolizino[1,2-b]quinolin-9-yl dicyclohexylglycinate (19) (6.4 mg). MS-ESI (m/z): 614 $[M+1]^+$. $^1H$ NMR (400 MHz, DMSO-$d_6$) δ 8.95 (s, 1H), 8.28 (d, J=9.1 Hz, 1H), 8.07 (d, J=2.5 Hz, 1H), 7.74 (dd, J=9.2, 2.5 Hz, 1H), 7.32 (s, 1H), 5.42 (s, 2H), 5.35 (s, 2H), 4.69 (s, 2H), 3.18 (q, J=7.7 Hz, 2H), 2.09-1.94 (m, 4H), 1.94-1.75 (m, 6H), 1.75-1.04 (m, 17H), 0.86 (t, J=7.3 Hz, 3H).

Example 20

(1-Benzhydrylpyrrolidin-2-yl)methyl ((S)-4-ethyl-4-hydroxy-3,14-dioxo-3,4,12,14-tetrahydro-1H-pyrano[3',4':6,7]indolizino[1,2-b]quinolin-9-yl) carbonate (20)

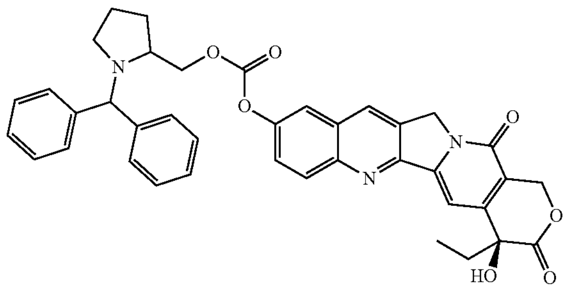 [SMILES: CC[C@@]1(O)C(=O)OCc2c1cc1n(c2=O)Cc2cc3cc(OC(=O)OCC4CCCN4C(c4ccccc4)c4ccccc4)ccc3nc2-1]

Synthetic Route of 20

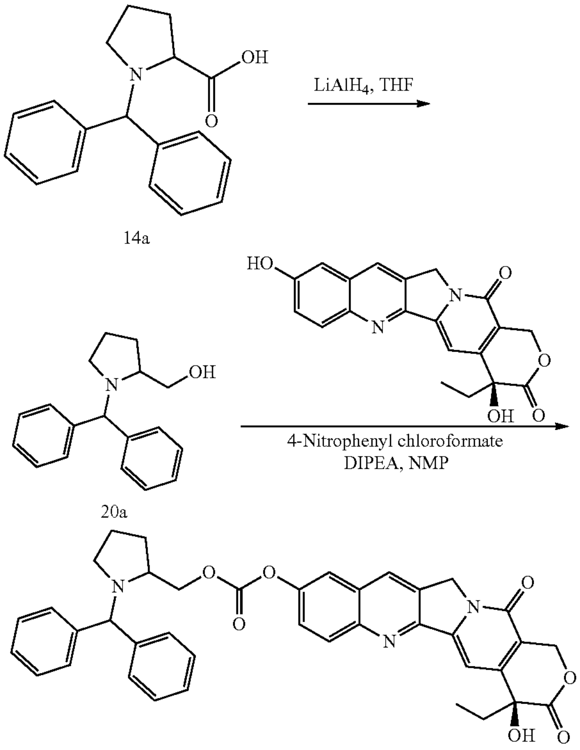

14a

20a

20

(1-Benzhydrylpyrrolidin-2-yl)methanol (20a)

1M $LiAlH_4$-THF (10 mL, 10 mmol) was added dropwise into a solution of benzhydrylproline (14a) (1.0 g, 3.6 mmol) in THE (20 mL). The reaction mixture was quenched with $NaHCO_3$ (aq.) and extracted with EtOAc twice. The organic layers were combined, dried over $Na_2SO_4$ and concentrated under reduced pressure to provide (1-benzhydrylpyrrolidin-2-yl)methanol (20a) (900 mg). MS-ESI (m/z): 268 $[M+1]^+$.

(1-Benzhydrylpyrrolidin-2-yl)methyl ((S)-4-ethyl-4-hydroxy-3,14-dioxo-3,4,12,14-tetrahydro-1H-pyrano[3',4':6,7]indolizino[1,2-b]quinolin-9-yl) carbonate (20)

20

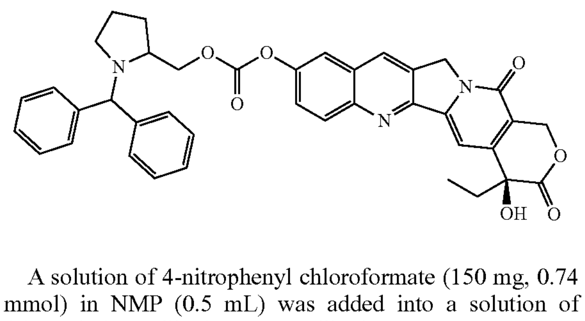

A solution of 4-nitrophenyl chloroformate (150 mg, 0.74 mmol) in NMP (0.5 mL) was added into a solution of (S)-4-ethyl-4,9-dihydroxy-1,12-dihydro-14H-pyrano[3',4':6,7]indolizino[1,2-b]quinoline-3,14(4H)-dione (100 mg, 0.27 mmol) and DIPEA (0.4 mL, 2.3 mmol) in NMP (1 mL) at −10° C. The mixture was stirred for 2 h followed by addition of (1-benzhydrylpyrrolidin-2-yl)methanol (20a) (98 mg, 0.37 mmol) and DMAP (54 mg, 0.46 mmol) in NMP (0.5 mL). The reaction mixture was stirred for 1 h and purified by preparative chromatography to give (1-benzhydrylpyrrolidin-2-yl)methyl ((S)-4-ethyl-4-hydroxy-3,14-dioxo-3,4,12,14-tetrahydro-1H-pyrano[3',4':6,7]indolizino[1,2-b]quinolin-9-yl) carbonate (20) (30 mg). MS-ESI (m/z): 658 $[M+1]^+$. $^1H$ NMR (400 MHz, Chloroform-d) δ 8.36 (s, 1H), 8.22 (d, J=9.2 Hz, 1H), 7.78 (d, J=2.6 Hz, 1H), 7.76-7.66 (m, 5H), 7.59 (dd, J=9.2, 2.5 Hz, 1H), 7.50-7.33 (m, 6H), 5.74 (d, J=16.4 Hz, 1H), 5.35-5.26 (m, 3H), 5.05 (s, 1H), 4.46-4.36 (m, 2H), 4.10 (brs, 1H), 4.12-3.80 (m, 2H), 3.24 (s, 1H), 2.48-2.36 (m, 1H), 2.36-2.26 (m, 1H), 2.23-2.08 (m, 2H), 1.98-1.82 (m, 2H), 1.03 (t, J=7.4 Hz, 3H).

Example 21

4-((1-Benzhydrylpiperidin-4-yl)methyl)phenyl (3-methyl-4-oxo-3,4-dihydroimidazo[5,1-d][1,2,3,5]tetrazine-8-carbonyl)carbamate (21)

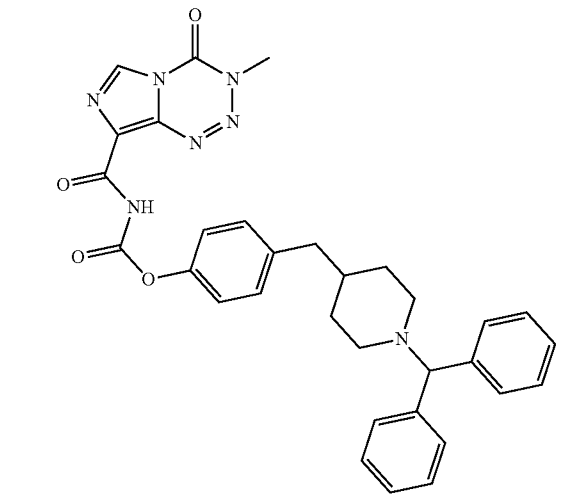 [SMILES: Cn1nnc2c(C(=O)NC(=O)Oc3ccc(CC4CCN(C(c5ccccc5)c5ccccc5)CC4)cc3)ncn2c1=O]

Synthetic Route of 21

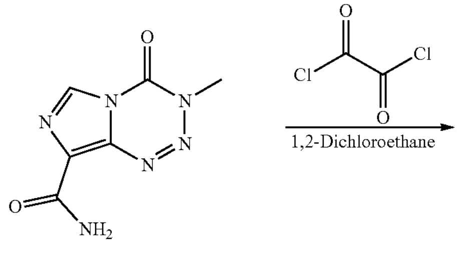

-continued

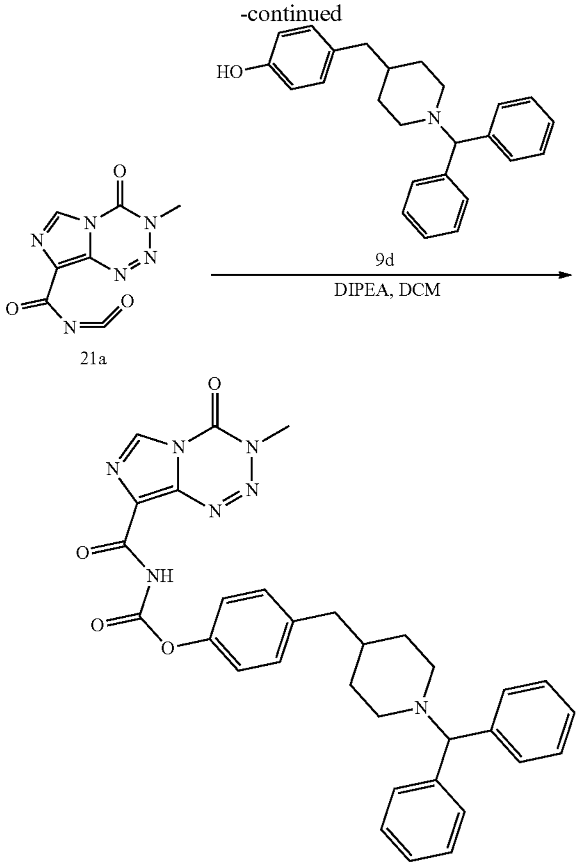

3-Methyl-4-oxo-3,4-dihydroimidazo[5,1-d][1,2,3,5]tetrazine-8-carbonyl isocyanate (21a)

A mixture of temozolomide (200 mg, 1.0 mmol) and oxalyl chloride (175 μL, 2.1 mmol) in 1,2-dichloroethane (25 mL) was stirred at 85° C. for 4 h. The reaction mixture was concentrated under reduced pressure to give 3-methyl-4-oxo-3,4-dihydroimidazo[5,1-d][1,2,3,5]tetrazine-8-carbonyl isocyanate (21a), which was used for next step directly. MS-ESI (m/z): 275 $[M+MeOH+Na]^+$ (Sample quenched with MeOH).

4-((1-Benzhydrylpiperidin-4-yl)methyl)phenyl (3-methyl-4-oxo-3,4-dihydroimidazo[5,1-d][1,2,3,5]tetrazine-8-carbonyl)carbamate (21)

A mixture of 3-methyl-4-oxo-3,4-dihydroimidazo[5,1-d][1,2,3,5]tetrazine-8-carbonyl isocyanate (21a) (1 mmol) in DCM was added into a solution of 4-((1-benzhydrylpiperidin-4-yl)methyl)phenol (9d) (1 mmol) and DIPEA (900 μL, 5.2 mmol) in DCM (10 mL). The reaction mixture was stirred at room temperature for 1.5 h followed by evaporation. The residue was purified by preparative chromatography to give 4-((1-Benzhydrylpiperidin-4-yl)methyl)phenyl (3-methyl-4-oxo-3,4-dihydroimidazo[5,1-d][1,2,3,5]tetrazine-8-carbonyl)carbamate (21) (109 mg). MS-ESI (m/z): 578 $[M+1]^+$. $^1H$ NMR (400 MHz, Chloroform-d) δ 9.63 (s, 1H), 8.46 (s, 1H), 7.69-7.56 (m, 4H), 7.43-7.31 (m, 6H), 7.19-7.04 (m, 4H), 4.89 (s, 1H), 4.08 (s, 3H), 3.47 (d, J=12.0 Hz, 2H), 2.63-2.46 (m, 4H), 1.92-1.64 (m, 5H).

Example 22

4-((1-benzhydrylpiperidin-4-yl)methyl)phenyl (3-methyl-4-oxo-3,4-dihydroimidazo[5,1-d][1,2,3,5]tetrazine-8-carbonyl)carbamate (22)

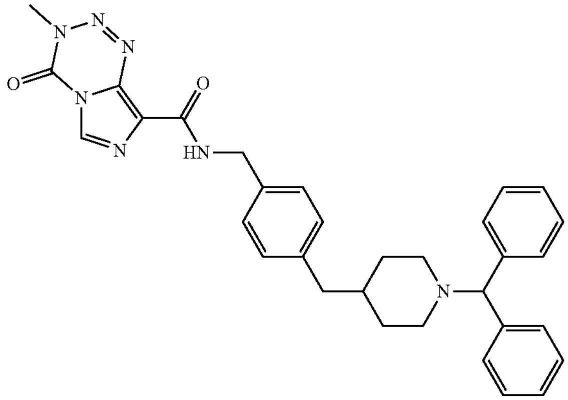

Synthetic Route of 22

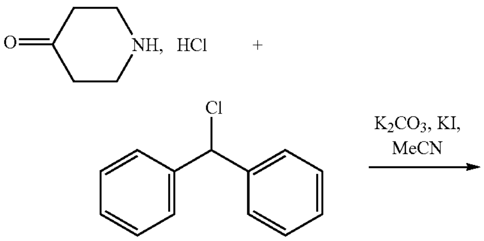

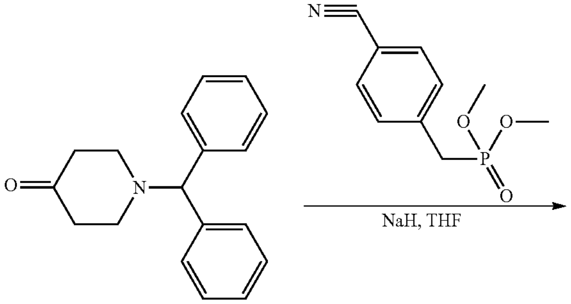

22a

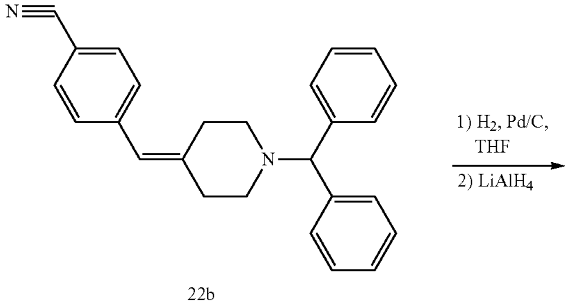

22b

-continued

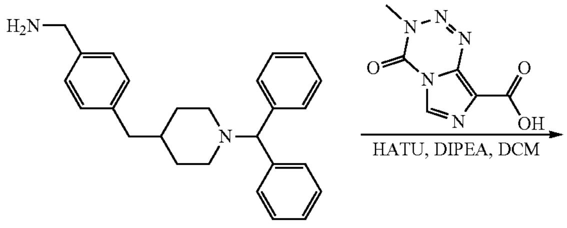

22c

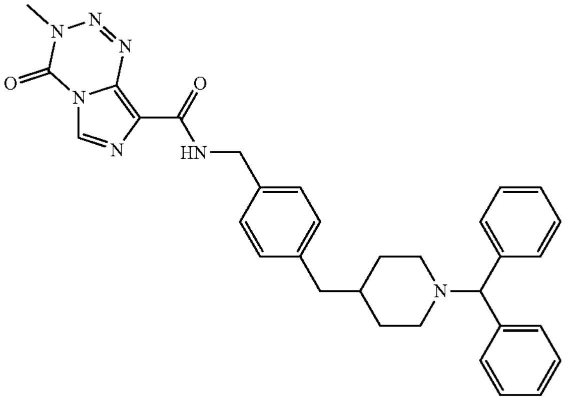 [SMILES: Cn1nnc2c(C(=O)NCc3ccc(CC4CCN(C(c5ccccc5)c5ccccc5)CC4)cc3)ncn2c1=O]

22

1-Benzhydrylpiperidin-4-one (22a)

22a

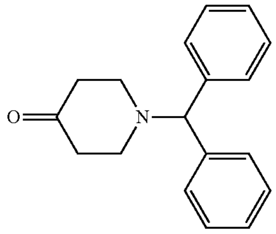

A suspension of 4-piperidinonehydrochloride (1.0 g, 7.4 mmol), (chloromethylene)dibenzene (1.57 g, 7.7 mmol), $K_2CO_3$ (22.1 mmol) and KI (7.4 mmol) in MeCN (30 mL) was stirred at 60° C. for overnight. The mixture was filtered and the filtrate was concentrated to dryness. The residue was dissolved with EtOAc (50 mL) and washed with water (50 mL) and the organic layer was dried over $Na_2SO_4$ evaporated to dryness to give the crude product of 1-benzhydrylpiperidin-4-one (22a) (2.2 g), which was used for next step directly. MS-ESI (m/z): 266 $[M+1]^+$.

4-((1-Benzhydrylpiperidin-4-ylidene)methyl)benzonitrile (22b)

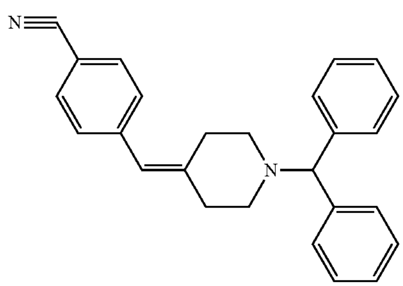

22b

To a solution of dimethyl (4-cyanobenzyl)phosphonate (2.2 g, 9.8 mmol) in THE (20 mL) cooled at −50° C. was added 60% NaH (2.3 g) in portions and then followed by addition of 1-benzhydrylpiperidin-4-one (22a) (7.7 mmol) in THE (20 mL). The reaction was stirred for 4 h and quenched with water (100 mL). The mixture was extracted with EtOAc twice and the combined organic layers was dried over $Na_2SO_4$ and evaporated to dryness to give 4-((1-Benzhydrylpiperidin-4-ylidene)methyl)benzonitrile (22b). MS-ESI (m/z): 365 $[M+1]^+$.

(4-((1-Benzhydrylpiperidin-4-yl)methyl)phenyl) methanamine (22c)

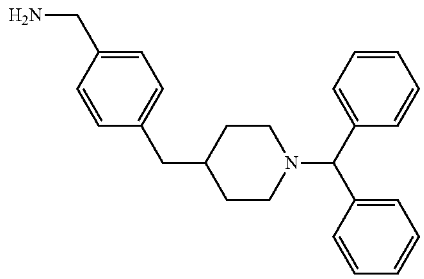

22c

A suspension of 4-((1-benzhydrylpiperidin-4-ylidene) methyl)benzonitrile (22b) (1.4 g, 3.8 mmol) and 10% Pd/C (200 mg) in THE (20 mL) was degassed under vacuum and purged with $H_2$ several times. The mixture was stirred with a $H_2$ balloon at room temperature for overnight. The suspension was filtered and to the filtrate was added $LiAlH_4$ (50 mmol) in THF (35 mL). The reaction was stirred for 3.5 h followed by addition of 2 mL of NaOH (aq.), the suspension was filtered and the filter cake was washed with EtOAc. The combined filtrates were concentrated to dryness to give (4-((1-benzhydrylpiperidin-4-yl)methyl)phenyl)methanamine (22c) (1.26 g), which was used for next step directly. MS-ESI (m/z): 371 $[M+1]^+$.

N-(4-((1-benzhydrylpiperidin-4-yl)methyl)benzyl)-3-methyl-4-oxo-3,4-dihydroimidazo[5,1-d][1,2,3,5]tetrazine-8-carboxamide (22)

22

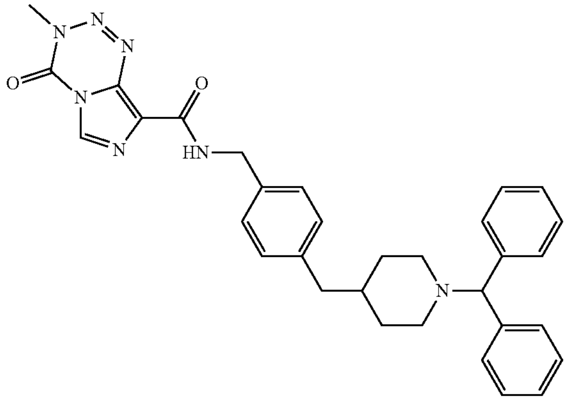

To a solution of 3-methyl-4-oxo-3,4-dihydroimidazo[5,1-d][1,2,3,5]tetrazine-8-carboxylic acid (200 mg, 1.0 mmol) and DIPEA (1 mL, 5.7 mmoL) in DCM (20 mL) was added HATU (1.15 g, 3.0 mmol) and (4-((1-benzhydrylpiperidin-4-yl)methyl)phenyl)methanamine (22c) (400 mg, 1.1 mmol). The reaction was stirred at room temperature for 3 h followed by addition of water and DCM. The organic layer was dried over $Na_2SO_4$ and evaporated to dryness. The crude product was purified by silica gel chromatography and preparative chromatography to give N-(4-((1-benzhydrylpiperidin-4-yl)methyl)benzyl)-3-methyl-4-oxo-3,4-dihydroimidazo[5,1-d][1,2,3,5]tetrazine-8-carboxamide (22) (43 mg). MS-ESI (m/z): 548 $[M+1]^+$. $^1H$ NMR (400 MHz, Chloroform-d) δ 8.37 (s, 1H), 7.68-7.57 (m, 4H), 7.43-7.31 (m, 6H), 7.22 (d, J=7.7 Hz, 2H), 7.02 (d, J=7.6 Hz, 2H), 4.69-4.60 (m, 2H), 4.02 (s, 3H), 3.55-3.42 (m, 4H), 2.56-2.46 (m, 3H), 1.96-1.55 (m, 5H).

Example 23

(2S,3S,4S,6R)-6-(((1S,3S)-3-acetyl-3,5,12-trihydroxy-10-methoxy-6,11-dioxo-1,2,3,4,6,11-hexahydrotetracen-1-yl)oxy)-2-methyl-4-(((4-((4-methylpiperazin-1-yl)methyl)phenoxy)carbonyl)amino) tetrahydro-2H-pyran-3-yl acetate (23)

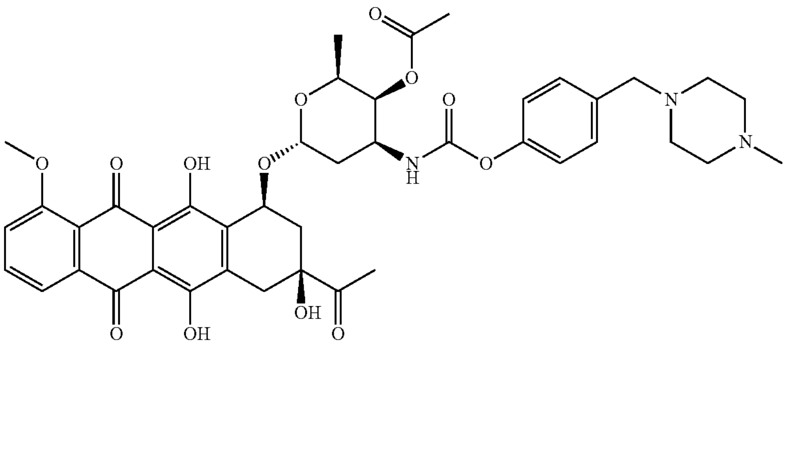

Synthetic Route of 23

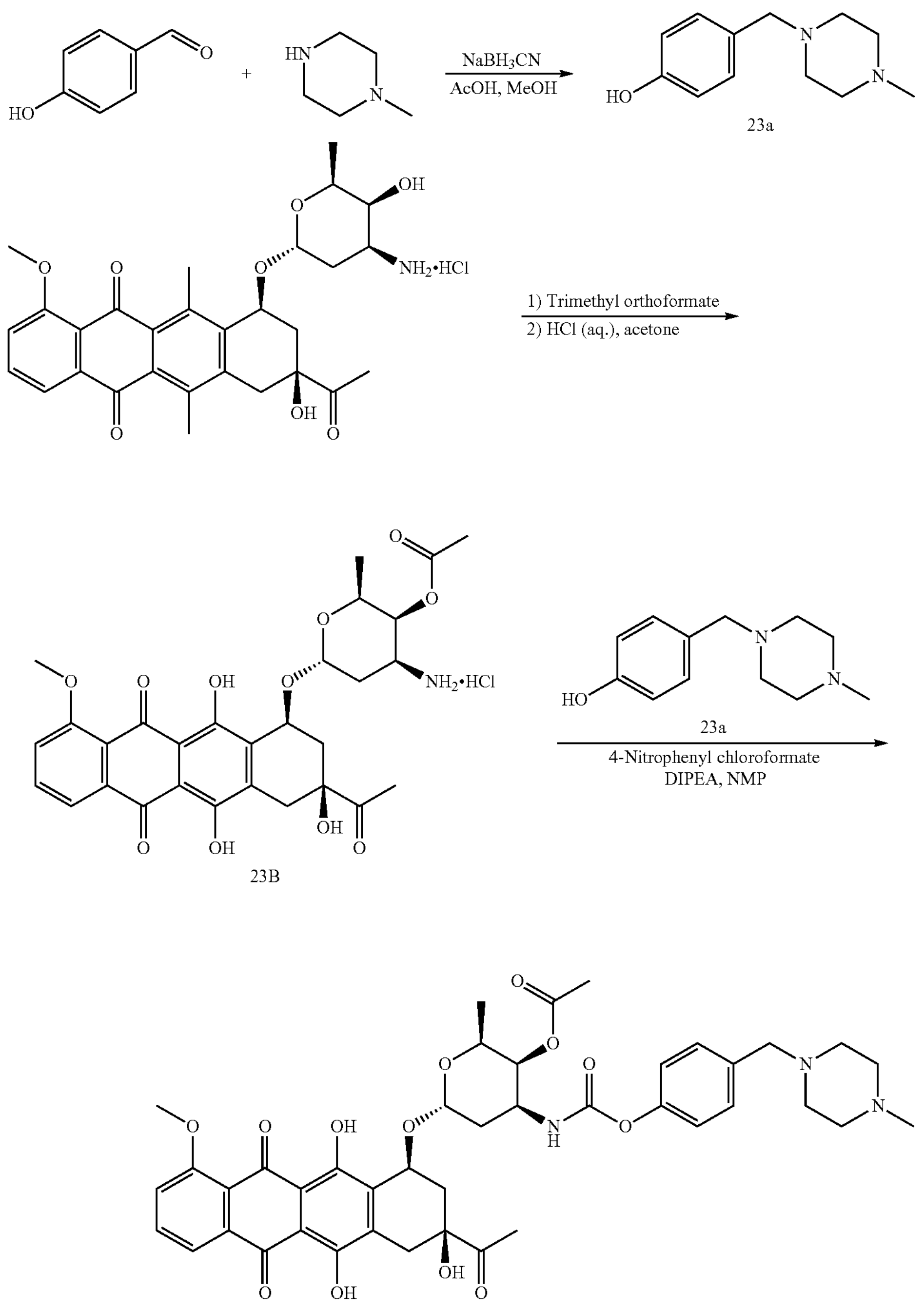

23a

23B

23

4-((4-Methylpiperazin-1-yl)methyl)phenol (23a)

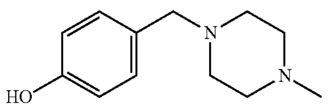

23a

A mixture of 4-hydroxybenzaldehyde (2.0 g, 20 mmol), 1-methylpiperazine (2.44 g, 20 mmol), AcOH (8 mL) and $NaBH_3CN$ (2.51 g, 40 mmol) in MeOH (80 mL) was stirred at room temperature for overnight. The reaction mixture was evaporated to dryness and dissolved with EtOAc (50 mL) and $NaHCO_3$ (aq.) (50 mL). The organic layer was dried over $Na_2SO_4$ and evaporated to dryness to give 4-((4-methylpiperazin-1-yl)methyl)phenol (23a) (2.37 g), which was used for next step directly. MS-ESI (m/z): 207 $[M+1]^+$.

(2S,3R,4S,6R)-6-(((1S,3S)-3-acetyl-3,5,12-trihydroxy-10-methoxy-6,11-dioxo-1,2,3,4,6,11-hexahydrotetracen-1-yl)oxy)-4-(12-chloraneyl)-2-methyltetrahydro-2H-pyran-3-yl acetate hydrochloride (23b)

23b

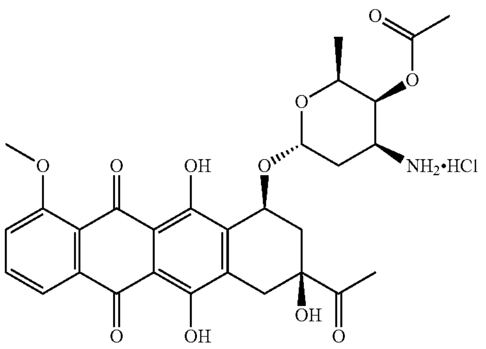

A suspension of daunorubicin hydrochloride (656 mg, 1.24 mmol) in trimethyl orthoformate (10 mL) was heated at 110° C. for 3 h. The reaction was concentrated under reduced pressure. The residue was diluted with acetone (40 mL) followed by addition of 1N HCl (4 mL) and conc. HCl (0.1 mL). The mixture was evaporated to dryness and re-crystallization from MeOH (4 mL), EtOAc (40 mL) and PE (40 mL) to give (2S,3R,4S,6R)-6-(((1S,3S)-3-acetyl-3,5,12-trihydroxy-10-methoxy-6,11-dioxo-1,2,3,4,6,11-hexahydrotetracen-1-yl)oxy)-4-(12-chloraneyl)-2-methyltetrahydro-2H-pyran-3-yl acetate hydrochloride (23b) (622 mg). MS-ESI (m/z): 570 $[M+1]^+$.

(2S,3S,4S,6R)-6-(((1S,3S)-3-acetyl-3,5,12-trihydroxy-10-methoxy-6,11-dioxo-1,2,3,4,6,11-hexahydrotetracen-1-yl)oxy)-2-methyl-4-(((4-((4-methylpiperazin-1-yl)methyl)phenoxy)carbonyl)amino)tetrahydro-2H-pyran-3-yl acetate (23)

23

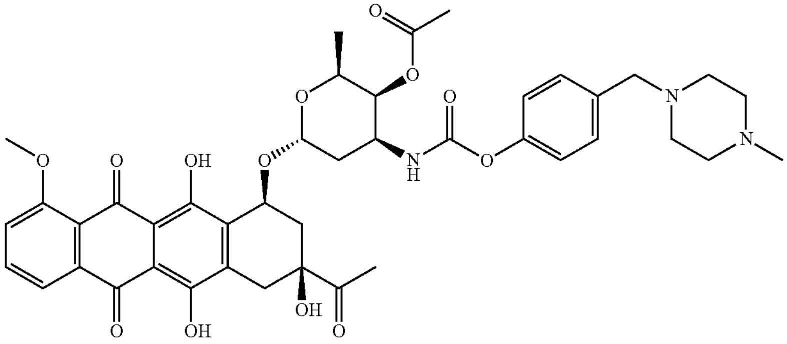 [SMILES: COc1cccc2c1C(=O)c1c(O)c3c(c(O)c1C2=O)C[C@@](O)(C(C)=O)C[C@@H]3O[C@H]1C[C@H](NC(=O)Oc2ccc(CN3CCN(C)CC3)cc2)[C@H](OC(C)=O)[C@H](C)O1]

A solution of 4-nitrophenyl chloroformate (80 mg, 0.2 mmol) in NMP (0.5 mL) was added into a solution of 4-((4-methylpiperazin-1-yl)methyl)phenol (23a) (40 mg, 0.1 mmol) and DIPEA (90 μL, 0.5 mmol) in NMP (1 mL) at −10° C. The mixture was stirred for 4 h followed by addition of (2S,3R,4S,6R)-6-(((1S,3S)-3-acetyl-3,5,12-trihydroxy-10-methoxy-6,11-dioxo-1,2,3,4,6,11-hexahydrotetracen-1-yl)oxy)-4-(12-chloraneyl)-2-methyltetrahydro-2H-pyran-3-yl acetate hydrochloride (23b) (50 mg, 0.083 mmol) in NMP (0.5 mL). The reaction mixture was stirred for 1 h and purified by preparative chromatography to give (2S,3S,4S,6R)-6-(((1S,3S)-3-acetyl-3,5,12-trihydroxy-10-methoxy-6,11-dioxo-1,2,3,4,6,11-hexahydrotetracen-1-yl)oxy)-2-methyl-4-(((4-((4-methylpiperazin-1-yl)methyl)p henoxy)carbonyl)amino)tetrahydro-2H-pyran-3-yl acetate (23) (25 mg). MS-ESI (m/z): 802 $[M+1]^+$. $^1H$ NMR (400 MHz, DMSO-$d_6$) δ 13.26 (s, 1H), 7.95-7.84 (m, 3H), 7.69-7.62 (m, 1H), 7.29 (d, J=8.2 Hz, 2H), 7.02 (d, J=8.2 Hz, 2H), 5.54 (brs, 1H), 5.33 (s, 1H), 5.02-4.92 (m, 2H), 4.39 (q, J=5.6 Hz, 1H), 3.97 (s, 3H), 4.15-3.55 (m, 10H), 3.35 (brs, 1H), 2.98 (brs, 1H), 2.93 (s, 2H), 2.73 (s, 2H), 2.33-2.05 (m, 8H), 1.95-1.83 (m, 1H), 1.68-1.56 (m, 1H), 1.03 (d, J=6.4 Hz, 3H).

Example 24

(5-Fluoro-2,4-dioxo-3,4-dihydropyrimidin-1(2H)-yl)methyl hexyl carbonate (24)

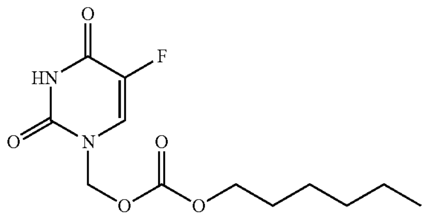 [SMILES: CCCCCCOC(=O)OCn1cc(F)c(=O)[nH]c1=O]

Synthetic Route of 24

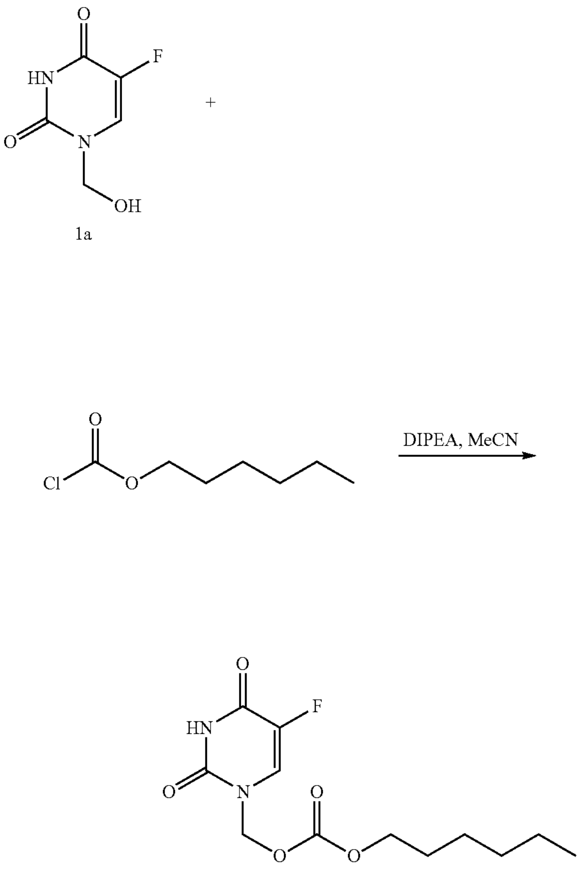

1a

24

(5-Fluoro-2,4-dioxo-3,4-dihydropyrimidin-1(2H)-yl) methyl hexyl carbonate (24)

24

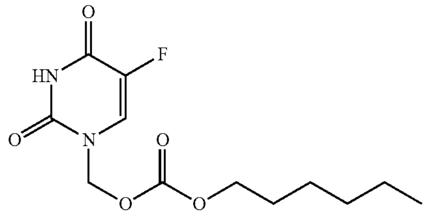

To a solution of 5-fluoro-1-(hydroxymethyl)pyrimidine-2,4(1H,3H)-dione (1a) (640 mg) and hexyl carbonochloridate (165 μL, 1.0 mmol) in MeCN (5 mL) was added DIPEA (1 mL, 5.6 mmol). The reaction was stirred at room temperature for 2 h followed by prep. HPLC purification to afford (5-fluoro-2,4-dioxo-3,4-dihydropyrimidin-1(2H)-yl) methyl hexyl carbonate (24). MS-ESI (m/z): 289 $[M+1]^+$. $^1H$ NMR (400 MHz, DMSO-$d_6$) δ 12.01 (s, 1H), 8.12 (d, J=6.6 Hz, 1H), 5.56 (s, 2H), 4.09 (t, J=6.6 Hz, 2H), 1.61-1.52 (m, 2H), 1.31-1.18 (m, 6H), 0.87-0.79 (m, 3H).

Example 25

(5-Fluoro-2,4-dioxo-3,4-dihydropyrimidin-1(2H)-yl) methyl (4-methoxyphenyl) carbonate (25)

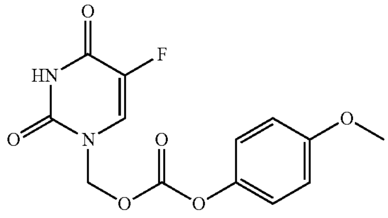

Synthetic Route of 25

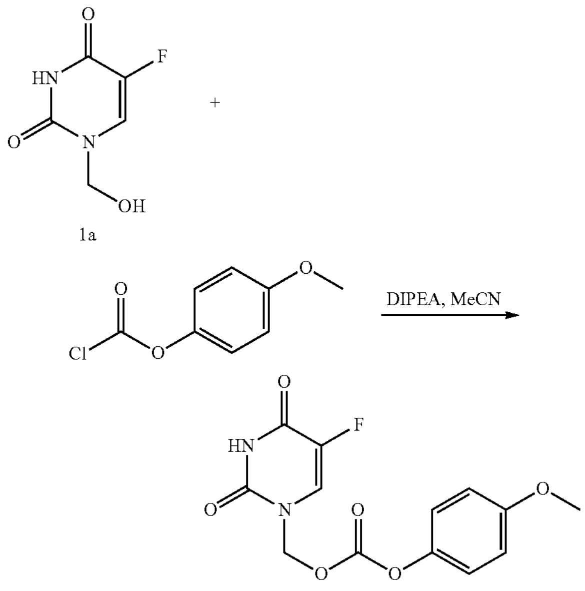

1a

25

(5-Fluoro-2,4-dioxo-3,4-dihydropyrimidin-1(2H)-yl) methyl (4-methoxyphenyl) carbonate (25)

25

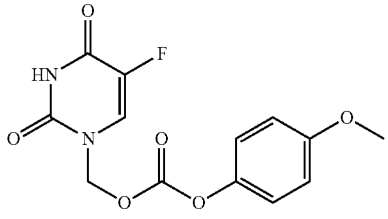 [SMILES: COc1ccc(OC(=O)OCn2cc(F)c(=O)[nH]c2=O)cc1]

The title compound (25) was prepared according to the method of Example 24 by using 4-methoxyphenyl carbonochloridate instead of hexyl carbonochloridate. MS-ESI (m/z): 311 $[M+1]^+$.

Example 26

(5-Fluoro-2,4-dioxo-3,4-dihydropyrimidin-1(2H)-yl) methyl 4-(1-(2,2-diphenylethyl)piperidin-4-yl)benzoate (26)

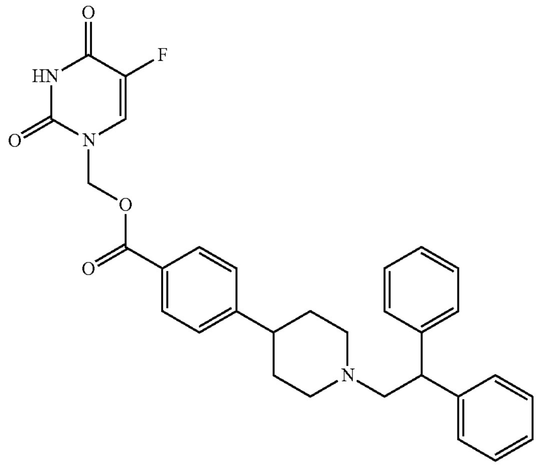

Synthetic Route of 26

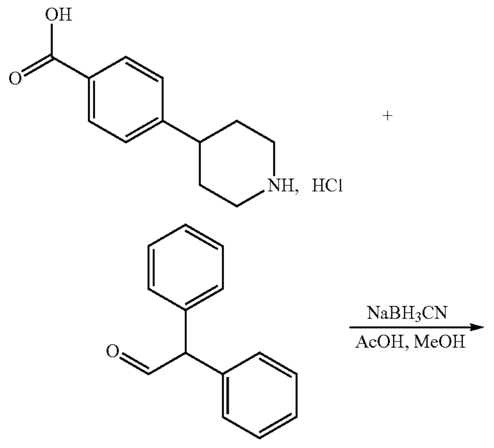

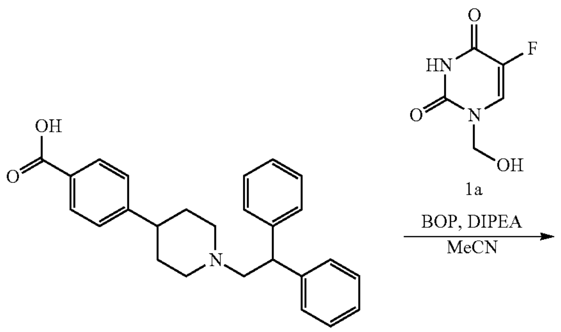

26a

-continued

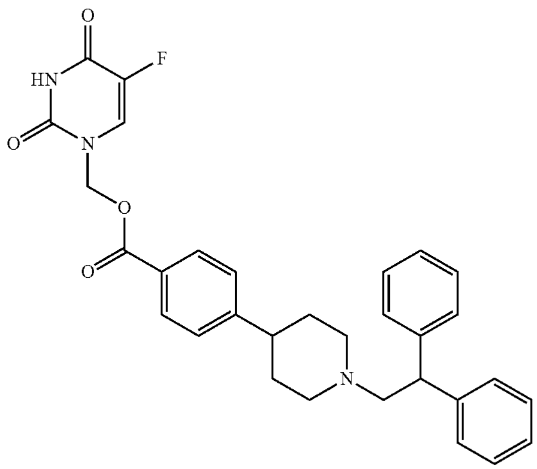 [SMILES: O=C(OCn1cc(F)c(=O)[nH]c1=O)c1ccc(C2CCN(CC(c3ccccc3)c3ccccc3)CC2)cc1]

26

4-(1-(2,2-Diphenylethyl)piperidin-4-yl)benzoic acid (26a)

26a

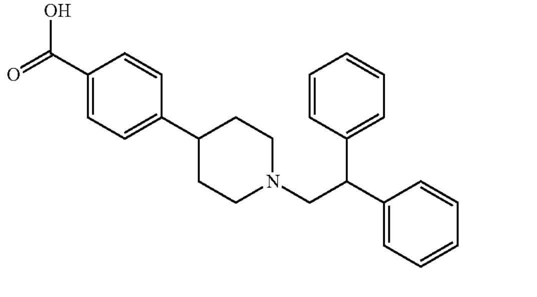

To a solution of 4-(piperidin-4-yl)benzoic acid hydrochloride (317 mg, 1.3 mmol), 2,2-diphenylacetaldehyde (510 mg, 2.6 mmol) and AcOH (1.0 mL) in MeOH (13 mL) was added $NaBH_3CN$ (250 mg, 3.9 mmol). The mixture was stirred at ambient temperature for 2 h. After removal of the solvent by evaporation, the residue was dissolved in EtOAc and washed $NaHCO_3$ (aq.) solution. The organic layer was dried over $Na_2SO_4$, and evaporated to dryness. The crude product was purified by silica gel chromatography to give 4-(1-(2,2-diphenylethyl)piperidin-4-yl)benzoic acid (26a) (340 mg). MS-ESI (m/z): 386 $[M+1]^+$.

(5-Fluoro-2,4-dioxo-3,4-dihydropyrimidin-1(2H)-yl) methyl 4-(1-(2,2-diphenylethyl)piperidin-4-yl)benzoate (26)

26

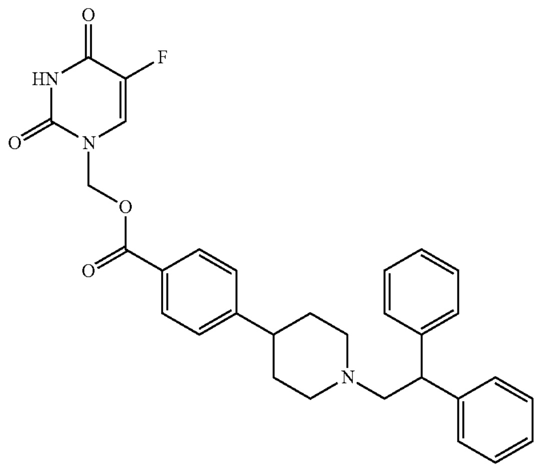

To a solution of 4-(1-(2,2-diphenylethyl)piperidin-4-yl) benzoic acid (26a) (300 mg, 0.78 mmol) and 1H-benzotriazol-1-yloxytris(dimethylamino)phosphonium hexafluorophosphate (BOP) (520 mg, 1.2 mmol) in MeCN (8 mL) was added DIPEA (690 ul, 3.9 mmol). The mixture was stirred at room temperature for 1 h and then was added into the suspension of 5-fluoro-1-(hydroxymethyl)pyrimidine-2,4 (1H,3H)-dione (1a) (435 mg) in MeCN (7 mL) and stirred for 1 h. The suspension was filtered and the filtrate was distilled to a residue. The residue was purified by column chromatography on silica gel followed by prep. HPLC to afford (5-fluoro-2,4-dioxo-3,4-dihydropyrimidin-1(2H)-yl) methyl 4-(1-(2,2-diphenylethyl)piperidin-4-yl)benzoate (26) (192 mg). MS-ESI (m/z): 528 $[M+1]^+$. $^1$H NMR (400 MHz, Chloroform-d) δ 7.61 (d, J=5.2 Hz, 1H), 7.37 (d, J=7.4 Hz, 4H), 7.29-7.20 (m, 4H), 7.20-7.10 (m, 4H), 7.06 (d, J=8.6 Hz, 2H), 5.74 (s, 2H), 4.22 (s, 1H), 2.85 (d, J=11.5 Hz, 2H), 2.53 (d, J=6.7 Hz, 2H), 1.77 (t, J=11.3 Hz, 2H), 1.63-1.43 (m, 3H), 1.39-1.25 (m, 2H).

Example 27

Drug Release Assay

Method

Preparation of pH2.0 Buffer Solution

The pH2.0 buffer solution was prepared by adding 50 mL of 0.1M phosphoric acid solution in a 200 mL volumetric flask, adjusting the pH value to 2.0 with a 0.1M sodium dihydrogen phosphate solution, then diluting to 200 mL with water.

Preparation of pH7.4 Buffer Solution

The pH7.4 buffer solution was prepared by adding 50 mL of 0.1M disodium hydrogen phosphate solution in a 200 mL volumetric flask, adjusting the pH value to 7.4 with a 0.1M phosphoric acid solution, then diluting to 200 mL with water.

| HPLC condition | |
|---|---|
| Column | Agilent XDB-C18 (250 mm × 4.6 mm) 5.0 μm |
| Mobile phase | Gradient |
| | Phase A: $H_2O$:ACN = 9:1 (0.05% TFA); |
| | Phase B: $H_2O$:ACN = 1:9 (0.05% TFA); |
| Flow rate | 1.0 mL/min |
| Detection wavelength | 254 nm |
| Volume of sample inject | 10 μL |
| column oven temperature | 40° C. |
| Detection wavelength | 254 nm/215 nm |
| Volume of sample inject | 10 μL |

Method of Hydrolysis Rate Test

The compounds were dissolved in pH7.4/pH2.0 buffer solution, placed in a constant temperature shaker at 37° C. and 200 rpm, and sampled at 0 h, 0.5 h and 6 h respectively. The residual contents of the compounds relative to 0 h were tested at each time point.

The release rates (%) were calculated using the following equation: Release rate (%)=[A(0h)−A(xh)]/A(0h)×100%, (x=0, 0.5, 6), A(xh) is the peak area of compounds tested by HPLC at the indicated time point.

The hydrolysis constants ($K_h$) were calculated using the following equation:

Hydrolysis constant $K_h$=−ln[100%−Release rate (%)]/$t$

Results

Results of the parent drug release for exemplary prodrug compounds of the present disclosure are shown in Table 1.

TABLE 1

| Example No. | Release rate (%) pH 7.4 (0.5 h) | pH 7.4 (6 h) | pH 2.0 (6 h) | Hydrolysis constant $K_h$ pH 7.4 | pH 2.0 |
|---|---|---|---|---|---|
| Example 1 | 5.4 | 64 | 0 | 0.111 | <0.001 |
| Example 2 | 69.5 | 89 | 38 | 2.375 | 0.080 |
| Example 3 | 60.8 | 100 | 60 | 1.873 | 0.153 |
| Example 4 | 82.7 | 98 | 21 | 3.509 | 0.039 |
| Example 5 | 94.6 | 95 | 56 | 5.838 | 0.137 |
| Example 6 | 82.8 | 75 | 18 | 3.521 | 0.033 |
| Example 7 | 99.3 | 92 | 16 | 9.924 | 0.029 |
| Example 8 | 99.6 | 99 | 22 | 11.043 | 0.041 |
| Example 9 | 89.5 | 90 | 15 | 4.508 | 0.027 |
| Example 10 | 12.0 | 54 | 37 | 0.256 | 0.077 |
| Example 11 | 5.7 | 83 | 33 | 0.117 | 0.067 |
| Example 12 | 100.0 | 100.0 | 9.2 | >20 | 0.016 |
| Example 13 | 2.1 | 23.3 | 0.5 | 0.042 | <0.001 |
| Example 14 | 85.6 | 84.4 | 8.4 | 3.876 | 0.015 |
| Example 15 | 20.6 | 78.5 | 4.2 | 0.461 | 0.007 |
| Example 16 | 96.2 | 100 | 0.4 | 6.540 | <0.001 |
| Example 17 | 4.7 | 57.4 | 43.6 | 0.096 | 0.095 |
| Example 18 | 8.8 | 11.9 | 0.3 | 0.184 | <0.001 |
| Example 19 | 35.1 | 100 | 21.8 | 0.865 | 0.041 |
| Example 20 | 100 | 100 | 37.2 | >20 | 0.078 |
| Example 21 | 81.7 | 100 | 0 | 3.397 | <0.001 |
| Example 22 | 12.5 | 85.4 | 0 | 0.267 | <0.001 |
| Example 23 | 7.2 | 70.8 | 2.5 | 0.149 | 0.004 |
| Example 24 | 4.6 | 55.7 | 0 | 0.094 | <0.001 |
| Example 25 | 20.2 | 61.3 | 40.5 | 0.451 | 0.151 |

As shown in Table 1, the hydrolysis constant ($K_h$) of the present disclosed compounds at pH 7.4 are greater than that at pH 2.

Example 28

Rat Pharmacokinetics Assay

The objective of this study was to assess the pharmacokinetics of free fluorouracil and an exemplary compound of the present disclosure in stomach and plasma following the continuous intragastric administration of the exemplary compound of the present disclosure and the continuous intravenous infusion or single oral administration of free fluorouracil to male Sprague Dawley rats.

Figure 2:
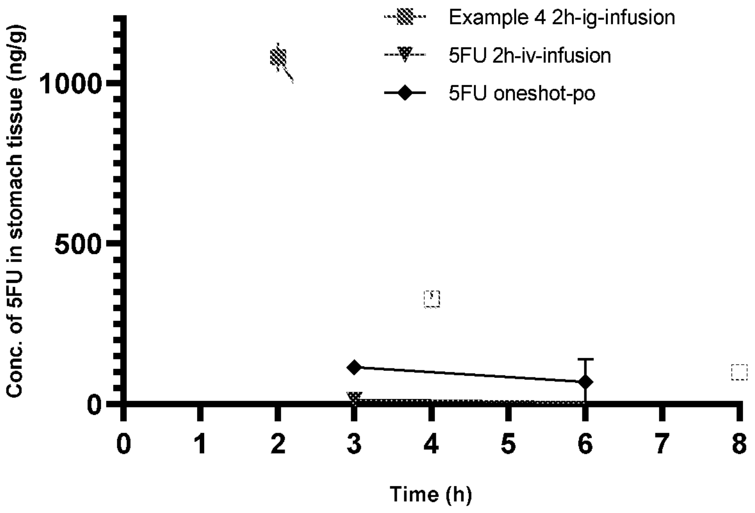

Following the administration of the exemplary compound and free fluorouracil at the same molar amount, the plasma and gastric concentration of fluorouracil were tested and are shown in FIG. 1 and FIG. 2, respectively.

From FIG. 1, it can be seen that the concentration of fluorouracil released from the exemplary compound in plasma is lower compared with that achieved by continuous intravenous infusion or single oral administration of free fluorouracil. This indicated the prodrug of the present disclosure has lower systematic exposure than parent drug and reduced systematic side effects of fluorouracil. From FIG. 2, it can be seen that the concentration of fluorouracil released from the exemplary compound in stomach tissue is higher compared with that achieved by continuous intravenous infusion or single oral administration of free fluorouracil. This indicated the prodrug of the present disclosure achieved sustained release of fluorouracil at stomach tissue.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

What is claimed is:

1. A prodrug compound , or a pharmaceutically acceptable salt thereof, wherein the prodrug compound is selected from the group consisting of:

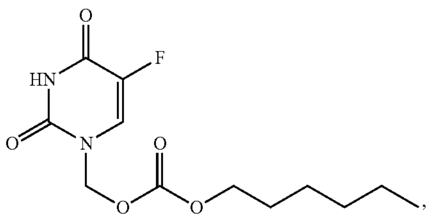

,

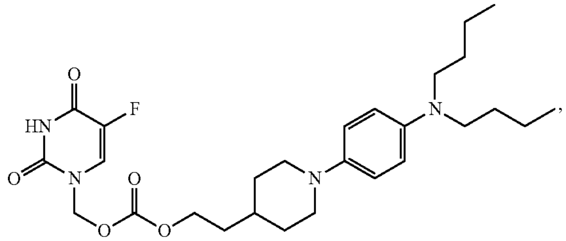

,

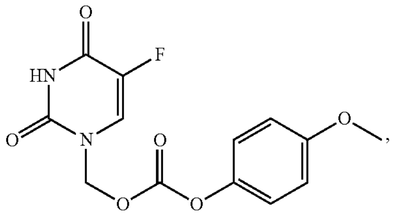

,

-continued

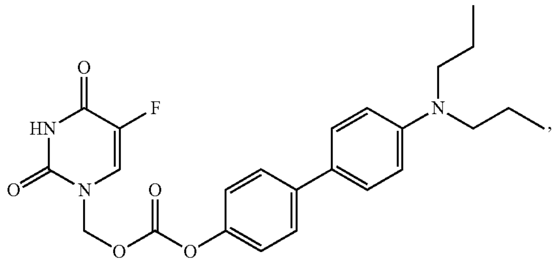

,

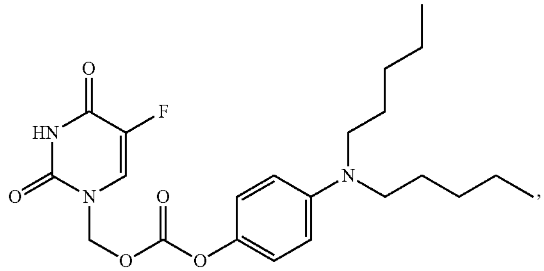

,

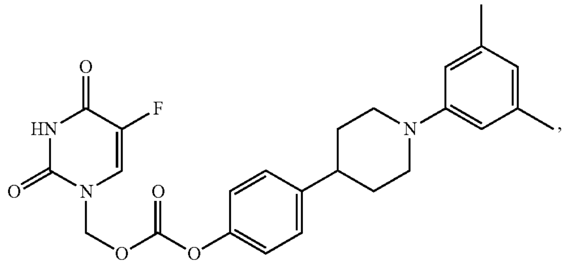

,

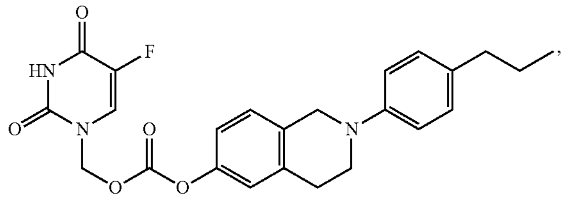

,

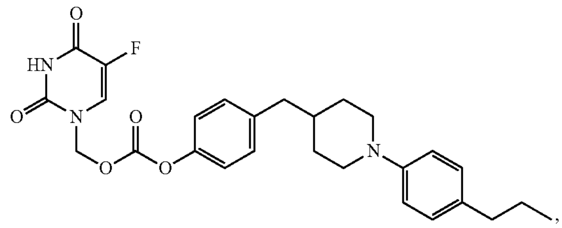

,

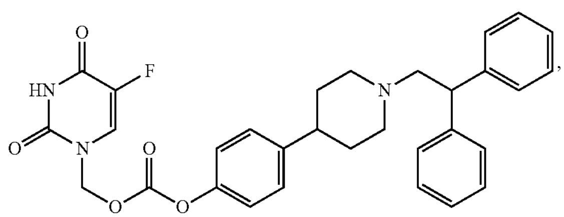

,

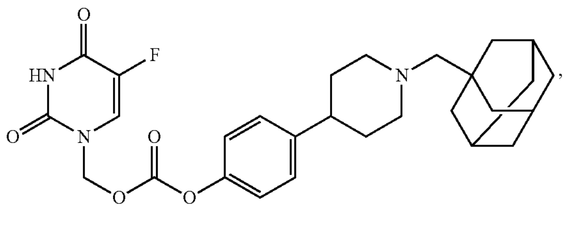

,

-continued
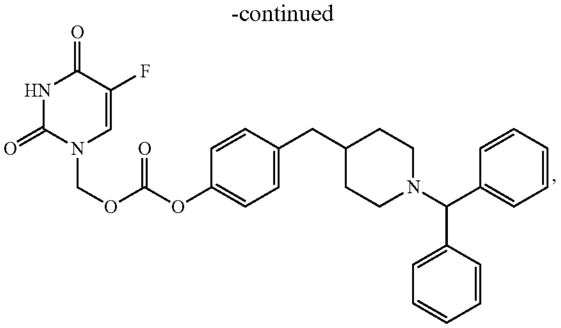
,
and
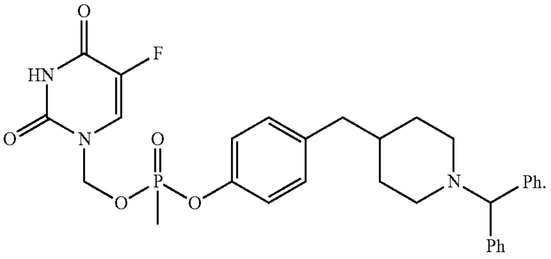
2. A pharmaceutical composition comprising the prodrug compound according to claim 1 or a pharmaceutically acceptable salt thereof, and a pharmaceutically acceptable excipient.
* * * * *